US010005835B2

(12) United States Patent
Carayon et al.

(10) Patent No.: US 10,005,835 B2
(45) Date of Patent: Jun. 26, 2018

(54) ANTI-IL-4/ANTI-IL-13 BISPECIFIC ANTIBODY FORMULATIONS

(71) Applicant: Sanofi, Paris (FR)

(72) Inventors: Sophie Carayon, Paris (FR); Otmane Boussif, Paris (FR)

(73) Assignee: SANOFI, Paris (FR)

( * ) Notice: Subject to any disclaimer, the term of this patent is extended or adjusted under 35 U.S.C. 154(b) by 0 days. days.

(21) Appl. No.: 14/787,507

(22) PCT Filed: Apr. 29, 2014

(86) PCT No.: PCT/EP2014/058733
§ 371 (c)(1),
(2) Date: Oct. 28, 2015

(87) PCT Pub. No.: WO2014/177568
PCT Pub. Date: Nov. 6, 2014

(65) Prior Publication Data
US 2016/0075777 A1 Mar. 17, 2016

Related U.S. Application Data

(60) Provisional application No. 61/816,899, filed on Apr. 29, 2013.

(30) Foreign Application Priority Data

Feb. 5, 2014 (EP) .................. 14305160

(51) Int. Cl.
C07K 16/24 (2006.01)
A61K 39/395 (2006.01)
A61K 47/22 (2006.01)
A61K 47/26 (2006.01)
C07K 16/46 (2006.01)
A61K 39/00 (2006.01)

(52) U.S. Cl.
CPC ........ C07K 16/247 (2013.01); A61K 39/3955 (2013.01); A61K 39/39591 (2013.01); A61K 47/22 (2013.01); A61K 47/26 (2013.01); C07K 16/244 (2013.01); C07K 16/468 (2013.01); A61K 2039/505 (2013.01); A61K 2039/54 (2013.01); A61K 2039/545 (2013.01); C07K 2317/24 (2013.01); C07K 2317/31 (2013.01); C07K 2317/626 (2013.01); C07K 2317/64 (2013.01); C07K 2317/76 (2013.01); C07K 2317/94 (2013.01)

(58) Field of Classification Search
None
See application file for complete search history.

(56) References Cited

U.S. PATENT DOCUMENTS

| 4,444,887 | A | 4/1984 | Hoffmann |
| 4,716,111 | A | 12/1987 | Osband et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,585,089 | A | 12/1996 | Queen et al. |
| 5,814,318 | A | 9/1998 | Lonberg et al. |
| 5,869,619 | A | 2/1999 | Studnicka |
| 2004/0033228 | A1 | 2/2004 | Krause et al. |
| 2012/0121580 | A1 | 5/2012 | Bhambhani |
| 2012/0251541 | A1 | 10/2012 | Baurin et al. |

FOREIGN PATENT DOCUMENTS

| EP | 0239400 A2 | 9/1987 |
| EP | 0519596 A1 | 12/1992 |
| EP | 0592106 A1 | 4/1994 |
| WO | WO9109967 A1 | 7/1991 |
| WO | WO9110741 A1 | 7/1991 |
| WO | WO9633735 A1 | 10/1996 |
| WO | WO9634096 A1 | 10/1996 |
| WO | WO9816654 A1 | 4/1998 |
| WO | WO9824893 A2 | 6/1998 |
| WO | WO9846645 A2 | 10/1998 |
| WO | WO9850433 A2 | 11/1998 |
| WO | WO03035847 A2 | 5/2003 |
| WO | WO03038041 A2 | 5/2003 |
| WO | WO-2004/016286 A2 | 2/2004 |
| WO | WO2006042333 A2 | 4/2006 |
| WO | WO 2008/086395 * | 7/2008 |
| WO | 2009/052081 | 4/2009 |
| WO | WO2009052081 A2 | 4/2009 |
| WO | WO-2009/070642 A1 | 6/2009 |
| WO | WO-2010/066762 A1 | 6/2010 |

(Continued)

OTHER PUBLICATIONS

Wang et al. J Pharmaceutical Scieince, 2007; 96(1); pp. 1-26.*
Wang et al. Int J Pharmaceuticals; 1999; vol. 185, pp. 129-188.*
Akers et al. (Development and Manufacture of Protein Pharmaceuticals (Pharmaceutical Biotechnology), Chapter 2, 2002 Kluver Academic/Plenum Pub., New York).*
Creative Biolabs, (2007-2017); bispecific Antibody (Tand-L033).*
Spiess et al, The Journal of Biological Chemistry; Sep. 2013; vol. 288, No. 37, pp. 26583-26593.*
Kasaian et al, American Journal of Respiratory Cell and Molecular Biology, Jul. 2013; vol. 49; pp. 37-46.*

(Continued)

Primary Examiner — Bridget E Bunner
(74) Attorney, Agent, or Firm — Morrison & Foerster LLP

(57) ABSTRACT

The present invention provides stable pharmaceutical antibody formulations, including lyophilized formulations, comprising an anti-IL-4/anti-IL-13 bispecific antibody and a buffering system, wherein the pH of the formulation is about pH 7, and wherein the formulation has a low salt concentration in order to reduce the ionic strength of the formulation. The formulations may, optionally, further comprise a non-ionic surfactant, a sugar, and/or a non-ionic stabilizing agent. The formulations can be used in the treatment of various diseases.

30 Claims, 37 Drawing Sheets

(56) References Cited

FOREIGN PATENT DOCUMENTS

WO       2012/125775        9/2012
WO       WO2012125775 A1    9/2012

OTHER PUBLICATIONS

Altschul, S. F. et al., "Basic Local Alignment Search Tool," J Mol Biol. Oct. 5, 1990; 215(3):403-410.
Altschul, S. F. et al., "Gapped BLAST and PSI-BLAST: a new generation of protein database search programs," Nucleic Acids Res. Sep. 1, 1997; 25(17):3389-3402.
Ausubel, F. M. et al., Chapter 11: Immunology in: Short Protocols in Molecular Biology, 5th Edition, vol. 1; John Wiley and Sons, Inc., New York (2002).
Carter, P. et al., "Humanization of an anti-p185HER2 antibody for human cancer therapy," Proc. Natl. Acad. Sci. USA (1992) 89: 4285-4289.
Chothia, C. et al., "Canonical Structures for the Hypervariable Regions of Immunoglobulins," J Mol Biol (1987) 196:901-917.
Heinzmann, A. et al., "Genetic variants of IL-13 signalling and human asthma and atopy," Hum Mol Genet. (2000) 9:549-559.
Jones, A., "Analysis of polypeptides and proteins," Adv. Drug Delivery Rev. (1993) 10:29-90.
Kabat, E. A. et al., "Attempts to locate complementary-determining residues in the variable positions of light and heavy chains," (1971) Ann. NY Acad. Sci. 190:382-393.
Kabat, E. A. et al., "Attempts to locate residues in complementarity-determining regions of antibody combining sites that make contact with antigen," Proc. Nat. Acad. Sci. USA (1976) 73(2):617-619.
Kabat, E. A. et al., "Sequences of Proteins of Immunological Interest," Fifth Edition, U.S. Department of Health and Human Services, NIH Publication No. 91-3242 (1991), 83 pages.
Karlin, S. et al. "Applications and statistics for multiple high-scoring segments in molecular sequences," Proc. Natl. Acad. Sci. USA (1993) 90:5873-5877.
Karlin, S. et al. "Methods for assessing the statistical significance of molecular sequence features by using general scoring schemes," Proc. Natl. Acad. Sci. U S A. Mar. 1990 87:2264-2268.
Köhler, G. et al. "Continuous cultures of fused cells secreting antibody of predefined specificity," Nature; Aug. 7, 1975; 256(5514):495-497.
Lazar, G. A., et al., "A molecular immunology approach to antibody humanization and functional optimization," Mol Imm. (2007) 44:1986-1988.
Myers, E. W. et al., "Optimal alignments in linear space," Comput Appl Biosci. Mar. 1988; 4(1):11-17.
Ngoc, L. P. et al. "Cytokines, allergy, and asthma," Curr. Opin. Allergy Clin. Immunol. (2005) 5:161-166.
Padlan, E. A., "A possible procedure for reducing the immunogenicity of antibody variable domains while preserving their ligand-binding properties," Mol Immunol. Apr.-May 1991; 28(4-5):489-498.
Paul, W. E. ed., Fundamental Immunology: Second Edition, Raven Press, New York at (1989) pp. 332-336.
Pearlman, R. et al., "6: Analysis of Protein Drugs," in Peptide and Protein Drug Delivery, Vincent H. L. Lee Ed., Marcel Dekker, Inc., New York, N.Y., Pubs. (1991) 247-301.
Presta, L. G. et al., "Humanization of an antibody directed agains IgE," J Immunol, (1993) 151:2623-2632.
Roguska, M. A. et al., "Humanization of murine monoclonal antibodies through variable domain resurfacing," PNAS (1994) 91:969-973.
Sims, M.J. et al., "A humanized CD18 antibody can block function without cell destruction," J. Immunol. (1993) 151:2296-2308.
Studnicka, G. M. et al., "Human-engineered monoclonal antibodies retain full specific binding activity by preserving non-CDR complementarity-modulating residues," Prot Eng (1994) 7(6):805-814.
Taylor, L. D. et al., "A transgenic mouse that expresses a diversity of human sequence heavy and light chain immunoglobulins," Nucl. Acids Res. (1992) 20(23):6287-6295.
International Search Report dated Aug. 6, 2014, issued in connection with International Application No. PCT/EP2014/058733, filed on Apr. 29, 2014, 8 pages.
Written Opinion of the International Searching Authority dated Aug. 6, 2014, issued in connection with International Application No. PCT/EP2014/058733, filed on Apr. 29, 2014, 8 pages.
International Preliminary Report on Patentability dated Nov. 3, 2015, issued in connection with International Application No. PCT/EP2014/058733, filed on Apr. 29, 2014, 9 pages.
Daugherty, A.L. et al. (2010). "Formulation and Delivery Issues for Monoclonal Antibody Therapeutics," Chapter 8 in *Current Trends in Monoclonal Antibody Development and Manufacturing*, Biotechnology: Pharmaceutical Aspects, S.J. Shrine (ed.) et al., Springer, pp. 103-129.

* cited by examiner

FIG. 2

Anti-IL13 hB-B13 VL3 (SEQ ID NO: 1):
DIVLTQSPAS LAVSLGQRAT ISCRASESVD SYGQSYMHWY QQKAGQPPKL
LIYLASNLES GVPARFSGSG SRTDFTLTID PVQAEDAATY YCQQNAEDSR
TFGGGTKLEI K Anti-IL13 hB-B13 VH2 (SEQ ID NO: 2):
EVQLKESGPG LVAPGGSLSI TCTVSGFSLT DSSINWVRQP PGKGLEWLGM
IWGDGRIDYA DALKSRLSIS KDSSKSQVFL EMTSLRTDDT ATYYCARDGY
FPYAMDFWGQ GTSVTVSS Anti-IL4 h8D4-8 VL1 (SEQ ID NO: 3):
DIQMTQSPAS LSVSVGDTIT LTCHASQNID VWLSWFQQKP GNIPKLLIYK
ASNLHTGVPS RFSGSGSGTG FTLTISSLQP EDIATYYCQQ AHSYPFTFGG
GTKLEIKR Anti-IL4 h8D4-8 VH1 (SEQ ID NO: 4):
QVQLQQSGPE LVKPGASVKI SCKASGYSFT SYWIHWIKQR PGQGLEWIGM
IDPSDGETRL NQRFQGRATL TVDESTSTAY MQLRSPTSED SAVYYCTRLK
EYGNYDSFYF DVWGAGTLVT VSSA Anti-IL4 h8D4-8 VH2 (SEQ ID NO: 5):
QVQLQQSGPE LVKPGASVKI SCKASGYSFT SYWIHWIKQR PGQGLEWIGM
IDASDGETRL NQRFQGRATL TVDESTSTAY MQLRSPTSED SAVYYCTRLK
EYGNYDSFYF DVWGAGTLVT VSSA FIG. 27
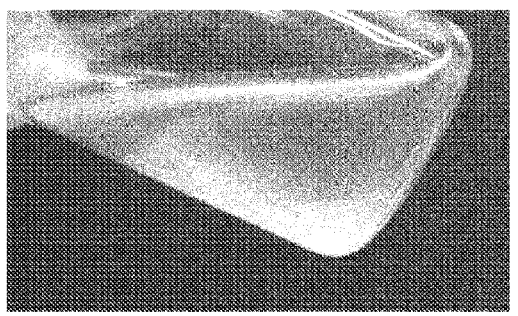
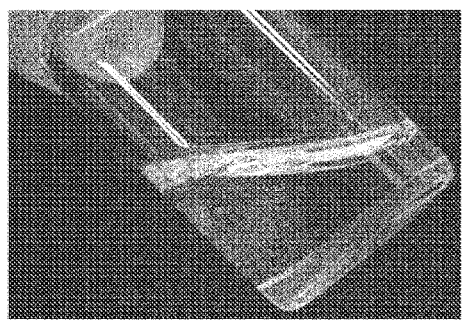
Histidine RT    Succinate 5°C

FIG. 34

| Time (h) | ΔHMW at RT | | | | | | |
|---|---|---|---|---|---|---|---|
| | 185 A2 - Glycine 72mM | 185 A1 - Sucrose 2.4% | 185 B1 Phos 1.75mM Glycine 72mM | 185 B2 Phos 1.75mM Sucrose 2.4% | 185 C2 Citrate 1.75mM Glycine 72mM | 185 C3 Citrate 1.75mM Sucrose 2.4% | Reference 185 D |
| 0 | 0,0 | 0,0 | 0,0 | 0,0 | 0,0 | 0,0 | 0,0 |
| 24 | 3,9 | 4,1 | 4,0 | 4,2 | 3,2 | 4,1 | 3,2 |
| 48 | 7,0 | 7,5 | 7,5 | 7,5 | 7,1 | 7,9 | 6,8 |
| 72 | 9,8 | 10,1 | 10,4 | 10,4 | 10,1 | 10,9 | 9,8 |

SEQUENCE LISTING

```
<160> NUMBER OF SEQ ID NOS: 21

<210> SEQ ID NO 1
<211> LENGTH: 111
<212> TYPE: PRT
<213> ORGANISM: Artificial Sequence
<220> FEATURE:
<223> OTHER INFORMATION: Anti-IL13 hB-B13 VL3

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Gln Ser Tyr Met His Trp Tyr Gln Gln Lys Ala Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys
                100                 105                 110

<210> SEQ ID NO 2
<211> LENGTH: 118
<212> TYPE: PRT
<213> ORGANISM: Artificial Sequence
<220> FEATURE:
<223> OTHER INFORMATION: Anti-IL13 hB-B13 VH2

<400> SEQUENCE: 2

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
                20                  25                  30

Ser Ile Asn Trp Val Arg Gln Pro Pro Gly Lys Gly Leu Glu Trp Leu
            35                  40                  45

Gly Met Ile Trp Gly Asp Gly Arg Ile Asp Tyr Ala Asp Ala Leu Lys
        50                  55                  60
```

```
Ser Arg Leu Ser Ile Ser Lys Asp Ser Ser Lys Ser Gln Val Phe Leu
 65                  70                  75                  80

Glu Met Thr Ser Leu Arg Thr Asp Asp Thr Ala Thr Tyr Tyr Cys Ala
                 85                  90                  95

Arg Asp Gly Tyr Phe Pro Tyr Ala Met Asp Phe Trp Gly Gln Gly Thr
            100                 105                 110

Ser Val Thr Val Ser Ser
        115

<210> SEQ ID NO 3
<211> LENGTH: 108
<212> TYPE: PRT
<213> ORGANISM: Artificial Sequence
<220> FEATURE:
<223> OTHER INFORMATION: Anti-IL4 h8D4-8 VL1

<400> SEQUENCE: 3

Asp Ile Gln Met Thr Gln Ser Pro Ala Ser Leu Ser Val Ser Val Gly
 1               5                  10                  15

Asp Thr Ile Thr Leu Thr Cys His Ala Ser Gln Asn Ile Asp Val Trp
             20                  25                  30

Leu Ser Trp Phe Gln Gln Lys Pro Gly Asn Ile Pro Lys Leu Leu Ile
         35                  40                  45

Tyr Lys Ala Ser Asn Leu His Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Ala His Ser Tyr Pro Phe
                 85                  90                  95

Thr Phe Gly Gly Gly Thr Lys Leu Glu Ile Lys Arg
            100                 105

<210> SEQ ID NO 4
<211> LENGTH: 124
<212> TYPE: PRT
<213> ORGANISM: Artificial Sequence
<220> FEATURE:
<223> OTHER INFORMATION: Anti-IL4 h8D4-8 VH1

<400> SEQUENCE: 4

Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Ser Tyr
             20                  25                  30

Trp Ile His Trp Ile Lys Gln Arg Pro Gly Gln Gly Leu Glu Trp Ile
         35                  40                  45

Gly Met Ile Asp Pro Ser Asp Gly Glu Thr Arg Leu Asn Gln Arg Phe
 50                  55                  60

Gln Gly Arg Ala Thr Leu Thr Val Asp Glu Ser Thr Ser Thr Ala Tyr
 65                  70                  75                  80

Met Gln Leu Arg Ser Pro Thr Ser Glu Asp Ser Ala Val Tyr Tyr Cys
                 85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120
```

```
<210> SEQ ID NO 5
<211> LENGTH: 124
<212> TYPE: PRT
<213> ORGANISM: Artificial Sequence
<220> FEATURE:
<223> OTHER INFORMATION: Anti-IL4 h8D4-8 VH2

<400> SEQUENCE: 5

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Ala Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120

<210> SEQ ID NO 6
<211> LENGTH: 10
<212> TYPE: PRT
<213> ORGANISM: Artificial Sequence
<220> FEATURE:
<223> OTHER INFORMATION: linker

<400> SEQUENCE: 6

Gly Gly Gly Gly Ser Gly Gly Gly Gly Ser
1               5                   10

<210> SEQ ID NO 7
<211> LENGTH: 15
<212> TYPE: PRT
<213> ORGANISM: Artificial Sequence
<220> FEATURE:
<223> OTHER INFORMATION: hB-B13 VL3 CDR1

<400> SEQUENCE: 7

Arg Ala Ser Glu Ser Val Asp Ser Tyr Gly Gln Ser Tyr Met His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: hB-B13 VL3 CDR2

<400> SEQUENCE: 8

Leu Ala Ser Asn Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: hB-B13 VL3 CDR3
```

```
<400> SEQUENCE: 9

Gln Gln Asn Ala Glu Asp Ser Arg Thr
1               5

<210> SEQ ID NO 10
<211> LENGTH: 10
<212> TYPE: PRT
<213> ORGANISM: Artificial Sequence
<220> FEATURE:
<223> OTHER INFORMATION: hB-B13 VH2 CDR1

<400> SEQUENCE: 10

Gly Phe Ser Leu Thr Asp Ser Ser Ile Asn
1               5                   10

<210> SEQ ID NO 11
<211> LENGTH: 5
<212> TYPE: PRT
<213> ORGANISM: Artificial Sequence
<220> FEATURE:
<223> OTHER INFORMATION: hB-B13 VH2 CDR2

<400> SEQUENCE: 11

Asp Gly Arg Ile Asp
1               5

<210> SEQ ID NO 12
<211> LENGTH: 10
<212> TYPE: PRT
<213> ORGANISM: Artificial Sequence
<220> FEATURE:
<223> OTHER INFORMATION: hB-B13 VH2 CDR3

<400> SEQUENCE: 12

Asp Gly Tyr Phe Pro Tyr Ala Met Asp Phe
1               5                   10

<210> SEQ ID NO 13
<211> LENGTH: 11
<212> TYPE: PRT
<213> ORGANISM: Artificial Sequence
<220> FEATURE:
<223> OTHER INFORMATION: h8D4-8 VL1 CDR1

<400> SEQUENCE: 13

His Ala Ser Gln Asn Ile Asp Val Trp Leu Ser
1               5                   10

<210> SEQ ID NO 14
<211> LENGTH: 8
<212> TYPE: PRT
<213> ORGANISM: Artificial Sequence
<220> FEATURE:
<223> OTHER INFORMATION: h8D4-8 VL1 CDR2

<400> SEQUENCE: 14

Lys Ala Ser Asn Leu His Thr Gly
1               5

<210> SEQ ID NO 15
<211> LENGTH: 9
<212> TYPE: PRT
<213> ORGANISM: Artificial Sequence
<220> FEATURE:
<223> OTHER INFORMATION: h8D4-8 VL1 CDR3
```

<400> SEQUENCE: 15

Gln Gln Ala His Ser Tyr Pro Phe Thr
1               5

<210> SEQ ID NO 16
<211> LENGTH: 10
<212> TYPE: PRT
<213> ORGANISM: Artificial Sequence
<220> FEATURE:
<223> OTHER INFORMATION: h8D4-8 VH1 CDR1

<400> SEQUENCE: 16

Gly Tyr Ser Phe Thr Ser Tyr Trp Ile His
1               5                   10

<210> SEQ ID NO 17
<211> LENGTH: 9
<212> TYPE: PRT
<213> ORGANISM: Artificial Sequence
<220> FEATURE:
<223> OTHER INFORMATION: h8D4-8 VH1 CDR2

<400> SEQUENCE: 17

Ile Asp Pro Ser Asp Gly Glu Thr Arg
1               5

<210> SEQ ID NO 18
<211> LENGTH: 14
<212> TYPE: PRT
<213> ORGANISM: Artificial Sequence
<220> FEATURE:
<223> OTHER INFORMATION: h8D4-8 VH1 CDR3

<400> SEQUENCE: 18

Leu Lys Glu Tyr Gly Asn Tyr Asp Ser Phe Tyr Phe Asp Val
1               5                   10

<210> SEQ ID NO 19
<211> LENGTH: 10
<212> TYPE: PRT
<213> ORGANISM: Artificial Sequence
<220> FEATURE:
<223> OTHER INFORMATION: h8D4-8 VH2 CDR1

<400> SEQUENCE: 19

Gly Tyr Ser Phe Thr Ser Tyr Trp Ile His
1               5                   10

<210> SEQ ID NO 20
<211> LENGTH: 9
<212> TYPE: PRT
<213> ORGANISM: Artificial Sequence
<220> FEATURE:
<223> OTHER INFORMATION: h8D4-8 VH2 CDR2

<400> SEQUENCE: 20

Ile Asp Ala Ser Asp Gly Glu Thr Arg
1               5

<210> SEQ ID NO 21
<211> LENGTH: 14
<212> TYPE: PRT
<213> ORGANISM: Artificial Sequence
<220> FEATURE:
<223> OTHER INFORMATION: h8D4-8 VH2 CDR3

<400> SEQUENCE: 21

```
Leu Lys Glu Tyr Gly Asn Tyr Asp Ser Phe Tyr Phe Asp Val
1               5                  10
```

ANTI-IL-4/ANTI-IL-13 BISPECIFIC ANTIBODY FORMULATIONS

CROSS REFERENCE TO RELATED APPLICATIONS

This application is a National Phase application under 35 U.S.C. § 371 of International Application No. PCT/EP2014/058733, filed Apr. 29, 2014, which claims benefit of U.S. Provisional Application No. 61/816,899, filed Apr. 29, 2013, and which claims priority benefit to European Application No. 14305160.5, filed Feb. 5, 2014, the disclosures of each of which are herein incorporated by reference in their entirety.

FIELD OF THE INVENTION

The present invention provides stable pharmaceutical antibody formulations, including lyophilized formulations, comprising an anti-IL-4/anti-IL-13 bispecific antibody and a buffering system, wherein the pH of the formulation is about pH 7, and wherein the formulation has a low salt concentration in order to reduce the ionic strength of the formulation. The formulations may, optionally, further comprise a non-ionic surfactant, a sugar, and/or a non-ionic stabilizing agent. The formulations can be used in the treatment of various diseases.

BACKGROUND OF THE INVENTION

Both IL-4 and IL-13 are therapeutically important cytokines based on their biological functions and play critical roles in many diseases, including asthma (Curr Opin Allergy Clin Immunol 2005, Vo. 5, 161-166). IL-4 has been shown to be able to inhibit autoimmune disease, and IL-4 and IL-13 have both shown the potential to enhance anti-tumor immune responses. Since both cytokines are involved in the pathogenesis of allergic diseases, inhibitors of these cytokines could provide therapeutic benefits.

In order to develop a pharmaceutical formulation containing an anti-IL-4/anti-IL-13 bispecific antibody suitable for subcutaneous administration, the antibody must be concentrated to about 100 mg/mL or greater. However, many complications can arise at such high concentrations, including an increase in viscosity, a shift of pH, a change in the color of the solution, and the formation of visible and sub-visible particles. Formulation of the antibody is further complicated by the fact that it is highly prone to aggregation at high concentrations. While typical antibodies normally form high molecular weight aggregates (HMW) below 5% over a time period of 4 years at 5° C., the anti-IL-4/anti-IL-13 bispecific antibody forms HMW at a rate of between 0.5-1% per hour at 25° C., and at 0.1% per hour at 5° C. Indeed, this antibody has such a strong propensity to aggregate that it cannot be formulated in a liquid in the concentration range targeted. Finally, the anti-IL4/anti-IL13 bispecific antibody has a particularly low isoelectric point, making it more difficult to formulate due to solubility issues. For example, the anti-IL4/anti-IL13 bispecific antibody has an isoelectric point between 5.8 and 6.2, whereas most antibodies have an isoelectric point between 8 and 10.

Accordingly, a need exists for improved and stable pharmaceutical formulations that can address these complications.

SUMMARY OF THE INVENTION

To meet these and other needs, provided herein are highly stable anti-IL-4/anti-IL-13 bispecific antibody formulations. Highly stable anti-IL-4/anti-IL-13 bispecific antibody formulations have surprisingly been found in the form of liquids and lyophilized powders that comprise an anti-IL-4/anti-IL-13 bispecific antibody and a buffering system, wherein the pH of the formulation is about pH 7, and wherein the formulation has a low salt concentration in order to reduce the ionic strength of the formulation. The formulations may, optionally, further comprise a non-ionic surfactant, a sugar, and/or a non-ionic stabilizing agent. These formulations improve upon conventional formulations, which often lead to molecular aggregation (HMW) of the antibody upon increasing the concentration of the antibody in the formulation, and the formation of visible and sub-visible particles. In particular, the formulations of the invention exhibit good stability regarding visible particles, sub-visible particles, low molecular weight proteins, and high molecular weight proteins.

An embodiment of the invention provides a stable antibody formulation comprising: a bispecific anti-IL-4/anti-IL-13 antibody or an antigen binding fragment thereof, comprising a light chain of the formula VL1-linker-VL2 and a heavy chain of the formula VH1-linker-VH2, wherein VL1 and VH1 form an IL-13 antigen binding domain and VL2 and VH2 form an IL-4 antigen binding domain; and a buffering system suitable to maintain the pH of the formulation at about pH 7; and wherein the formulation has a low salt concentration in order to reduce the ionic strength of the formulation.

In specific embodiments, VL1 comprises the CDR sequences of SEQ ID NO: 1; VH1 comprises the CDR sequences of SEQ ID NO: 2; VL2 comprises the CDR sequences of SEQ ID NO: 3; and VH2 comprises the CDR sequences of SEQ ID NO: 4 or 5. In alternative specific embodiments, VL1 comprises the amino acid sequence of SEQ ID NO: 1; VH1 comprises the amino acid sequence of SEQ ID NO: 2; VL2 comprises the amino acid sequence of SEQ ID NO: 3; and VH2 comprises the amino acid sequence of SEQ ID NO: 4 or 5.

In specific embodiments, the light chain comprises the formula N-VL1-linker-VL2-CL, wherein CL is a light chain constant domain of an antibody, and wherein the heavy chain comprises the formula N-VH1-linker-VH2-CH1-CH2-CH3, wherein CH2-CH3 corresponds to the Fc domain of an antibody. In specific embodiments, the linker comprises the amino acid sequence of SEQ ID NO: 6.

In specific embodiments, the antibody or antigen binding fragment thereof further comprises a constant region domain. In specific embodiments, the constant region domain is selected from the group consisting of CH1, CH2, CH3, and CL.

In specific embodiments, the bispecific antibody or antigen binding fragment thereof is a humanized IgG4 bispecific antibody or antigen binding fragment thereof.

In specific embodiments, the concentration of antibody or antigen binding fragment thereof is about 100 mg/mL.

In certain embodiments of the invention, the buffering system comprises at least two buffers. In specific embodiments, the buffering system concentration is about 10 mM. In specific embodiments, the buffering system comprises Tris buffer and Phosphate buffer. In specific embodiments, the Tris buffer concentration is about 3.7 mM. In specific embodiments, the Phosphate buffer concentration is about 6.3 mM. In specific embodiments, the Tris buffer concentration is about 3.7 mM and the Phosphate buffer concentration is about 6.3 mM.

In certain embodiments of the invention, the formulation further comprises a non-ionic surfactant. In specific embodiments, the non-ionic surfactant concentration is about 0.05% to about 0.2% (w/v). In specific embodiments, the non-ionic surfactant is a polysorbate. In specific embodiments, the polysorbate is polysorbate 80. In specific embodiments, the polysorbate 80 concentration is about 0.05% to about 0.2% (w/v). In specific embodiments, the polysorbate 80 concentration is about 0.2% (w/v).

In certain embodiments of the invention, the formulation further comprises a sugar. In specific embodiments, the sugar concentration is about 5% (w/v). In specific embodiments, the sugar is a disaccharide. In specific embodiments, the disaccharide is sucrose. In specific embodiments, the sucrose concentration is about 5% (w/v).

In certain embodiments of the invention, the formulation further comprises a non-ionic stabilizing agent. In specific embodiments, the non-ionic stabilizing agent concentration is about 1% to about 3% (w/v). In specific embodiments, the non-ionic stabilizing agent is either an amino acid or a sugar. In specific embodiments, the amino acid is proline. In specific embodiments, the sugar is mannitol. In specific embodiments, the proline concentration is about 1% to about 3% (w/v). In specific embodiments, the proline concentration is about 3% (w/v). In specific embodiments, the mannitol concentration is about 3% (w/v).

In certain embodiments of the invention, the formulation is a lyophilized formulation.

In certain embodiments of the invention, the formulation exhibits good stability regarding visible particles, sub-visible particles, low molecular weight proteins, and high molecular weight proteins.

An embodiment of the invention provides a stable lyophilized antibody formulation comprising: about 100 mg/mL of a bispecific antibody or an antigen binding fragment thereof, wherein the antibody or antigen binding fragment thereof comprises a heavy chain variable region comprising the amino acid sequences of SEQ ID NOs: 2 and 4, and a light chain variable region comprising the amino acid sequences of SEQ ID NOs: 1 and 3; about 10 mM of a buffering system, wherein the buffering system comprises a Tris buffer concentration of about 3.7 mM and a Phosphate buffer concentration of about 6.3 mM; about 0.2% (w/v) polysorbate 80; about 5% (w/v) sucrose; and about 3% (w/v) proline; wherein the pH of the formulation is about pH 7.

An embodiment of the invention provides a stable lyophilized antibody formulation comprising: about 100 mg/mL of a bispecific antibody or an antigen binding fragment thereof, wherein the antibody or antigen binding fragment thereof comprises a heavy chain variable region comprising the amino acid sequences of SEQ ID NOs: 2 and 4, and a light chain variable region comprising the amino acid sequences of SEQ ID NOs: 1 and 3; about 10 mM of a buffering system, wherein the buffering system comprises a Tris buffer concentration of about 3.7 mM and a Phosphate buffer concentration of about 6.3 mM; about 0.2% (w/v) polysorbate 80; about 5% (w/v) sucrose; and about 3% (w/v) mannitol; wherein the pH of the formulation is about pH 7.

An embodiment of the invention provides a kit comprising a container comprising a formulation of the invention and instructions for the administration and use of the formulation.

An embodiment of the invention provides a method for treating an allergic disease, cancer, asthma, a disease associated with abnormal production of IL-4 and/or IL-13, or a disease associated with an elevated TH-2 mediated response comprising administering to a subject in need thereof a formulation of the invention.

BRIEF DESCRIPTION OF THE DRAWINGS

FIG. 2 illustrates the amino acid sequences of an exemplary antibody, i.e., humanized variable domains of B-B13 anti-IL-13 antibody (SEQ ID NOS: 1 and 2) and humanized variable domains of 8D4-8 anti-IL-4 antibody (SEQ ID NOS: 3, 4 and 5). Underline indicates amino acid changes made. Bold indicates the CDR sequences (SEQ ID NOS: 7-21).

FIG. 27 shows pictures of a visual aspect of Histidine and Succinate formulations (assays #P-H04-144 and 148, #H04-150 A1 to A6).

FIG. 34 is a chart showing HMW evolutions for Glycine vs Sucrose at RT by SEC (assays #H04-185).

DETAILED DESCRIPTION

Figure 1:
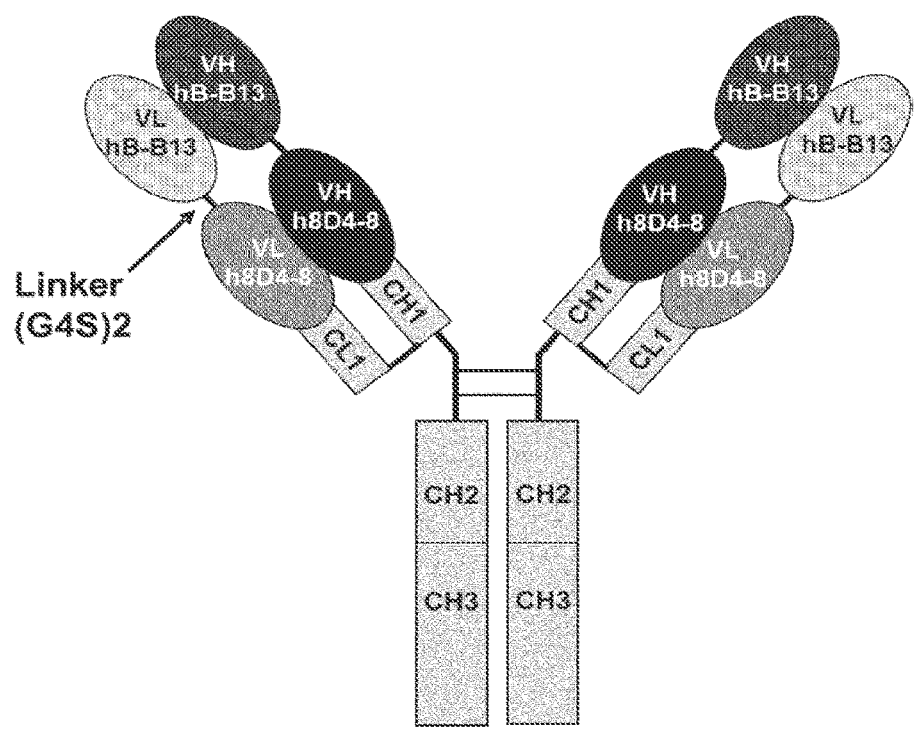
FIG. 1 is a schematic showing an exemplary bispecific anti-IL-4/anti-IL-13 antibody molecule comprising two light chains and two heavy chains. The two light chains comprise the moiety N-$VL_{hB-B13}$-linker-$VL_{h8D4-8}$-CL-C, and the two heavy chains comprise the moiety N-$VH_{hB-B13}$-linker-$VH_{h8D4-8}$-CH1-CH2-CH3-C. The linker sequence comprises (G4S)$_2$ or GGGGSGGGGS (SEQ ID NO: 6).

This invention is not limited to the particular methodology, protocols, cell lines, vectors, or reagents described herein because they may vary without departing from the spirit and scope of the invention. Further, the terminology used herein is for the purpose of exemplifying particular embodiments only and is not intended to limit the scope of the present invention. Any method and material similar or equivalent to those described herein can be used in the practice of the present invention and only exemplary methods, devices, and materials are described herein.

All patents and publications mentioned herein are incorporated herein in entirety by reference for the purpose of describing and disclosing the proteins, enzymes, vectors, host cells and methodologies reported therein that might be used with and in the present invention. However, nothing herein is to be construed as an admission that the invention is not entitled to antedate such disclosure by virtue of prior invention.

A. Definitions

Unless defined otherwise, all technical and scientific terms used herein have the same meaning as is commonly understood by one of ordinary skill in the art.

It is noted here that as used in this specification and the appended claims, the singular forms "a", "an", and "the" also include plural reference, unless the context clearly dictates otherwise.

The term "about" or "approximately" means within 10%, and more preferably within 5% (or 1% or less) of a given value or range.

The terms "administer" or "administration" refers to the act of injecting or otherwise physically delivering a substance as it exists outside the body (e.g., a formulation of the invention) into a patient, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or its symptoms are being prevented, administration of the substance typically occurs before the onset of the disease or symptoms thereof.

In the context of a polypeptide, the term "analog" refers to a polypeptide that possesses a similar or identical function as an anti-IL-4/anti-IL-13 bispecific polypeptide, a fragment of an anti-IL-4/anti-IL-13 bispecific polypeptide, an anti-IL-4/anti-IL-13 bispecific epitope, or an anti-IL-4/anti-IL-13 bispecific antibody, but does not necessarily comprise a similar or identical amino acid sequence of an anti-IL-4/anti-IL-13 bispecific polypeptide, a fragment of an anti-IL-4/anti-IL-13 bispecific polypeptide, an anti-IL-4/anti-IL-13 bispecific epitope, or an anti-IL-4/anti-IL-13 bispecific antibody, or possess a similar or identical structure of an anti-IL-4/anti-IL-13 bispecific polypeptide, a fragment of an anti-IL-4/anti-IL-13 bispecific polypeptide, an anti-IL-4/anti-IL-13 bispecific epitope, or an anti-IL-4/anti-IL-13 bispecific antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, and preferably at least 90%, more preferably at least 95%, or most preferably at least 99% identical to the amino acid sequence of an anti-IL-4/anti-IL-13 bispecific polypeptide (e.g., SEQ ID NOs: 1-5), a fragment of an anti-IL-4/anti-IL-13 bispecific polypeptide, an anti-IL-4/anti-IL-13 bispecific epitope, or an anti-IL-4/anti-IL-13 bispecific antibody described herein; (b) a polypeptide encoded by a nucleotide sequence that hybridizes under stringent conditions to a nucleotide sequence encoding an anti-IL-4/anti-IL-13 bispecific polypeptide, a fragment of an anti-IL-4/anti-IL-13 bispecific polypeptide, an anti-IL-4/anti-IL-13 bispecific epitope, or an anti-IL-4/anti-IL-13 bispecific antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) Molecular Cloning: A Laboratory Manual, Cold Spring Harbor Laboratory Press, Cold Spring Harbor, N.Y.; Maniatis et al. (1982) Molecular Cloning: A Laboratory Manual, Cold Spring Harbor Press, Cold Spring Harbor, N.Y.); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, and preferably at least 90%, more preferably at least 95%, or most preferably at least 99% identical to the nucleotide sequence encoding an anti-IL-4/anti-IL-13 bispecific polypeptide, a fragment of an anti-IL-4/anti-IL-13 bispecific polypeptide, an anti-IL-4/anti-IL-13 bispecific epitope, or an anti-IL-4/anti-IL-13 bispecific antibody (or VH or VL region thereof) described herein. A polypeptide with similar structure to an anti-IL-4/anti-IL-13 bispecific antibody polypeptide, a fragment of an anti-IL-4/anti-IL-13 bispecific polypeptide, an anti-IL-4/anti-IL-13 bispecific epitope, or an anti-IL-4/anti-IL-13 bispecific antibody refers to a polypeptide that has a similar secondary, tertiary or quaternary structure of an anti-IL-4/anti-IL-13 bispecific polypeptide, a fragment of an anti-IL-4/anti-IL-13 bispecific polypeptide, an anti-IL-4/anti-IL-13 bispecific epitope, or an anti-IL-4/anti-IL-13 bispecific antibody. The structure of a polypeptide can determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences (e g, amino acid sequences or nucleic acid sequences) can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to nucleic acid molecules of interest. BLAST protein searches can be performed with the XBLAST program parameters set, e.g., to score 50, wordlength=3 to obtain amino acid sequences homologous to a protein molecule of interest. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web at ncbi dot nlm dot nih dot gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

An "antagonist" or "inhibitor" refers to a molecule capable of inhibiting one or more biological activities of a target molecule, such as signaling by IL-4 and/or IL-13. Antagonists may interfere with the binding of a receptor to a ligand and vice versa, by incapacitating or killing cells activated by a ligand, and/or by interfering with receptor or ligand activation (e.g., tyrosine kinase activation) or signal transduction after ligand binding to a receptor. The antagonist may completely block receptor-ligand interactions or may substantially reduce such interactions. In certain embodiments of the invention, the anti-IL-4/anti-IL-13 bispecific antibodies are humanized, antagonistic anti-IL-4/anti-IL-13 bispecific antibodies, preferably humanized, monoclonal, antagonistic anti-IL-4/anti-IL-13 bispecific antibodies.

The terms "antibody", "immunoglobulin", or "Ig" may be used interchangeably herein. The term antibody includes, but is not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies include immunoglobulin molecules and immunologically active portions of immunoglobulin molecules, i.e., antigen binding domains or molecules that contain an antigen-binding site that specifically binds to an IL-4 or IL-13 antigen (e.g., one or more complementarity determining regions (CDRs) of an anti-IL-4/anti-IL-13 bispecific antibody). The anti-IL-4/anti-IL-13 bispecific antibodies can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In preferred embodiments, the anti-IL-4/anti-IL-13 bispecific antibodies are humanized, such as humanized monoclonal anti-IL-4/anti-IL-13 bispecific antibodies. In certain embodiments, the anti-IL-4/anti-IL-13 bispecific antibodies are IgG antibodies, human IgG4 antibodies.

The term "antigen" refers to a molecule or a portion of a molecule capable of being bound by the antibodies of the present invention. An antigen can have one or more than one epitope. Examples of antigens recognized by the antibodies of the present invention include, but are not limited to, serum proteins, e.g., cytokines such as IL-4, IL5, IL9 and IL-13, bioactive peptides, cell surface molecules, e.g., receptors, transporters, ion-channels, viral and bacterial proteins.

The term "antigen binding site" refers to the part of the antibody that comprises the area that specifically binds to and is complementary to part or all of an antigen. Where an antigen is large, an antibody may only bind to a particular part of the antigen, which part is termed on epitope. An antigen binding domain may be provided by one or more antibody variable domains. Preferably, an antigen binding domain is made of the association of an antibody light chain variable domain (VL) and an antibody heavy chain variable domain (VH).

The term "binding agent" means any molecule, such as an antibody, a siRNA, a nucleic acid, an aptamer, a protein, or a small molecule organic compound, that binds or specifically binds to IL-4 and/or IL-13, or a variant or a fragment thereof.

The terms "bispecific antibody" or "bispecific antibodies (BsAbs)" refers to molecules that combine the antigen-binding sites of two antibodies within a single molecule. Thus, a bispecific antibody is able to bind two different antigens simultaneously. Besides applications for diagnostic purposes, BsAbs pave the way for new therapeutic applications by redirecting potent effector systems to diseased areas or by increasing neutralizing or stimulating activities of antibodies. Bispecific antibodies can be monoclonal, but are preferably human or humanized Methods for making bispecific antibodies are well known in the art.

The term "by-product" includes undesired products, which detract or diminish the proportion of therapeutic/prophylactic binding agent, such as an antibody, in a given formulation. For example, typical by-products include aggregates of the antibody, fragments of the antibody, e.g. produced by degradation of the antibody by deamidation or hydrolysis, or mixtures thereof. Typically, aggregates are complexes that have a molecular weight greater than the monomer antibody. Antibody degradation products may include, for example, fragments of the antibody, for example, brought about by deamidation or hydrolysis. Typically, degradation products are complexes that have a molecular weight less than the monomer antibody. In the case of an IgG antibody, such degradation products are less than about 150 kD.

The terms "composition" and "formulation" are intended to encompass a product containing the specified ingredients (e.g., an anti-IL-4/anti-IL-13 bispecific antibody) in, optionally, the specified amounts, as well as any product which results, directly or indirectly, from the combination of the specified ingredients in, optionally, the specified amounts.

The terms "constant region" or "constant domain" refer to a carboxy terminal portion of the light and heavy chain which is not directly involved in binding of the antibody to antigen but exhibits various effector functions, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

The term "disorder" refers to any condition that would benefit from treatment with the formulation of the present invention. This includes chronic and acute disorders or diseases including those pathological conditions which predispose the mammal, and in particular humans, to the disorder in question. Non-limiting examples of disorders to be treated herein include cancers, inflammation, autoimmune diseases, infections, cardiovascular diseases, respiratory diseases, neurological diseases and metabolic diseases.

The term "epitope" refers to a localized region on the surface of an antigen, such as an IL-4 or IL-13 polypeptide or IL-4 or IL-13 polypeptide fragment, that is capable of being bound to one or more antigen binding regions of a binding agent, such as an antibody, and that has antigenic or immunogenic activity in an animal, preferably a mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds, as determined by any method well known in the art, for example, such as an immunoassay. Antigenic epitopes need not necessarily be immunogenic. Epitopes usually consist of chemically active surface groupings of molecules, such as amino acids or sugar side chains, and have specific three dimensional structural characteristics, as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, an IL-4 or IL-13 epitope is a three-dimensional surface feature of an IL-4 or IL-13 polypeptide. In other embodiments, an IL-4 or IL-13 epitope is a linear feature of an IL-4 or IL-13 polypeptide. Anti-IL-4/anti-IL-13 bispecific antibodies may specifically bind to an epitope of the denatured form of IL-4 or IL-13, an epitope of the native form of IL-4 or IL-13, or both the denatured form and the native form of IL-4 or IL-13.

The term "excipients" refers to inert substances that are commonly used as a diluent, vehicle, preservative, binder, stabilizing agent, etc. for drugs and includes, but is not limited to, proteins (e.g., serum albumin, etc), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, hIL-4 or hIL-13 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of an IL-4 or IL-13 polypeptide or an antibody that specifically binds to an IL-4 or IL-13 polypeptide.

The phrases and terms "functional fragment, variant, derivative or analog" and the like, as well as forms thereof, of an antibody or antigen is a compound or molecule having qualitative biological activity in common with a full-length antibody or antigen of interest. For example, a functional fragment or analog of an anti-IL-4 antibody is one which can bind to an IL-4 molecule or one which can prevent or substantially reduce the ability of a ligand, or an agonistic or antagonistic antibody, to bind to IL-4.

The term "heavy chain" when used in reference to an antibody refers to five distinct types, called alpha ($\alpha$), delta ($\Delta$), epsilon ($\epsilon$), gamma ($\gamma$), and mu ($\mu$), based on the amino acid sequence of the heavy chain constant domain. These distinct types of heavy chains are well known in the art and give rise to five classes of antibodies, IgA, IgD, IgE, IgG, and IgM, respectively, including four subclasses of IgG, namely IgG1, IgG1, IgG3, and IgG4. Preferably the heavy chain is a human heavy chain.

The term "hinge" or "hinge region" refers to the flexible polypeptide comprising the amino acids between the first and second constant domains of an antibody.

"Humanized" forms of non-human (e.g., murine) antibodies are chimeric immunoglobulins, immunoglobulin chains or fragments thereof (such as $F_v$, $F_{ab}$, $F_{ab'}$, $F_{(ab')2}$ or other target-binding subsequences of antibodies) which contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region ($F_c$), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to IL-4 and/or IL-13. Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. See, for example, Studnicka et al., Prot Eng 7(6) 805-814, 1994; Mol Imm 44:1986-1988, 2007; Sims et al., J Immunol 151:2296 (1993); Chothia et al., J Mol Biol 196:901 (1987); Carter et al., Proc Natl Acad Sci USA 89:4285 (1992); Presta et al., J Immunol 151:2623 (1993), WO 2006/042333 and U.S. Pat. No. 5,869,619. Alternatively, antibodies can be humanized by other techniques including CDR grafting (EPO 0 239 400; WO 91/09967; and U.S. Pat. Nos. 5,530,101 and 5,585,089), veneering or resurfacing (EPO 0 592 106; EPO 0 519 596; Padlan, 1991, Molec Imm 28(4/5):489-498; Studnicka et al., 1994, Prot Eng 7(6):805-814; and Roguska et al., 1994, PNAS 91:969-973) and chain shuffling (U.S. Pat. No. 5,565,332). Human antibodies can be made by a variety of methods known in the art including, but not limited to, phage display methods, see U.S. Pat. Nos. 4,444,887, 4,716,111, 5,545,806 and 5,814,318; and WO 98/46645, WO 98/50433, WO 98/24893, WO 98/16654, WO 96/34096, WO 96/33735 and WO 91/10741, using transgenic animals, such as rodents, using chimeric cells and so on.

"Interleukin-4" (IL-4) relates to the naturally occurring, or endogenous mammalian IL-4 proteins and to proteins having an amino acid sequence which is the same as that of a naturally occurring or endogenous corresponding mammalian IL-4 protein {e.g., recombinant proteins, synthetic proteins (i.e., produced using the methods of synthetic organic chemistry)). Accordingly, as defined herein, the term includes mature IL-4 protein, polymorphic or allelic variants, and other isoforms of an IL-4 and modified or unmodified forms of the foregoing (e.g., lipidated, glycosylated). Naturally occurring or endogenous IL-4 includes wild type proteins such as mature IL-4, polymorphic or allelic variants and other isoforms which occur naturally in mammals (e.g., humans, non-human primates). Such proteins can be recovered or isolated from a source which naturally produces IL-4, for example. These proteins and proteins having the same amino acid sequence as a naturally occurring or endogenous corresponding IL-4, are referred to by the name of the corresponding mammal. For example, where the corresponding mammal is a human, the protein is designated as a human IL-4. Several mutant IL-4 proteins are known in the art, such as those disclosed in WO 03/038041.

"Interleukin-13" (IL-13) refers to naturally occurring or endogenous mammalian IL-13 proteins and to proteins having an amino acid sequence which is the same as that of a naturally occurring or endogenous corresponding mammalian IL-13 protein (e.g., recombinant proteins, synthetic proteins (i.e., produced using the methods of synthetic organic chemistry)). Accordingly, as defined herein, the term includes mature IL-13 protein, polymorphic or allelic variants, and other isoforms of IL-13 (e.g., produced by alternative splicing or other cellular processes), and modified or unmodified forms of the foregoing (e.g., Hpidated, glycosylated). Naturally occurring or endogenous IL-13 include wild type proteins such as mature IL-13, polymorphic or allelic variants and other isoforms and mutant forms which occur naturally in mammals (e.g., humans, non-human primates). For example, as used herein IL-13 encompasses the human IL-13 variant in which Arg at position 110 of mature human IL-13 is replaced with Gin (position 110 of mature IL-13 corresponds to position 130 of the precursor protein) which is associated with asthma (atopic and nonatopic asthma) and other variants of IL-13. (Heinzmann et al, Hum Mol Genet. 9:549-559 (2000).) Such proteins can be recovered or isolated from a source which naturally produces IL-13, for example. These proteins and proteins having the same amino acid sequence as a naturally occurring or endogenous corresponding IL-13 are referred to by the name of the corresponding mammal. For example, where the corresponding mammal is a human, the protein is designated as a human IL-13. Several mutant IL-13 proteins are known in the art, such as those disclosed in WO 03/035847.

An "isolated" or "purified" binding agent, such as an antibody, is substantially free of cellular material or other contaminating proteins from the cell or tissue source from which the binding agent is derived, or substantially free of chemical precursors or other chemicals when chemically synthesized. For example, the language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e., culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals that are involved in the synthesis of the protein. Accordingly, such preparations of the antibody have less than about 30%, 20%, 10%, 5% (by dry weight) of chemical precursors or compounds other than the antibody of interest. In a preferred embodiment, anti-IL-4/anti-IL-13 bispecific antibodies are isolated or purified.

The term "Kabat numbering," and like terms are recognized in the art and refer to a system of numbering amino acid residues that are more variable (i.e. hypervariable) than other amino acid residues in the heavy and light chain variable regions of an antibody, or an antigen binding portion thereof (Kabat et al. (1971) Ann NY Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3.

The term "light chain" when used in reference to an antibody refers to two distinct types, called kappa (κ) of lambda (λ) based on the amino acid sequence of the constant domains. Light chain amino acid sequences are well known in the art. In preferred embodiments, the light chain is a human light chain.

The term "linker" refers to a molecule that connects the antigen binding domains of the antibody. The linker may be any kind of linker molecule. Preferably, the linker is a polypeptide. The linkers may be equal or differ from each other between and within the heavy chain polypeptide and the light chain polypeptide. Furthermore, the linker may have a length of 1, 2, 3, 4, 5, 6, 7, 8, 9, 10, 11, 12, 13, 14, 15, 16, 17, 18, 19 or 20 amino acids. A preferred peptide linker unit for the heavy chain domains as for the light chain domains is $(G4S)_2$, i.e., GGGGSGGGGS (SEQ ID NO: 6). The numbers of linker units of the heavy chain and of the light chain may be equal (symmetrical order) or differ from each other (asymmetrical order). A peptide linker is preferably long enough to provide an adequate degree of flexibility to prevent the antigen binding moieties from interfering with each others activity, for example by steric hindrance, to allow for proper protein folding and, if necessary, to allow the antibody molecules to interact with two or more, possibly widely spaced, receptors on the same cell; yet it is preferably short enough to allow the antibody moieties to remain stable in the cell. Therefore, the length, composition and/or conformation of the peptide linkers can readily be selected by one skilled in the art in order to optimize the desired properties of the polyvalent antibody.

The terms "low salt" and "low salt concentration" mean a relatively low salt concentration of 15 mM or less, including a salt concentration of 0 or no salt. The salt concentration is determined by the amount of salts and buffers in the formulation. It is preferable that the buffering system is present in the formulations in a low concentration, i.e., about 15 mM or less, in order to lower the ionic strength of the formulations. Alternatively, some preferred embodiments contain no salt and no buffer. It is also preferable that no additional salts, such as NaCl are added to the formulations, in order to keep the ionic strength of the formulations as low as possible.

The terms "manage", "managing", and "management" refer to the beneficial effects that a subject derives from a therapy (e.g., a prophylactic or therapeutic agent), which does not result in a cure of the infection. In certain embodiments, a subject is administered one or more therapies (e.g., prophylactic or therapeutic agents, such as a formulation of the invention) to "manage" an IL-4 or IL-13-mediated disease (e.g., cancers, inflammation, autoimmune diseases, infections, cardiovascular diseases, respiratory diseases, neurological diseases, and metabolic diseases), one or more symptoms thereof, so as to prevent the progression or worsening of the disease.

The term "monoclonal antibody" refers to an antibody obtained from a population of homogenous or substantially homogeneous antibodies, and each monoclonal antibody will typically recognize a single epitope on the antigen. In preferred embodiments, a "monoclonal antibody" is an antibody produced by a single hybridoma or other cell. The term "monoclonal" is not limited to any particular method for making the antibody. For example, monoclonal antibodies may be made by the hybridoma method as described in Kohler et al.; Nature, 256:495 (1975) or may be isolated from phage libraries. Other methods for the preparation of clonal cell lines and of monoclonal antibodies expressed thereby are well known in the art (see, for example, Chapter 11 in: Short Protocols in Molecular Biology, (2002) 5th Ed.; Ausubel et al., eds., John Wiley and Sons, New York).

The term "pharmaceutical composition" as used in the present invention refers to formulations of various preparations. The formulations containing therapeutically effective amounts of the antibodies are sterile liquid solutions, liquid suspensions or lyophilized versions and optionally contain stabilizers or excipients.

The term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

By "pharmaceutically acceptable excipient" is meant any inert substance that is combined with an active molecule, such as a monoclonal antibody, for preparing an agreeable or convenient dosage form. The "pharmaceutically acceptable excipient" is an excipient that is non-toxic to recipients at the dosages and concentrations employed, and is compatible with other ingredients of the formulation comprising the monoclonal antibody.

The terms "prevent", "preventing", and "prevention" refer to the total or partial inhibition of the development, recurrence, onset or spread of an IL-4 or IL-13-mediated disease and/or symptom related thereto, resulting from the administration of a therapy or combination of therapies provided herein (e.g., a combination of prophylactic or therapeutic agents, such as a formulation of the invention).

The term "prophylactic agent" refers to any agent that can totally or partially inhibit the development, recurrence, onset or spread of an IL-4 or IL-13-mediated disease and/or symptom related thereto in a subject. In certain embodiments, the term "prophylactic agent" refers to a formulation of the invention. In certain other embodiments, the term "prophylactic agent" refers to an agent other than a formulation of the invention. Preferably, a prophylactic agent is an agent that is known to be useful to or has been or is currently being used to prevent an IL-4 or IL-13-mediated disease and/or a symptom related thereto, or impede the onset, development, progression and/or severity of an IL-4 or IL-13-mediated disease and/or a symptom related thereto. In specific embodiments, the prophylactic agent is a humanized anti-IL-4/anti-IL-13 bispecific antibody.

The phrase "recombinant antibody" includes antibodies that are prepared, expressed, created, or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created, or isolated by any other means that involves splicing of human immunoglobulin gene sequences to other DNA sequences. Such recombinant antibodies can have variable and constant regions derived from immunoglobulin sequences (See Kabat, E. A. et al. (1991) Sequences of Proteins of Immunological Interest, Fifth Edition, U.S. Department of Health and Human Services, NIH Publication No. 91-3242). In certain embodiments, however, such recombinant antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to germline VH and VL sequences, may not naturally exist within the antibody germline repertoire in vivo.

The term "saccharide" refers to a class of molecules that are derivatives of polyhydric alcohols. Saccharides are commonly referred to as carbohydrates and may contain different amounts of sugar (saccharide) units, e.g., monosaccharides, disaccharides and polysaccharides.

The terms "specifically binds" or "specifically binding" mean specifically binding to an antigen or a fragment thereof and not specifically binding to other antigens. For example, an antibody that specifically binds to an antigen may bind to other peptides or polypeptides with lower affinity, as determined by, e.g., radioimmunoassays (RIA), enzyme-linked immunosorbent assays (ELISA), BIACORE, or other assays known in the art. Antibodies or variants or fragments thereof that specifically bind to an antigen may be cross-reactive with related antigens. Preferably, antibodies or variants or fragments thereof that specifically bind to an antigen do not cross-react with other antigens. An antibody or a variant or a fragment thereof that specifically binds to an IL-4 and/or IL-13 antigen can be identified, for example, by immunoassays, BIAcore, or other techniques known to those of skill in the art. Typically a specific or selective reaction will be at least twice background signal or noise, and more typically more than 10 times background. See, e.g., Paul, ed., 1989, Fundamental Immunology Second Edition, Raven Press, New York at pages 332-336 for a discussion regarding antibody specificity.

A "stable" or "stabilized" formulation is one in which the binding agent, such as an antibody, therein essentially retains its physical stability, identity, integrity, and/or chemical stability, identity, integrity, and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993), for example. Stability can be measured at a selected temperature and other storage conditions for a selected time period. The stability may be determined by at least one of the methods selected from the group consisting of visual inspection, SDS-PAGE, IEF, HPSEC, RFFIT, and kappa/lambda ELISA. For example, an antibody "retains its physical stability" in a pharmaceutical formulation, if it shows no signs of aggregation, precipitation, and/or denaturation upon visual examination of color and/or clarity, or as measured by UV light scattering, SDS-PAGE, or by (high pressure) size exclusion chromatography (HPSEC). Preferably, when using the formulations of the invention, 5% or less, typically 4% or less, preferably 3% or less, more preferably 2% or less, and particularly 1% or less of the antibodies forms aggregates, as measured by HPSEC or any other suitable method for measuring aggregation formation. For example, an antibody is considered stable in a particular formulation if the antibody monomer has a purity of about 90%, preferably about 95%, in particular about 98% after a certain predetermined period of time under certain storage conditions in a particular formulation. Chemical stability can be assessed by detecting and quantifying chemically altered forms of the protein. Chemical alteration may involve size modification (e.g., clipping), which can be evaluated using (HP)SEC, SDS-PAGE, and/or matrix-assisted laser desorption ionization/time-of-flight mass spectrometry (MALDI/TOF MS), for example. Other types of chemical alteration include charge alteration (e.g., occurring as a result of deamidation), which can be evaluated by ion-exchange chromatography, for example. An antibody "retains its biological activity" in a pharmaceutical formulation at a given time, if the biological activity of the antibody at a given time is at least about 90% (within the errors of the assay) of the biological activity exhibited at the time the pharmaceutical formulation was prepared, as determined in an antigen binding assay or virus neutralizing assay, for example.

The terms "subject" and "patient" are used interchangeably. As used herein, a subject is preferably a mammal, such as a non-primate (e.g., cows, pigs, horses, cats, dogs, rats, etc.) or a primate (e.g., monkey and human), most preferably a human. In one embodiment, the subject is a mammal, preferably a human, having an IL-4 and/or IL-13-mediated disease. In another embodiment, the subject is a mammal, preferably a human, at risk of developing an IL-4 and/or IL-13-mediated disease.

The phrase "substantially identical" with respect to an antibody chain polypeptide sequence may be construed as an antibody chain exhibiting at least 70%, 80%, 90%, 95% or more sequence identity to the reference polypeptide sequence. The term with respect to a nucleic acid sequence may be construed as a sequence of nucleotides exhibiting at least about 85%, 90%, 95%, or 97% or more sequence identity to the reference nucleic acid sequence.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion. "Insertional" variants are those with one or more amino acids inserted immediately adjacent to an amino acid at a particular position in a native sequence Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

The term "therapeutically effective amount" refers to the amount of a therapy (e.g., a formulation of the invention) that is sufficient to reduce and/or ameliorate the severity and/or duration of a given disease and/or a symptom related thereto. This term also encompasses an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than a formulation of the invention). In some embodiments, the therapeutically effective amount of an antibody of the invention provides a local concentration of between about 5 and 20 ng/ml, and preferably, between about 10 and 20 ng/ml. In some embodiments, "therapeutically effective amount" as used herein also refers to the amount of an antibody of the invention to achieve a specified result (e.g., inhibition of an IL-4 and/or IL-13 cytokine).

The term "therapeutic agent" refers to any agent that can be used in the treatment, management or amelioration of an IL-4 and/or IL-13-mediated disease and/or a symptom related thereto. In certain embodiments, the term "therapeutic agent" refers to a formulation of the invention. In certain other embodiments, the term "therapeutic agent" refers to an agent other than a formulation of the invention. Preferably, a therapeutic agent is an agent that is known to be useful for, or has been or is currently being used for the treatment, management or amelioration of an IL-4 and/or IL-13-mediated disease or one or more symptoms related thereto.

The term "therapy" refers to any protocol, method, and/or agent that can be used in the prevention, management, treatment, and/or amelioration of an IL-4 and/or IL-13-mediated disease (e.g., cancers, inflammation, autoimmune diseases, infections, cardiovascular diseases, respiratory diseases, neurological diseases, and metabolic diseases). In certain embodiments, the terms "therapies" and "therapy" refer to a biological therapy, supportive therapy, and/or other therapies useful in the prevention, management, treatment, and/or amelioration of an IL-4 and/or IL-13-mediated disease known to one of skill in the art, such as medical personnel.

The terms "treat", "treatment", and "treating" refer to the reduction or amelioration of the progression, severity, and/or duration of an IL-4 and/or IL-13-mediated disease (e.g., cancers, inflammation, autoimmune diseases, infections, cardiovascular diseases, respiratory diseases, neurological diseases, and metabolic diseases) resulting from the administration of one or more therapies (including, but not limited to, the administration of one or more prophylactic or therapeutic agents, such as a formulation of the invention).

The terms "variable region" or "variable domain" refer to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complementarity determining regions (CDRs), while the more highly conserved regions in the variable domain are called framework regions (FR). The CDRs of the light and heavy chains are primarily responsible for the interaction of the antibody with antigen. Numbering of amino acid positions is according to the EU Index, as in Kabat et al. (1991) Sequences of proteins of immunological interest. (U.S. Department of Health and Human Services, Washington, D.C.) 5th ed. ("Kabat et al."). In preferred embodiments, the variable region is a human variable region.

B. Formulations and Formulation Components

As stated previously, the formulations of the invention comprise an anti-IL-4/anti-IL-13 bispecific antibody and a buffering system, wherein the pH of the formulation is about pH 7, and wherein the formulation has a low salt concentration in order to reduce the ionic strength of the formulation. The formulations may, optionally, further comprise a non-ionic surfactant, a sugar, and/or a non-ionic stabilizing agent. The formulations of the invention have been found to provide significant improvements over prior anti-IL-4/anti-IL-13 bispecific antibody formulations, which often lead to molecular aggregation of the antibody upon increasing the concentration of the antibody in the formulation, and the formation of visible and sub-visible particles. In particular, the formulations of the invention exhibit good stability regarding visible particles, sub-visible particles, low molecular weight proteins, and high molecular weight proteins.

i. Anti-IL-4/Anti-IL-13 Bispecific Antibodies, and Variants and Fragments Thereof In certain embodiments, the formulations of the invention include an anti-IL-4/anti-IL-13 bispecific antibody. The bispecific antibody binds or specifically binds to IL-4 and/or IL-13, or variants or fragments thereof. The IL-4 and/or IL-13 molecules may be from any species. Preferably, the IL-4 and/or IL-13 molecules are from a human. The amino acid sequences and protein structures of both IL-4 and IL-13 are well known in the art.

In certain exemplary embodiments, the anti-IL-4/anti-IL-13 bispecific antibody is a humanized antibody, a fully human antibody, or a variant thereof or an antigen-binding fragment thereof. Preferred anti-IL-4/anti-IL-13 bispecific antibodies prevent binding of IL-4 and IL-13 with their receptors, and inhibit IL-4 and IL-13 biological activity.

In a specific embodiment, the anti-IL-4/anti-IL-13 bispecific antibody or antigen binding fragment thereof comprises a light chain variable region (VL) that binds to IL-13 comprising the amino acid sequence of SEQ ID NO: 1 (Underline indicates amino acid changes made. Bold indicates the CDRs; CDR1 is SEQ ID NO: 7 RASESVDSYGQSYMH; CDR2 is SEQ ID NO: 8 LASNLES; and CDR3 is SEQ ID NO: 9 QQNAEDSRT).

```
Anti-IL13 hB-B13 VL3 (SEQ ID NO: 1):
DIVLTQSPAS LAVSLGQRAT ISCRASESVD SYGQSYMHWY
QQKAGQPPKL LIYLASNLES GVPARFSGSG SRTDFTLTID
PVQAEDAATY YCQQNAEDSR TFGGGTKLEI K
```

In a specific embodiment, the anti-IL-4/anti-IL-13 bispecific antibody or antigen binding fragment thereof comprises a heavy chain variable region (VH) that binds to IL-13 comprising the amino acid sequence of SEQ ID NO: 2 (Underline indicates amino acid changes made. Bold indicates the CDRs; CDR1 is SEQ ID NO: 10 GFSLTDSSIN; CDR2 is SEQ ID NO: 11 DGRID; and CDR3 is SEQ ID NO: 12 DGYFPYAMDF).

```
Anti-IL13 hB-B13 VH2 (SEQ ID NO: 2):
EVQLKESGPG LVAPGGSLSI TCTVSGFSLT DSSINWVRQP
PGKGLEWLGM IWGDGRIDYA DALKSRLSIS KDSSKSQVFL
EMTSLRTDDT ATYYCARDGY FPYAMDFWGQ GTSVTVSS
```

In a specific embodiment, the anti-IL-4/anti-IL-13 bispecific antibody or antigen binding fragment thereof comprises a light chain variable region (VL) that binds to IL-4 comprising the amino acid sequence of SEQ ID NO: 3 (Underline indicates amino acid changes made. Bold indicates the CDRs; CDR1 is SEQ ID NO: 13 HASQNIDVWLS; CDR2 is SEQ ID NO: 14 KASNLHTG; CDR3 is SEQ ID NO: 15 QQAHSYPFT).

```
Anti-IL4 h8D4-8 VL1 (SEQ ID NO: 3):
DIQMTQSPAS LSVSVGDTIT LTCHASQNID VWLSWFQQKP
GNIPKLLIYK ASNLHTGVPS RFSGSGSGTG FTLTISSLQP
EDIATYYCQQ AHSYPFTFGG GTKLEIKR
```

In a specific embodiment, the anti-IL-4/anti-IL-13 bispecific antibody or antigen binding fragment thereof comprises a heavy chain variable region (VH) that binds to IL-4 comprising the amino acid sequence of SEQ ID NO: 4 (Underline indicates amino acid changes made. Bold indicates the CDRs; CDR 1 is SEQ ID NO: 16 GYSFTSYWIH; CDR2 is SEQ ID NO: 17 IDPSDGETR; and CDR3 is SEQ ID NO: 18 LKEYGNYDSFYFDV).

```
Anti-IL4 h8D4-8 VH1 (SEQ ID NO: 4):
QVQLQQSGPE LVKPGASVKI SCKASGYSFT SYWIHWIKQR
PGQGLEWIGM IDPSDGETRL NQRFQGRATL TVDESTSTAY
MQLRSPTSED SAVYYCTRLK EYGNYDSFYF DVWGAGTLVT VSSA
```

In another specific embodiment, the anti-IL-4/anti-IL-13 bispecific antibody or antigen binding fragment thereof comprises a heavy chain variable region (VH) that binds to IL-4 comprising the amino acid sequence of SEQ ID NO: 5 (Underline indicates amino acid changes made. Bold indicates the CDRs; CDR 1 is SEQ ID NO: 19 GYSFTSYWIH; CDR2 is SEQ ID NO: 20 IDASDGETR; and CDR3 is SEQ ID NO: 21 LKEYGNYDSFYFDV).

```
Anti-IL4 h8D4-8 VH2 (SEQ ID NO: 5):
QVQLQQSGPE LVKPGASVKI SCKASGYSFT SYWIHWIKQR
PGQGLEWIGM IDASDGETRL NQRFQGRATL TVDESTSTAY
MQLRSPTSED SAVYYCTRLK EYGNYDSFYF DVWGAGTLVT VSSA
```

In some specific embodiments, the anti-IL-4/anti-IL-13 bispecific antibody or antigen binding fragment thereof comprises a heavy chain variable region that binds to IL-13 comprising the amino acid sequence of SEQ ID NO: 2; and a light chain variable region that binds to IL-13 comprising the amino acid sequence of SEQ ID NO: 1.

In other specific embodiments, the anti-IL-4/anti-IL-13 bispecific antibody or antigen binding fragment thereof comprises a heavy chain variable region that binds to IL-4 comprising the amino acid sequence of SEQ ID NO: 4; and a light chain variable region that binds to IL-4 comprising the amino acid sequence of SEQ ID NO: 3.

In still other specific embodiments, the anti-IL-4/anti-IL-13 bispecific antibody or antigen binding fragment thereof comprises a heavy chain variable region that binds to IL-4 comprising the amino acid sequence of SEQ ID NO: 5; and a light chain variable region that binds to IL-4 comprising the amino acid sequence of SEQ ID NO: 3.

In more specific embodiments, the anti-IL-4/anti-IL-13 bispecific antibody or antigen binding fragment thereof comprises a heavy chain variable region that binds to both IL-13 and IL-4 comprising the amino acid sequences of SEQ ID NOs: 2 and 4, or 2 and 5; and a light chain variable region that binds to both IL-13 and IL-4 comprising the amino acid sequences of SEQ ID NOs: 1 and 3.

In a most specific embodiment, the anti-IL-4/anti-IL-13 bispecific antibody comprises a heavy chain variable region that binds to both IL-13 and IL-4 comprising the amino acid sequences of SEQ ID NOs: 2 and 4; and a light chain variable region that binds to both IL-13 and IL-4 comprising the amino acid sequences of SEQ ID NOs: 1 and 3 (the "Lead Antibody"). A schematic drawing of an embodiment of the anti-IL-4/anti-IL-13 bispecific antibody is shown in FIG. 1, and exemplary heavy and light chain variable regions are shown in FIG. 2. The molecular weight of the Lead Antibody, as determined by mass spectrometry is 198 kDa. The isoelectric point of the Lead Antibody, as determined by isoelectric focusing, ranges between 5.8 and 6.2.

In alternative most specific embodiments, the anti-IL-4/anti-IL-13 bispecific antibody or an antigen binding fragment thereof comprises a light chain of the formula VL1-linker-VL2 and a heavy chain of the formula VH1-linker-VH2, wherein VL1 and VH1 form an IL-4 antigen binding domain and VL2 and VH2 form an IL-13 antigen binding domain. In some embodiments, VL1 comprises the CDR sequences of SEQ ID NO: 1; VH1 comprises the CDR sequences of SEQ ID NO: 2; VL2 comprises the CDR sequences of SEQ ID NO: 3; and VH2 comprises the CDR sequences of SEQ ID NO: 4 or 5. In alternative embodiments, VL2 comprises the amino acid sequence of SEQ ID NO: 1; VH2 comprises the amino acid sequence of SEQ ID NO: 2; VL1 comprises the amino acid sequence of SEQ ID NO: 3; and VH1 comprises the amino acid sequence of SEQ ID NO: 4 or 5.

In some embodiments, the anti-IL-4/anti-IL-13 bispecific antibody or antigen binding fragment thereof comprises a linker between the antigen binding domains of the antibody. The linker may be any kind of linker molecule. Preferably, the linker is a polypeptide. The linkers may be equal or differ from each other between and within the heavy chain polypeptide and the light chain polypeptide. Furthermore, the linker may have a length of 1, 2, 3, 4, 5, 6, 7, 8, 9, 10, 11, 12, 13, 14, 15, 16, 17, 18, 19 or 20 amino acids. A preferred peptide linker unit for the heavy chain domains as for the light chain domains is $(G4S)_2$, i.e., GGGGSGGGGS (SEQ ID NO: 6). Most preferably, SEQ ID NOs: 2 and 4 are linked together by a first peptide linker, and SEQ ID NOs: 1 and 3 are linked together by a second peptide, wherein the first and second peptide linkers each comprise the amino acid sequence of SEQ ID NO: 6. The numbers of linker units of the heavy chain and of the light chain may be equal (symmetrical order) or differ from each other (asymmetrical order). A peptide linker is preferably long enough to provide an adequate degree of flexibility to prevent the antigen binding moieties from interfering with each others activity, for example by steric hindrance, to allow for proper protein folding and, if necessary, to allow the antibody molecules to interact with two or more, possibly widely spaced, receptors on the same cell; yet it is preferably short enough to allow the antibody moieties to remain stable in the cell. Therefore, the length, composition and/or conformation of the peptide linkers can readily be selected by one skilled in the art in order to optimize the desired properties of the polyvalent antibody.

In a preferred embodiment of the invention, the anti-IL-4/anti-IL-13 bispecific antibody or antigen binding fragment thereof is a humanized antibody. Examples of humanized antibody isotypes include IgA, IgD, IgE, IgG, and IgM. Preferably, the anti-IL-4/anti-IL-13 bispecific antibody is an IgG antibody. There are four forms of IgG. Preferably, the anti-IL-4/anti-IL-13 bispecific antibody is an IgG4 antibody. In a more preferred embodiment of the invention, the anti-IL-4/anti-IL-13 bispecific antibody is a humanized IgG4 antibody.

In some embodiments, the anti-IL-4/anti-IL-13 bispecific antibody or antigen binding fragment thereof further comprises a constant region, e.g., CH1, CH2, CH3, and CL.

Certain embodiments of formulations of the invention also include variants of anti-IL-4/anti-IL-13 bispecific antibodies or antigen binding fragments thereof. Variants of anti-IL-4/anti-IL-13 bispecific antibodies may have similar physicochemical properties based on their high similarity, and therefore are also included within the scope of the invention. Variants are defined as antibodies with an amino acid sequence that is at least 95%, preferably at least 97%, for instance at least 98% or 99% homologous to anti-IL-4/anti-IL-13 bispecific antibodies, and capable of competing for binding to an IL-4 and/or IL-13 polypeptide, an IL-4 and/or IL-13 polypeptide fragment, or an IL-4 and/or IL-13 epitope. Preferably, the variants will ameliorate, neutralize, or otherwise inhibit IL-4 and/or IL-13 biological activity. Determining competition for binding to the target can be done by routine methods known to the skilled person in the art. Preferably the variants are human or humanized antibodies, and preferably are IgG4 molecules. In preferred embodiments, a variant is at least 95%, 96%, 97%, 98%, or 99% identical in amino acid sequence with a heavy chain variable region that binds to both IL-13 and IL-4 comprising the amino acid sequences of SEQ ID NOs: 2, 4, and 5; and a light chain variable region that binds to both IL-13 and IL-4 comprising the amino acid sequences of SEQ ID NOs: 1 and 3. The term "variant" refers to an antibody that comprises an amino acid sequence that is altered by one or more amino acids compared to the amino acid sequences of the anti-IL-4/anti-IL-13 bispecific antibody. The variant may have conservative sequence modifications, including amino acid substitutions, modifications, additions, and deletions.

Examples of modifications include, but are not limited to, glycosylation, acetylation, pegylation, phosphorylation, amidation, derivatization by known protecting/blocking groups, proteolytic cleavage, and linkage to a cellular ligand or other protein. Amino acid modifications can be introduced by standard techniques known in the art, such as site-directed mutagenesis, molecular cloning, oligonucleotide-directed mutagenesis, and random PCR-mediated mutagenesis in the nucleic acid encoding the antibodies. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine), and aromatic side chains (e.g., tyrosine, phenylalanine, tryptophan). It will be clear to the skilled artisan that classifications of amino acid residue families other than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, modified, inserted, or deleted without abolishing immunological activity may be found using computer programs well known in the art. Computer algorithms, such as, inter alia, Gap or Bestfit, which are known to a person skilled in the art, can be used to optimally align amino acid sequences to be compared and to define similar or identical amino acid residues. Variants may have the same or different, either higher or lower, binding affinities compared to an anti-IL-4/anti-IL-13 bispecific antibody, but are still capable of specifically binding to IL-4 and/or IL-13, and may have the same, higher or lower, biological activity as the anti-IL-4/anti-IL-13 bispecific antibody.

Embodiments of the invention also include antigen binding fragments of the anti-IL-4/anti-IL-13 bispecific antibodies. The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the complementary determining regions (CDR)). The antigen binding region can be derived from any animal species, such as rodents (e.g., rabbit, rat or hamster) and humans. Preferably, the antigen binding region will be of human origin. Non-limiting examples of antigen binding fragments include: Fab fragments, F(ab')2 fragments, Fd fragments, Fv fragments, single chain Fv (scFv) molecules, dAb fragments, and minimal recognition units consisting of the amino acid residues that mimic the hypervariable region of the antibody.

In preferred embodiments of the invention, the anti-IL-4/anti-IL-13 bispecific antibody (or a variant thereof or an antigen binding fragment thereof) will ameliorate, neutralize, or otherwise inhibit IL-4 and/or IL-13 biological activity in vivo.

In preferred embodiments of the invention, the anti-IL-4/anti-IL-13 bispecific antibodies (or a variant thereof or an antigen binding fragment thereof) are antagonist antibodies that ameliorate, neutralize, or otherwise inhibit IL-4 and/or IL-13 biological activity in vivo.

Identification, isolation, preparation, and characterization of anti-IL-4/anti-IL-13 bispecific antibodies or variants or fragments thereof that bind to both IL-13 and IL-4, including the anti-IL-4/anti-IL-13 bispecific antibody comprising a heavy chain variable region comprising the amino acid sequences of SEQ ID NOs: 2 and 4, and a light chain variable region comprising the amino acid sequences of SEQ ID NOs: 1 and 3, have been described in detail in PCT Publication WO 2009/052081, which is incorporated herein by reference.

Preferably, the anti-IL-4/anti-IL-13 bispecific antibodies (or a variant thereof or an antigen binding fragment thereof) are present in the formulations in an amount from about 5 mg/mL to about 200 mg/mL, e.g., about 50 mg/mL to about 150 mg/mL, about 75 mg/mL to about 125 mg/mL, and about 100 mg/mL. Alternatively, the anti-IL-4/anti-IL-13 bispecific antibodies (or a variant thereof or an antigen binding fragment thereof) are present in the formulations in an amount from about 5 mg/mL to about 65 mg/mL, about 66 mg/mL to about 130 mg/mL, about 131 mg/mL to about 200 mg/mL. For example, the anti-IL-4/anti-IL-13 bispecific antibody may be present in the formulation in an amount of about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, or about 200 mg/mL.

In certain exemplary embodiments, the anti-IL-4/anti-IL-13 bispecific antibody is present in the formulation in an amount of about 100 mg/mL. In another exemplary embodiment, a humanized IgG4 anti-IL-4/anti-IL-13 bispecific antibody comprising a heavy chain variable region that binds to both IL-13 and IL-4 comprising the amino acid sequences of SEQ ID NOs: 2 and 4, or 2 and 5; and a light chain variable region that binds to both IL-13 and IL-4 comprising the amino acid sequences of SEQ ID NOs: 1 and 3 is present in the formulation in an amount of about 100 mg/mL.

ii. Buffering Agents, Buffering Systems, Ionic Strength, and pH

Buffering agents help to maintain the pH of the formulations in a range that approximates physiological conditions. Buffers are preferably present in the formulations at a concentration ranging from about 1 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid-monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts such as Tris, HEPES and other such known buffers are also suitable and can be used. Preferably, a combination of buffers, i.e., two or more buffering agents, is used in the formulations of the present invention. A combination of two or more buffers is referred to herein as a buffering system.

The formulations of the invention comprise a buffering system. A buffering system maintains a physiologically suitable pH. In addition, a buffering system participates in achieving isotonicity and chemical stability of the formulation. Due to the difficulty of developing a stable antibody formulation for the bispecific antibody, it is preferable to use a combined buffering system in order to take advantage of the benefits of two or more buffers. By combining the benefits of two or more buffers, a more stable antibody formulation is able to be developed.

Preferably, the buffering system is present in the formulations at a concentration from about 1 mM to about 50 mM, e.g., about 5 mM to about 25 mM, about 5 mM to about 15 mM, or about 10 mM. Alternatively, the buffering system is present in the formulations at a concentration from about 1 mM to about 15 mM, about 16 to about 30 mM, about 31 to about 45 mM, or about 46 mM to about 50 mM. For example, the buffering system may be present in the formulation at a concentration of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, and about 50 mM. More preferably, the buffering system is present in the formulation at a concentration from about 5 mM to about 15 mM, and even more preferably from about 8 mM to about 12 mM. In a most preferred embodiment, the buffering system is present at a concentration of about 10 mM.

Preferably, the buffering system comprises a Tris buffer and a phosphate buffer. Preferably, the Tris buffer is present in the formulations at a concentration from about 1 to about 5 mM. For example, the Tris buffer may be present in the formulation at a concentration of about 1 mM, about 2 mM, about 3 mM, about 4 mM, or about 5 mM. More preferably, the Tris buffer is present in the formulations at a concentration from about 2 mM to about 4 mM, and even more preferably from about 3 mM to about 4 mM. In a most preferred embodiment, the Tris buffer is present at a concentration of about 3.7 mM.

Preferably, the phosphate buffer is present in the formulations at a concentration from about 1 to about 10 mM. For example, the phosphate buffer may be present in the formulations at a concentration of about 1 mM, about 2 mM, about 3 mM, about 4 mM, about 5 mM, about 6 mM, about 7 mM, about 8 mM, about 9 mM, or about 10 mM. More preferably, the phosphate buffer is present in the formulations at a concentration from about 3 mM to about 8 mM, and even more preferably from about 5 mM to about 7 mM. In a most preferred embodiment, the phosphate buffer is present at a concentration of about 6.3 mM.

In a most preferred embodiment of the invention, the buffering system comprises a Tris buffer at a concentration of about 3.7 mM and a phosphate buffer at a concentration of about 6.3 mM. This combination of Tris buffer and phosphate buffer in a buffer system is highly unusual and is not known in the art.

It is also preferable that the buffering system is present in the formulations in a low concentration, i.e., about 15 mM or less, in order to lower the ionic strength of the formulation. This is due to the fact that as the ionic strength of the formulation increases, the kinetics of aggregation of the antibody increases. Decreasing aggregation of the antibody and/or the speed of aggregation of the antibody is needed in order to improve the stability of the formulation.

In certain embodiments, the formulations of the invention have a pH around pH 7. Preferably, the pH of the formulations range from about 5.0 to about 8.0. For example, the pH of the formulations may be about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, and about 8.0. More preferably, the pH of the formulations may range from about 6.5 to about 7.5. In a most preferred embodiment, the pH is about 7.0. The formulations exhibit good stability regarding visible particles, sub-visible particles, low molecular weight proteins, and high molecular weight proteins when the pH of the formulations is about pH 7. The pH of the formulation may be measured by any means known to those of skill in the art. A preferred means for measuring pH is using a pH meter with a micro-electrode. The pH of the formulation may be adjusted using any means known in the art. Preferred chemicals for altering the pH of the formulations are hydrochloric acid (HCl) and sodium hydroxide (NaOH).

In certain embodiments, the formulations of the invention have a pH above the isoelectric point (pI) of the antibody. The isoelectric point is the pH at which a particular molecule or surface carries no net electrical charge. The pI of the bispecific antibody may be determined by any means known to those of skill in the art. Preferably, the pI of the bispecific antibody is determined by denaturated isoelectric focusing. The pI of the anti-IL-4/anti-IL-13 bispecific antibody comprising a heavy chain variable region comprising the amino acid sequences of SEQ ID NOs: 2 and 4; and a light chain variable region comprising the amino acid sequences of SEQ ID NOs: 1 and 3 is 5.8-6.2.

iii. Non-Ionic Surfactants

The formulations of the invention may, optionally, further comprise a non-ionic surfactant. Surfactants are chemical compounds that stabilize biological molecules and/or general pharmaceutical excipients in a formulation. Surfactants generally protect the molecules and excipients from air/solution interface induced stresses and solution/surface induced stresses, which may otherwise result in the aggregation of molecules. Surfactants also prevent visible and sub-visible particle formation.

Preferably, the non-ionic surfactant is present in the formulations at a concentration from about 0.01% to about 1% (w/v), e.g., about 0.01% to about 0.5%, about 0.01% to about 0.3%, or about 0.01% to about 0.2%. Alternatively, the non-ionic surfactant is present in the formulations at a concentration from about 0.01% to about 0.05% (w/v), about 0.06% to about 0.10% (w/v), about 0.11% to about 0.15% (w/v), about 0.16% to about 0.20% (w/v), about 0.20% to about 0.30% (w/v), about 0.30% to about 0.40% (w/v), about 0.40% to about 0.50% (w/v), about 0.50% to about 0.60% (w/v), about 0.60% to about 0.70% (w/v), about 0.70% to about 0.80% (w/v), about 0.80% to about 0.90% (w/v), or about 0.90% to about 1.0% (w/v). For example, the non-ionic surfactant may be present in the formulations in an amount of about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), and about 1% (w/v). In particular embodiments, the non-ionic surfactant is present in the formulations from about 0.05% to about 0.2% (w/v).

Examples of surfactants include, but are not limited to, polysorbates, glycerin, dicarboxylic acids, oxalic acid, succinic acid, fumaric acids, phthalic acids, and combinations thereof. Those skilled in the art are aware that other non-ionic surfactants can be used as long as they are pharmaceutically acceptable, i.e. suitable for administration to subjects. The non-ionic surfactant is preferably a polysorbate. Examples of polysorbates include polysorbate 20, polysorbate 40, polysorbate 60, polysorbate 65, and polysorbate 80. Most preferably, the non-ionic surfactant is polysorbate 80.

In exemplary embodiments, polysorbate 80 is present in the formulations in an amount from about 0.01% to about 1% (w/v). For example, polysorbate 80 may be present in the formulations in an amount of about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), and about 1% (w/v). In particular embodiments, polysorbate 80 is present in the formulations from about 0.03% to about 0.2% (w/v). For example, polysorbate 80 may be present in an amount from about 0.01% to about 1% (w/v), about 0.02% to about 0.5% (w/v), and about 0.03% to about 0.2% (w/v). In most preferred embodiments of the invention, polysorbate 80 is present in the formulations in an amount of 0.2% (w/v).

iv. Sugars

The formulations of the invention may, optionally, further comprise a sugar. Typically, sugars are used as a stabilizing agent for high molecular weight proteins or as a cryoprotectant or as lyoprotectant.

Preferably, the sugar is present in the formulations at a concentration from about 1% to about 10% (w/v), e.g., about 2% to about 8% (w/v), about 3% to about 7% (w/v), about 4% to about 6% (w/v), or about 5% (w/v). Alternatively, the sugar is present in the formulations at a concentration from about 1% to about 3% (w/v), about 3% to about 6% (w/v), or about 6% to about 10% (w/v). For example, the sugar may be present in the formulations in an amount of about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v). In particular embodiments, the sugar is present in the formulations from about 3% to about 7% (w/v), and more preferably about 5%.

Examples of sugars include, but are not limited to, monosaccharides, disaccharides, and polysaccharides. Examples of saccharides include glucose, sucrose, maltose, trehalose, dextrose, xylitol, fructose and mannitol. Those skilled in the art are aware that other sugars can be used as long as they are pharmaceutically acceptable, i.e. suitable for administration to subjects. Preferably, the sugar is a disaccharide. More preferably, the sugar is sucrose.

In certain embodiments, sucrose is present in the formulations in an amount from about 1% to 10% (w/v). For example, sucrose may be present in the formulation in an amount of about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v). Preferably, sucrose may be present in an amount of about 3% to about 7% (w/v), or about 4% to about 6% (w/v). Most preferably, sucrose is present in the formulations in an amount of about 5% (w/v).

v. Non-Ionic Stabilizing Agents

The formulations of the invention may, optionally, further comprise a non-ionic stabilizing agent. Stabilizing agents refer to a broad category of excipients that can range in function from a bulking agent to an additive that solubilizes the therapeutic agent or helps to prevent denaturation or adherence to the container wall. Stabilizing agents also minimize high molecular weight protein formation.

Preferably, the non-ionic stabilizing agent is present in the formulations at a concentration from about 1% to about 10% (w/v), e.g., about 2% to about 8% (w/v), about 2% to about 5% (w/v), about 2% to about 4% (w/v), or about 3% (w/v). Alternatively, the non-ionic stabilizing agent is present in the formulations at a concentration from about 1% to about 2% (w/v), about 2% to about 4% (w/v), about 4% to about 6% (w/v), about 6% to about 8% (w/v), or about 8% to about 10% (w/v). For example, the non-ionic stabilizing agent may be present in the formulations in an amount of about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v). In particular embodiments, the non-ionic stabilizing agent is present in the formulations from about 1% to about 5% (w/v), more preferably from about 1% to about 3% (w/v), and most preferably about 3% (w/v).

Examples of stabilizing agents include, but are not limited to, polyhydric sugar alcohols; amino acids, such as proline, arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose, glucose; disaccharides, such as lactose, maltose and sucrose; trisaccharides such as raffinose; polysaccharides such as dextran and so on. Those skilled in the art are aware that other non-ionic stabilizing agents can be used as long as they are pharmaceutically acceptable, i.e. suitable for administration to subjects. Preferably, the non-ionic stabilizing agent is an amino acid. More preferably, the non-ionic stabilizing agent is proline or glycine. Most preferably, the non-ionic stabilizing agent is proline. Alternatively, the non-ionic stabilizing agent is mannitol.

In certain embodiments, proline is present in the formulations in an amount from about 1% to 10% (w/v). For example, proline may be present in the formulation in an amount of about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v). Preferably, proline may be present in an amount of about 1% to about 5% (w/v), or about 1% to about 3% (w/v). Most preferably, proline is present in the formulations in an amount of about 3% (w/v).

In certain alternative embodiments, mannitol is present in the formulations in an amount from about 1% to 10% (w/v). For example, mannitol may be present in the formulation in an amount of about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v). Preferably, mannitol may be present in an amount of about 1% to about 5% (w/v), or about 1% to about 3% (w/v). Most preferably, mannitol is present in the formulations in an amount of about 3% (w/v).

v. Other Excipients

Furthermore, the formulations of the invention may, optionally, further comprise other excipients including, but not limited to, water for injection, diluents, solubilizing agents, soothing agents, additional buffers, inorganic or organic salts, antioxidants, preservatives, bulking agents, chelating agents, tonicity agents, or the like. Preferably, however, the formulations of the invention comprise no other excipients, except those described above. Other pharmaceutically acceptable carriers, excipients, or stabilizers, such as those described in Remington's Pharmaceutical Sciences 16$^{th}$ edition, Osol, A. Ed. (1980) may be included in the formulation provided that they do not adversely affect the desired characteristics of the formulation. In a particular embodiment, the formulation is substantially free of preservatives, although, in alternative embodiments, preservatives may be added as necessary. For example, cryoprotectants or lyoprotectants may be included in lyophilized formulations.

vi. Liquid or Lyophilized Formulations

The formulations of the invention may either be liquid formulations or lyophilized formulations. Preferably, the formulations are liquid formulations. More preferably, the liquid formulations are ready for injection. Alternatively, the formulations may be lyophilized powders. Preferably, the lyophilized powders are ready to be combined with a solvent just prior to administration.

vii. Exemplary Formulations

In one exemplary embodiment of the invention, the invention provides a liquid antibody formulation suitable for subcutaneous administration, the formulation comprising:

about 100 mg/mL of a bispecific antibody or an antigen binding fragment thereof, wherein the antibody or antigen binding fragment thereof comprises a heavy chain variable region comprising the amino acid sequences of SEQ ID NOs: 2 and 4, and a light chain variable region comprising the amino acid sequences of SEQ ID NOs: 1 and 3;

about 10 mM of a buffering system, wherein the buffering system comprises a Tris buffer concentration of about 3.7 mM and a Phosphate buffer concentration of about 6.3 mM;

about 0.2% (w/v) polysorbate 80;

about 5% (w/v) sucrose; and about 3% (w/v) proline;

wherein the pH of the formulation is about pH 7.

In another exemplary embodiment of the invention, the invention provides a liquid antibody formulation suitable for subcutaneous administration, the formulation comprising:

about 100 mg/mL of a bispecific antibody or an antigen binding fragment thereof, wherein the antibody or antigen binding fragment thereof comprises a heavy chain variable region comprising the amino acid sequences of SEQ ID NOs: 2 and 4, and a light chain variable region comprising the amino acid sequences of SEQ ID NOs: 1 and 3;

about 10 mM of a buffering system, wherein the buffering system comprises a Tris buffer concentration of about 3.7 mM and a Phosphate buffer concentration of about 6.3 mM;

about 0.2% (w/v) polysorbate 80;

about 5% (w/v) sucrose; and about 3% (w/v) mannitol;

wherein the pH of the formulation is about pH 7.

In an alternative exemplary embodiment of the invention, the invention provides a stable lyophilized antibody formulation suitable for subcutaneous administration, the formulation comprising:

about 100 mg/mL of a bispecific antibody or an antigen binding fragment thereof, wherein the antibody or antigen binding fragment thereof comprises a heavy chain variable region comprising the amino acid sequences of SEQ ID NOs: 2 and 4, and a light chain variable region comprising the amino acid sequences of SEQ ID NOs: 1 and 3;

about 10 mM of a buffering system, wherein the buffering system comprises a Tris buffer concentration of about 3.7 mM and a Phosphate buffer concentration of about 6.3 mM;

about 0.2% (w/v) polysorbate 80;

about 5% (w/v) sucrose; and about 3% (w/v) proline;

wherein the pH of the formulation is about pH 7.

In another alternative exemplary embodiment of the invention, the invention provides a stable lyophilized antibody formulation suitable for subcutaneous administration, the formulation comprising:

about 100 mg/mL of a bispecific antibody or an antigen binding fragment thereof, wherein the antibody or antigen binding fragment thereof comprises a heavy chain variable region comprising the amino acid sequences of SEQ ID NOs: 2 and 4, and a light chain variable region comprising the amino acid sequences of SEQ ID NOs: 1 and 3;

about 10 mM of a buffering system, wherein the buffering system comprises a Tris buffer concentration of about 3.7 mM and a Phosphate buffer concentration of about 6.3 mM;

about 0.2% (w/v) polysorbate 80;

about 5% (w/v) sucrose; and about 3% (w/v) mannitol;

wherein the pH of the formulation is about pH 7.

vii. Stability

The formulations of the invention are stable at 2-8° C. for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months or more. In exemplary embodiments, they are stable at 2-8° C. for at least about 6 months or more. In other exemplary embodiments, they are stable at 2-8° C. for at least about 9 months. In further exemplary embodiments, they are stable at 2-8° C. for at least about 1 year or more, more preferably about 2 years, and even more preferably about 3 years.

C. Modes of Administration

In certain embodiments of the invention, the formulations are suitable for administration parenterally, intravenously, intramuscularly, intradermally, subcutaneously, or a combination thereof. The formulations of the invention are suitable for delivery by a variety of techniques. In preferred embodiments of the invention, the formulation is administered subcutaneously. For example, it is preferred that formulations containing 100 mg/mL of anti-IL-4/anti-IL-13 bispecific antibody are administered subcutaneously. Therefore, the formulations are preferably sterile. Methods for making formulations sterile are well known in the art and include, for example, filtration through sterile filtration membranes or autoclaving the ingredients of the formulation, with the exception of the antibodies, at about 120° C. for about 30 minutes.

D. Dosages and Dosage Forms

Effective doses of the formulations of the invention vary depending upon many different factors, including means of administration, target site, physiological state of the subject, whether the subject is human or an animal, other medications administered, and whether treatment is prophylactic or therapeutic. Usually, the subject is a human, but non-human mammals including transgenic mammals can also be treated. Treatment dosages may need to be titrated to optimize safety and efficacy. Preferably, the dose ranges from 100-200 mg/vial.

The formulations of the invention may be administered on multiple occasions. Intervals between single dosages can be daily, weekly, biweekly, monthly or yearly. Intervals can also be irregular. In some methods, the dosage is adjusted to achieve a certain plasma binding agent, such as an antibody, concentration. Dosage and frequency will vary depending on the half-life of the anti-IL-4/anti-IL-13 bispecific antibody in the subject. In general, human antibodies show the longest half-life, followed by humanized antibodies, chimeric antibodies, and nonhuman antibodies.

In further embodiments, the invention provides a pharmaceutical unit dosage form comprising a therapeutically effective amount of a formulation of the invention for the treatment of one or more diseases in a subject through administration of the dosage form to the subject. In a preferred embodiment, the subject is a human. The human may be an adult or may be an infant. The term "pharmaceutical unit dosage form" refers to a physically discrete unit suitable as unitary dosages for the subjects to be treated, each unit containing a predetermined quantity of active compound calculated to produce the desired therapeutic/prophylactic effect in association with the required citrate buffer and pH.

The unit dosage form may be a container comprising the formulation. Suitable containers include, but are not limited to, sealed ampoules, vials, bottles, syringes, and test tubes. The containers may be formed from a variety of materials, such as glass or plastic, and may have a sterile access port (for example, the container may be a vial having a stopper pierceable by a hypodermic injection needle). In a preferred embodiment the container is a vial. Generally, the container should maintain the sterility and stability of the formulation.

In specific embodiments, the formulations are packaged in 7, 10, 15 or 20 mL vials that are made of clear, colorless type I glass, and closed with a stopper (fluoropolymer-coated bromobutyl) sealed with flip-of caps with flange (polypropylene).

In specific embodiment, the formulations are secondarily packaged in a container, such as a cardboard box, that protects the vials from light.

The formulations to be used for in vivo administration must be sterile. That can be accomplished, for example, by filtration through sterile filtration membranes. For example, the liquid formulations of the present invention may be sterilized by filtration using a 0.2 µm or a 0.22 µm filter.

E. Methods of Treatment

Further provided herein are methods for treating an IL-4 and/or IL-13-mediated disease or disorder, the methods comprising administering a formulation of the invention to a subject. In certain embodiments, the IL-4 and/or IL-13-mediated disease is cancers, inflammation, autoimmune diseases, infections, cardiovascular diseases, respiratory diseases, neurological diseases and metabolic diseases.

The formulations of the present invention may be used to treat, suppress or prevent disease, such as an allergic disease, a Th2-mediated disease, IL-13-mediated disease, IL-4-mediated disease, and/or IL-4/IL-13-mediated disease. Examples of such diseases include, Hodgkin's disease, asthma, allergic asthma, atopic dermatitis, atopic allergy, ulcerative colitis, scleroderma, allergic rhinitis, COPD3 idiopathic pulmonary fibrosis, chronic graft rejection, bleomycin-induced pulmonary fibrosis, radiation-induced pulmonary fibrosis, pulmonary granuloma, progressive systemic sclerosis, schistosomiasis, hepatic fibrosis, renal cancer, Burkitt lymphoma, Hodgkins disease, non~Hodgkins disease, Sezary syndrome, asthma, septic arthritis, dermatitis herpetiformis, chronic idiopathic urticaria, ulcerative colitis, scleroderma, hypertrophic scarring, Whipple's Disease, benign prostate hyperplasia, a lung disorder in which IL-4 receptor plays a role, condition in which IL-4 receptor-mediated epithelial barrier disruption plays a role, a disorder of the digestive system in which IL-4 receptor plays a role, an allergic reaction to a medication, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, cystic fibrosis, allergic bronchopulmonary mycosis, chronic obstructive pulmonary disease, bleomycin-induced pneumopathy and fibrosis, pulmonary alveolar proteinosis, adult respiratory distress syndrome, sarcoidosis, hyper IgE syndrome, idiopathic hypereosinophil syndrome, an autoimmune blistering disease, pemphigus vulgaris, bullous pemphigoid, myasthenia gravis, chronic fatigue syndrome, nephrosis.

The term "allergic disease" refers to a pathological condition in which a patient is hypersensitized to and mounts an immunologic reaction against a substance that is normally nonimmunogenic. Allergic disease is generally characterized by activation of mast cells by IgE resulting in an inflammatory response (e.g. local response, systemic response) that can result in symptoms as benign as a runny nose, to life-threatening anaphylactic shock and death. Examples of allergic disease include, but are not limited to, allergic rhinitis (e.g., hay fever), asthma (e.g., allergic asthma), allergic dermatitis (e.g., eczema), contact dermatitis, food allergy and urticaria (hives).

The term "Th2-mediated disease" refers to a disease in which pathology is produced (in whole or in part) by an immune response (Th2-type immune response) that is regulated by CD4$^+$ Th2 T lymphocytes, which characteristically produce IL-4, IL-5, IL-9 and IL-13. A Th2-type immune response is associated with the production of certain cytokines (e.g., IL-4, IL-13) and of certain classes of antibodies (e.g., IgE), and is associate with humoral immunity. Th2-mediated diseases are characterized by the presence of elevated levels of Th2 cytokines (e.g., IL-4, IL-13) and/or certain classes of antibodies (e.g., IgE) and include, for example, allergic disease (e.g., allergic rhinitis, atopic dermatitis, asthma (e.g., atopic asthma), allergic airways disease (AAD), anaphylactic shock, conjunctivitis), autoimmune disorders associated with elevated levels of IL-4 and/or IL-13 (e.g., rheumatoid arthritis, host-versus-graft disease, renal disease (e.g., nephritic syndrome, lupus nephritis)), and infections associated with elevated levels of IL-4 and/or IL-13 (e.g., viral, parasitic, fungal (e.g., *C. albicans*) infection). Certain cancers are associated with elevated levels of IL-4 and/or IL-13 or associated with IL-4-induced and/or IL-13-induced cancer cell proliferation (e.g., B cell lymphoma, T cell lymphoma, multiple myeloma, head and neck cancer, breast cancer and ovarian cancer). These cancers can be treated, suppressed or prevented using the formulations of the invention.

The term "cancer" refers to or describes the physiological condition in mammals, in particular humans, which is typically characterized by unregulated cell growth. Examples of cancer include, but are not limited to, carcinoma, lymphoma, blastoma, sarcoma, and leukemia.

The term "autoimmune disease" refers to a non-malignant disease or disorder arising from and directed against an individual's own tissues. Examples of autoimmune diseases or disorders include, but are not limited to, inflammatory responses such as inflammatory skin diseases including psoriasis and dermatitis; allergic conditions such as eczema and asthma; other conditions involving infiltration of T cells and chronic inflammatory responses; atherosclerosis; diabetes mellitus (e.g. Type I diabetes mellitus or insulin dependent diabetes mellitis); multiple sclerosis and central nervous system (CNS) inflammatory disorder.

In certain embodiments, the formulations of the invention can be administered in combination with one or more therapies (e.g., therapies that are not the formulations of the invention that are currently administered to prevent, treat, manage, and/or ameliorate an IL-4 and/or IL-13-mediated disease. The use of the term "in combination" does not restrict the order in which therapies are administered to a subject. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject that had, has, or is susceptible to an IL-4 and/or IL-13-mediated disease. Any additional therapy can be administered in any order with the other additional therapies. Non-limiting examples of therapies that can be administered in combination with an antibody of the invention include approved anti-inflammatory agents listed in the U.S. Pharmacopoeia and/or Physician's Desk Reference.

F. Kits

Certain embodiments of the invention include a kit comprising a formulation of the invention. The kit may further comprise one or more containers comprising pharmaceutically acceptable excipients, and include other materials desirable from a commercial and user standpoint, including filters, needles and syringes. Associated with the kits can be instructions customarily included in commercial packages of therapeutic, prophylactic or diagnostic products, that contain information about, for example, the indications, usage, dosage, manufacture, administration, contra-indications, and/or warnings concerning the use of such therapeutic, prophylactic or diagnostic products.

EXAMPLES

To help illustrate the invention, the following examples are provided. The examples are not intended to limit the scope of the invention in any way. In general, the practice of the present invention employs, unless otherwise indicated, conventional techniques of pharmaceutical formulation, chemistry, molecular biology, recombinant DNA technology, immunology such as antibody technology, and standard techniques of polypeptide preparation as described, for example, in Sambrook, Fritsch and Maniatis, Molecular Cloning: Cold Spring Harbor Laboratory Press (1989); Antibody Engineering Protocols (Methods in Molecular Biology), volume 51, Ed.: Paul S., Humana Press (1996); Antibody Engineering: A Practical Approach (Practical Approach Series, 169), Eds.: McCafferty J. et al., Humana Press (1996); Antibodies: A Laboratory Manual, Harlow and Lane, Cold Spring Harbor Laboratory Press (1999); and Current Protocols in Molecular Biology, Eds. Ausubel et al., John Wiley & Sons (1992).

Abbreviations used in Examples 2-6 are:
BD: Biotechnology Development
BsAb: Bispecific Antibody
DLS: Dynamic Light Scattering
DoE: Design of Experiment
DP: Drug Product
DS: Drug Substance
DSC: Differential Scanning calorimetry
FCM: Flow Cell Microscopy
FDS: Formulated Drug Substance
FT-IR: Fourier Transformed-Infra Red
HAP: HydroxyAPatite chromatography
HDPE: High-Density PolyEthylene
HMW: High Molecular Weight
HPLC: High Performance Liquid Chomatography
IEF: IsoElectroFocusing
IgG: Immunoglobulin G IL: Interleukin
kDa: kilo Dalton
LMW: Low Molecular Weight
Nd: Not Determined
PEG: PolyEthylene Glycol
PES: PolyEtherSulfone
PS80: PolySorbate 80
PVDF: PolyVinylidene DiFluoride
rpm: round per minute
SC: Subcutaneous
SDS-PAGE: Sodium Dodecyl Sulfate-PolyAcrylamide Gel Electrophoresis
SEC: Size Exclusion Chromatography
SLS: Static Light Scattering
Sq: Sufficient quantity
TGA: Thermo Gravimetric Analysis
UF/DF: UltraFiltration/DiaFiltration
USP: United States Pharmacopeia
UV-Vis: UltraViolet-Visible
w/v: weight/volume
WFI: Water For Injection
XRPD:X-Ray Powder Diffraction A humanized IgG4 anti-IL-4/anti-IL-13 bispecific antibody comprising a heavy chain variable region that binds to both IL-13 and IL-4 comprising the amino acid sequences of SEQ ID NOs: 2 and 4, and a light chain variable region that binds to both IL-13 and IL-4 comprising the amino acid sequences of SEQ ID NOs: 1 and 3 (the "Lead Antibody") was used in the following examples in order to determine optimal formulation conditions.

The objective of the following formulation studies (Examples 2-6) was to understand the Lead Antibody's behavior in solution and in the freeze-dried state (i.e., to identify the major degradation pathways) and to determine suitable buffer-pH systems and additives that provide a good stability for the Lead Antibody at about 100 mg/mL for further formulation development.

The following shows the drug substance used in Examples 2-6:

The Lead Antibody post HAP purification step (last step of the downstream processing):
Batch #RSN0169 (study #P5 to P6)
Formulation buffer: sodium phosphate buffer 75 mM, pH 6.7
Concentration: 10.4 mg/mL;
Batches #RSN0169-SZW 320, 326 and 327 (study #P7 to P13)
Formulation buffer: sodium phosphate buffer 59 mM, pH 6.9
Concentration: 4.5 mg/mL;
Batch #RSN0169-SZW 330 (study #P14)
Formulation buffer: sodium phosphate buffer 55 mM, NaCl 20 mM, pH 6.8
Concentration: 4.4 mg/mL; and
Batch # RSN0152 (study #P15 to P21)
Formulation buffer: sodium phosphate buffer 55 mM, NaCl 20 mM, pH 6.8
Concentration: 3.9 mg/mL.

For each formulation assay, the Lead Antibody concentration was adjusted at the end of the UF/DF in water or final buffer and then diluted further with appropriate amounts of concentrated buffer and additives solutions up to the desired final formulation (see Table 1 for details).

TABLE 1

Details of the formulation adjustment

| Assay # | Initial concentration[a] | Initial Buffer[a] | Final concentration[b] |
|---|---|---|---|
| P5-7 | 2 mg/mL | Water | 1 mg/mL |
| P12 | 95 mg/mL | Water | 85 mg/mL |
| P13 | 112 mg/mL | Water | 100 mg/mL |
| P14-16 | 27 mg/mL | Water | 20 mg/mL |
| P15 | 125 mg/mL | Water | 100 mg/mL |
| 17 | 46 mg/mL | Water | 38 mg/mL |
| P18 | 46 mg/mL | Phosphate/Tris 3.5 mM | 38 mg/mL |
| P20 | 42 mg/mL | Phosphate/Tris 3.5 mM | 35 mg/mL |
| P21 | 42 mg/mL | Phosphate/Tris 3.5 mM | 35 mg/mL |

[a]Concentration and buffer after UF/DF and adjustment
[b]Concentration after dilution with concentrate buffer and additives solutions Each formulation was sterile filtered (Millex® GV, Millipore, 0.22 μm, PVDF) under laminar flow and a fraction was dispensed into a type 1 glass vial as appropriate for each stability time point, except for the freeze/thaw study for which polypropylene tubes were used.

The mechanical stress and thermal stress conditions were determined for the formulations in Examples 2-6.

In order to evaluate the influence of shaking stress on formulation assays #P5-7, vials were shaken at 350 rpm for 2 to 15 h at room temperature using a Rota Test 74401 and then analyzed.

In order to evaluate the influence of syringeability stress on formulation assays #P12, 13, 16-18, and 20, a potential impact of syringeability (i.e., shear stress within the needle) was assessed with HPLC syringes (Unimetrics Corporation 100 μL) when small volume samples were available and with Terumo 26G×½-0.45×12 mm syringes when larger volume samples were available.

In order to evaluate the influence of thermal stress on formulation assays #P5-7 and 13, vials were stored at 45° C. for 1 and 2 weeks, and then analyzed. The relevant temperature for thermal stress was determined by DSC. Assays #P5-7 and 13 were also stored at 5° C. for 2 weeks, and then analyzed.

In order to evaluate the influence of thermal stress on formulation assays #P12, 15, and 21, vials were stored at 5° C. for 3 to 6 weeks and analyzed every week. The solutions before lyophilisation, called Formulated Drug Substance (FDS), for assays #P16-18 and 20 were stored at 5° C. for 4 to 5 weeks and analyzed every week. Reconstituted solutions after lyophilisation for assays #P14, 16-18, and 20 were stored at 5° C. for 24 h and then analyzed.

Example 1—pH Optimization

The first step in the formulation development process was to determine the optimal pH for the Lead Antibody formulation. In order to determine the optimal pH, a low concentration of Lead Antibody was used (1 mg/ml, as opposed to 100 mg/ml), as this low concentration of Lead Antibody was sufficient to determine the optimal pH. Table 2 shows the formulations tested in this study.

TABLE 2

Assay #P5- pH screening

| Formulation #P5-x | Buffer system | pH | Concentration |
|---|---|---|---|
| 1 | Citrate 100 mM | 4.5 | 1 mg/ml |
| 2 | Citrate 100 mM | 5.0 | 1 mg/ml |
| 3 | Citrate 100 mM | 5.5 | 1 mg/ml |
| 4 | Citrate 100 mM | 6.0 | 1 mg/ml |
| 5 | Phosphate 100 mM | 6.5 | 1 mg/ml |
| 6 | Phosphate 100 mM | 7.0 | 1 mg/ml |
| 7 | Phosphate 100 mM | 7.5 | 1 mg/ml |
| 8 | Tris 100 mM | 8.0 | 1 mg/ml |
| 9 | Tris 100 mM | 8.5 | 1 mg/ml |

In this study, Formulation 1 was not stable because it led to conformational instability for the Lead Antibody. Specifically, the Lead Antibody tended to unfold. Also, Formulation 9 led to deamidation. Thus, it was determined that the optimal pH for the Lead Antibody formulation would be within a narrow range around pH 7.0.

Subsequent studies of other formulation parameters, such as buffers, surfactants, and stabilizing agents, included higher concentrations of Lead Antibody. These subsequent studies confirmed the above conclusions regarding the optimal pH for the Lead Antibody formulation when high concentrations of Lead Antibody were used.

Example 2—Buffer System/Ionic Strength (Salt)

Buffers

The next step in the formulation development process was to determine the optimal buffer for the Lead Antibody formulation. Several different buffers were tested, such as histidine, phosphate, Tris, and combinations thereof, in several different assays.

TABLE 3

Assay #P6- Buffer system screening at 1 mg/ml

| Formulation #P6-x | Buffer system | pH | Concentration |
|---|---|---|---|
| 1 | Histidine 10 mM | 6.5 | 1 mg/ml |
| 2 | Phosphate 10 mM | 6.5 | 1 mg/ml |
| 3 | Phosphate 10 mM | 7.0 | 1 mg/ml |
| 4 | Phosphate 10 mM | 7.5 | 1 mg/ml |
| 5 | Tris 10 mM | 7.0 | 1 mg/ml |
| 6 | Tris 10 mM | 7.5 | 1 mg/ml |
| 7 | Phosphate 60 mM | 7.0 | 1 mg/ml |

TABLE 4

Assay #P7- Salt screening at 1 mg/ml

| Formulation #P7-x | Buffer system | pH | Concentration | Additive |
|---|---|---|---|---|
| 1 | Phosphate 10 mM | 7.0 | 1 mg/ml | NaCl 70 mM |
| 2 | Phosphate 10 mM | 7.0 | 1 mg/ml | NaCl 140 mM |
| 3 | Tris 10 mM | 7.0 | 1 mg/ml | NaCl 70 mM |
| 4 | Tris 10 mM | 7.0 | 1 mg/ml | NaCl 140 mM |

TABLE 5

Assay #P13- Buffer/Salt screening at 100 mg/ml

| Formulation #P13-x | Buffer system | pH | Concentration | Additive |
|---|---|---|---|---|
| 1 | Phosphate 10 mM | 7.0 | 100 mg/ml | — |
| 2 | Phosphate 10 mM | 7.0 | 100 mg/ml | NaCl 70 mM |
| 3 | Tris 10 mM | 7.0 | 100 mg/ml | — |
| 4 | Tris 10 mM | 7.0 | 100 mg/ml | NaCl 70 mM |

TABLE 6

Buffer systems formulas

| Buffer system (acid/base) | pH | Acid concentration | Base concentration |
|---|---|---|---|
| Citric acid/NaOH | 4.5 | 100 mM | Sq pH 5.0 |
| Citric acid/NaOH | 5.0 | 100 mM | Sq pH 5.0 |
| Citric acid/NaOH | 5.5 | 100 mM | Sq pH 5.5 |
| Citric acid/NaOH | 6.0 | 100 mM | Sq pH 6.0 |
| Sodium dihydrogen phosphate/NaOH | 6.5 | 100 mM | Sq pH 6.5 |
| Sodium dihydrogen phosphate/NaOH | 6.5 | 10 mM | Sq pH 6.5 |
| Sodium dihydrogen phosphate/NaOH | 7.0 | 100 mM | Sq pH 7.0 |
| Sodium dihydrogen phosphate/NaOH | 7.0 | 60 mM | Sq pH 7.0 |
| Sodium dihydrogen phosphate/NaOH | 7.0 | 10 mM | Sq pH 7.0 |
| Sodium dihydrogen phosphate/NaOH | 7.5 | 100 mM | Sq pH 7.5 |
| Sodium dihydrogen phosphate/NaOH | 7.5 | 10 mM | Sq pH 7.5 |
| Phosphoric acid/Tris aminomethan | 8.0 | Sq pH 8.0 | 100 mM |
| Phosphoric acid/Tris aminomethan | 8.5 | Sq pH 8.5 | 100 mM |
| Phosphoric acid/Tris aminomethan | 7.0 | Sq pH 7.0 | 10 mM |
| Phosphoric acid/Tris aminomethan | 7.5 | Sq pH 7.5 | 10 mM |
| HCl/L-Histidine | 6.5 | Sq pH 6.5 | 10 mM |
| Sodium dihydrogen phosphate/Tris aminomethan | 7.0 | 6.3 mM | 3.7 mM |
| Sodium dihydrogen phosphate/Tris aminomethan | 7.0 | 2.22 mM | 1.28 mM |

Upon processing and formulation compounding, filtered formulation assays and controls were free of visible and sub-visible particles, and the SEC analysis showed a purity <92.0% due to a starting DS containing 5.5% of HMW.

Onset and denaturation temperatures obtained by DSC indicated a better thermal stability for the following buffer-pH systems:

Phosphate pH 6.5 and 7.0: #P5-5, P5-6, P6-2, P6-3
Tris pH 7.0 and 7.5: #P6-5, P6-6 for which the onset temperature was around 61° C. compared for example to 48° C. for pH 4.5 and 59° C. for the Histidine buffer.

Colloidal stability obtained by SLS indicated a better stability for the following buffer-pH systems:

Phosphate pH 7.5: #P6-4
Tris pH 7.0 and 7.5: #P6-5, P6-6 for which the second virial coefficient was close to 3.0 $10^{-4}$ mL·mol/g$^2$ compared for example to 0.4 $10^{-4}$ mL·mol/g$^2$ for the Histidine buffer and 1.5 $10^{-4}$ mL·mol/g$^2$ for the Phosphate pH 7.0 buffer.

Figure 3:
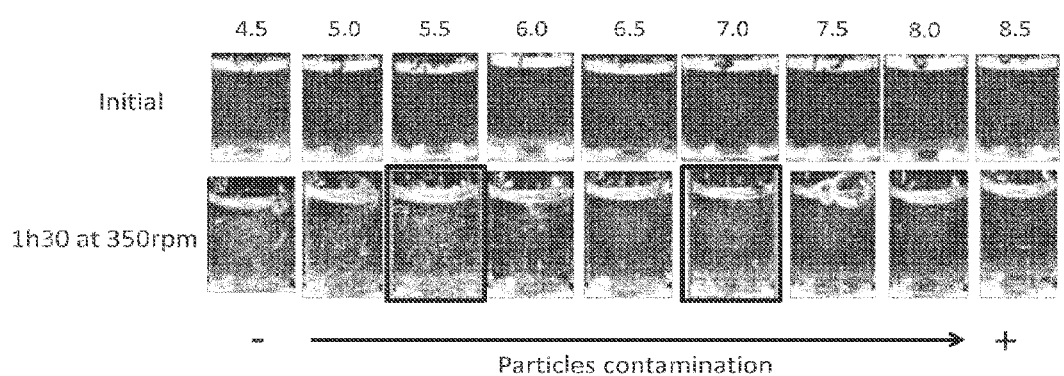
FIG. 3 is a group of pictures showing particle contamination for assay #P5 (pH-buffer screening) after shaking stress.

Different levels of particle contamination were observed after 1 h30 shaking stress (see FIG. 3).

With regard to visible particles, buffer-pH system candidates showing good stability for assay #P5 were as follows:

Phosphate pH 6.5, 7.0 and 7.5: #P5-5, P5-6 and P5-7
Tris pH 8.0 and 8.5: #P5-8 and P5-9

Assay #6 was performed for these two buffer systems with pHs between 6.5 and 7.5. Candidates showing the best stability were as follows:

Phosphate pH 7.0 and 7.5: #P6-3 and P6-4
Tris pH 7.0 and 7.5: #P6-5 and P6-6

Basic pHs seemed to be better for minimizing particles formation.

Shaking stress and thermal stress (2 weeks at 45° C.) are relevant methods for buffer-pH system discrimination with regard to sub-visible particles.

Figure 4:
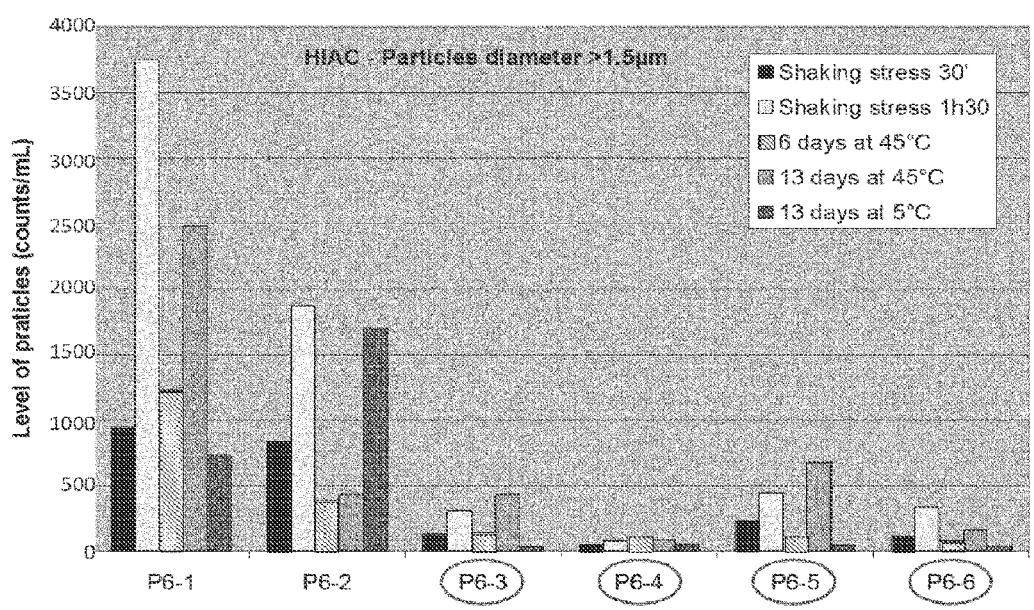
FIG. 4 is a graph showing sub-visible particles >1.5 μm contamination after several stresses for assay #P6 (pH-buffer screening).
Figure 5:
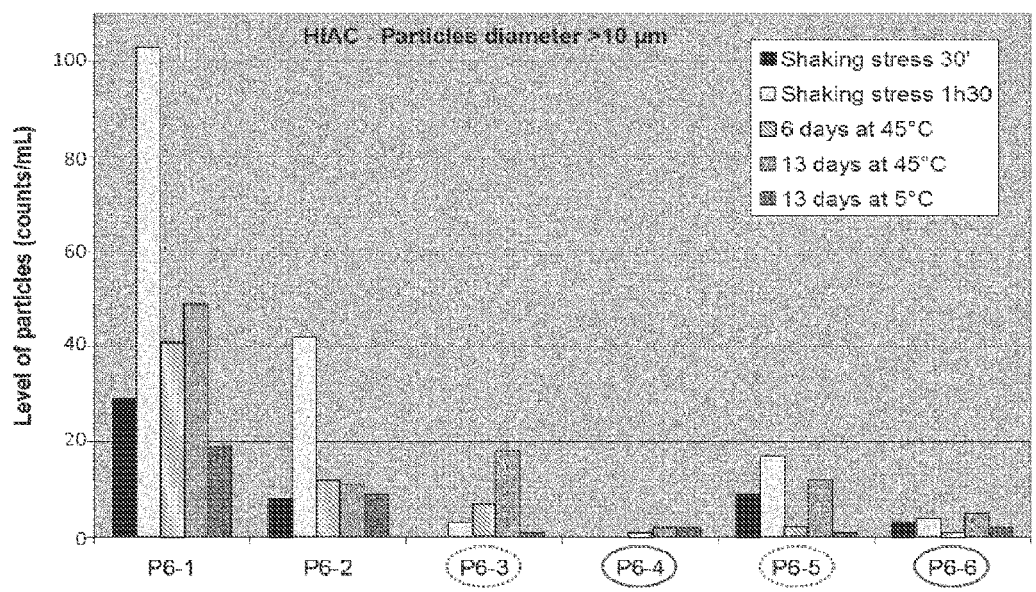
FIG. 5 is a graph showing sub-visible particles >10 μm contamination after several stresses for assay #P6 (pH-buffer screening).

Buffer-pH system candidates providing a good stability were:

Assay #5: formulations #P5-6 to P5-9, i.e., pH ≥7.0
Assay #6 (see FIG. 4 and FIG. 5):
Phosphate 7.5: # P6-4
Tris 7.5: # P6-6
Followed by:
Phosphate pH 7.0: #P6-3
Tris pH 7.0: #P6-5

Note that the Histidine buffer (#P6-1) showed, for all stressed conditions, an important destabilizing effect.

HIAC measurements confirmed the visual inspection: basic pHs were better for minimizing particle formation. Furthermore, at the same pH, Phosphate-based formulations provided slightly less sub-visible particles than Tris buffering-system.

Regarding assay #5 and 6, thermal stress showed interesting results for both HMW and LMW. Note that formulation #P5-1 (pH 4.5) was totally degraded after 1 week at 45° C.; so was formulation #P5-2 after 2 weeks at 45° C. These two samples will be cast out of the following analysis.

Figure 6:
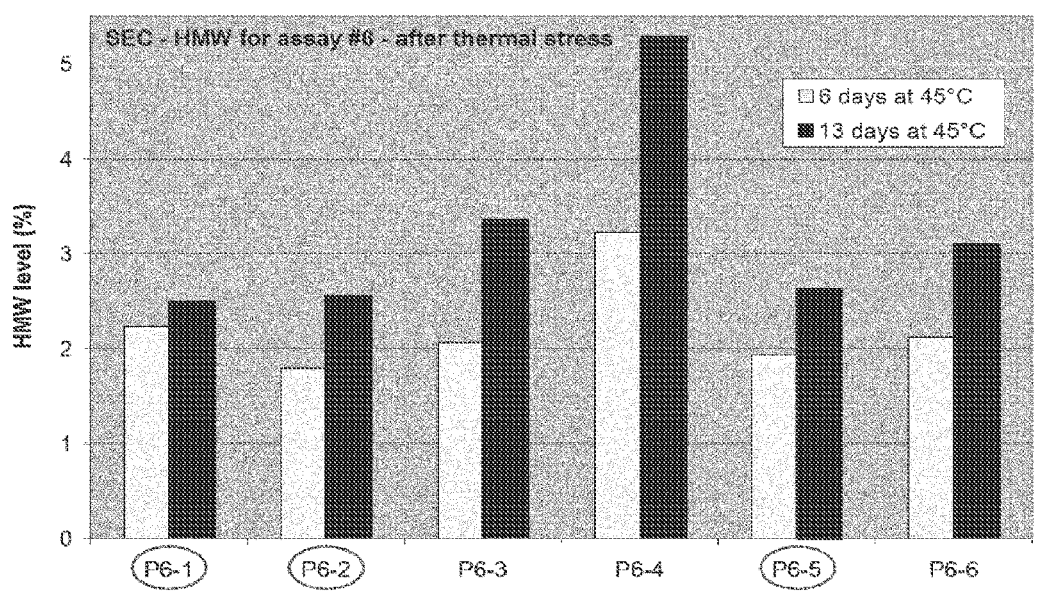
FIG. 6 is a graph showing HMW level for assay #P6 (pH-buffer screening) after thermal stress.

With regards to HMW, results after 2 weeks at 45° C. were similar for formulations #P5-6 to P5-9 (pH ≥7.0) and better for #P5-5 to P5-3 as pH decreased from 6.5 to 5.5. For assay #6, this tendency was confirmed and buffer-pH system candidates providing a good stability were (see FIG. 6):

Phosphate pH 6.5: #P6-2
Tris pH 7.0: #P6-5
Histidine pH 6.5: #P6-5

Thus, pH 6.5 provided a better stability for minimizing HMW formation than pH 7.0, which itself was better than pH 7.5. Furthermore, at the same pH (7.0 and 7.5), Tris-based formulations provided slightly less HMW than Phosphate buffering-system.

Figure 7:
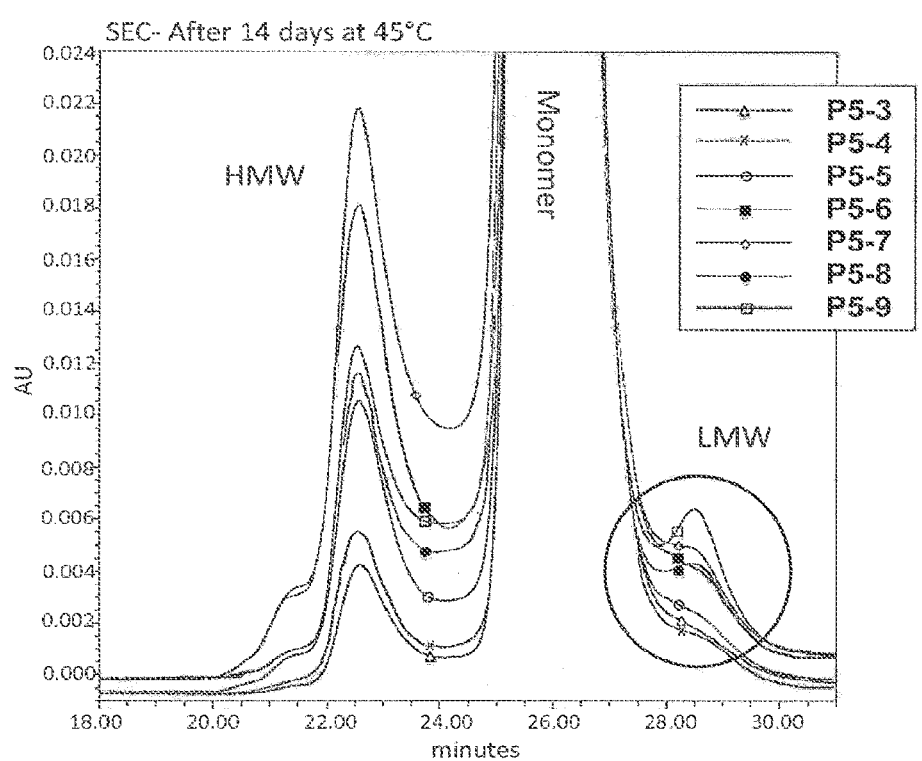
FIG. 7 is a graph showing SEC chromatograms of assay #P5 (pH-buffer screening) after 2 weeks at 45° C.
Figure 8:
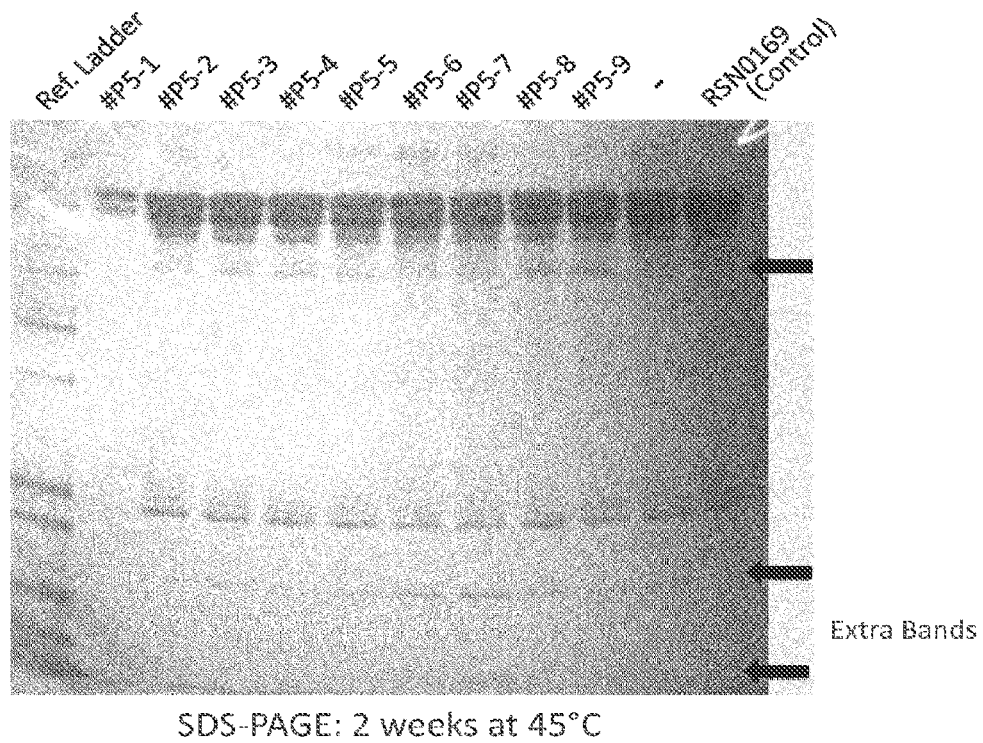
FIG. 8 is a picture of an SDS-PAGE gel of assay #P5 (pH-buffer screening) after 2 weeks at 45° C.

With regards to LMW, formulations #P5-3 to P5-5 (pH≤6.5) showed a good stability after 2 weeks at 45° C. Formations of substantial LMW and extra bands on SDS-PAGE gel occurred for formulation #P5-6 to P5-9 (7.0≤pH≤8.5). LMW degradation was more pronounced for formulation #P5-9 (Tris pH 8.5) (see FIG. 7) and extra bands on SDS-PAGE gel were particularly visible for #P5-7 (Phosphate pH 7.5) (see FIG. 8). Note that the products of degradation seemed different for Phosphate and Tris buffered systems.

Assay #6 confirmed these conclusions and showed that for the same pH, Phosphate-based formulations provided slightly more LMW than Tris buffering-systems.

Regarding HMW and LMW, acidic pHs seemed to present a better stability than basic ones, with a slight advantage for Tris over Phosphate buffering-system.

Figure 9:
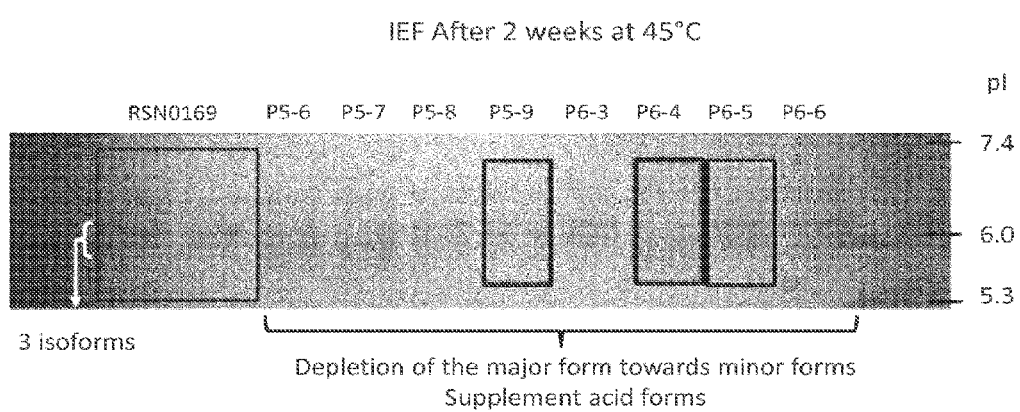
FIG. 9 is a picture of an IEF gel after 2 weeks at 45° C. for assay #P5 and 6 (pH-buffer screening).

Thermal stress at 45° C. for 4 weeks was a relevant mean to force chemical degradation of the Lead Antibody (i.e., change in acidic pattern) evidenced by IEF, and therefore to select buffer-pH systems providing a good stability for the Lead Antibody (see FIG. 9). The least stable formulations were Tris pH 8.5 (#P5-9) and Phosphate pH 7.5 (#P6-4), as the isoform pattern, both presented 2 extra acid forms and the major form became minor. The buffer-pH system candidate showing a good stability was Tris pH 7.0 (#P6-5).

In conclusion, based on initial state analysis and stress program results on assays #P5 and 6 (1 mg/mL solutions), the pH has been set at 7.0. This selection is a compromise between a good stability regarding visible and sub-visible particles (basic pHs) and stability regarding HMW and LMW (acid pHs). Regarding buffering systems, both Phosphate and Tris showed advantages for the selected pH: Phosphate regarding visible/sub-visible particles, and Tris regarding HMW and LMW.

Note that for the first additives assessment, buffering systems Phosphate 10 mM or Tris 10 mM have been used:

To confirm the above results on 100 mg/mL Lead Antibody solutions,

And to test the freeze-drying process on both buffering systems separately.

Figure 19:
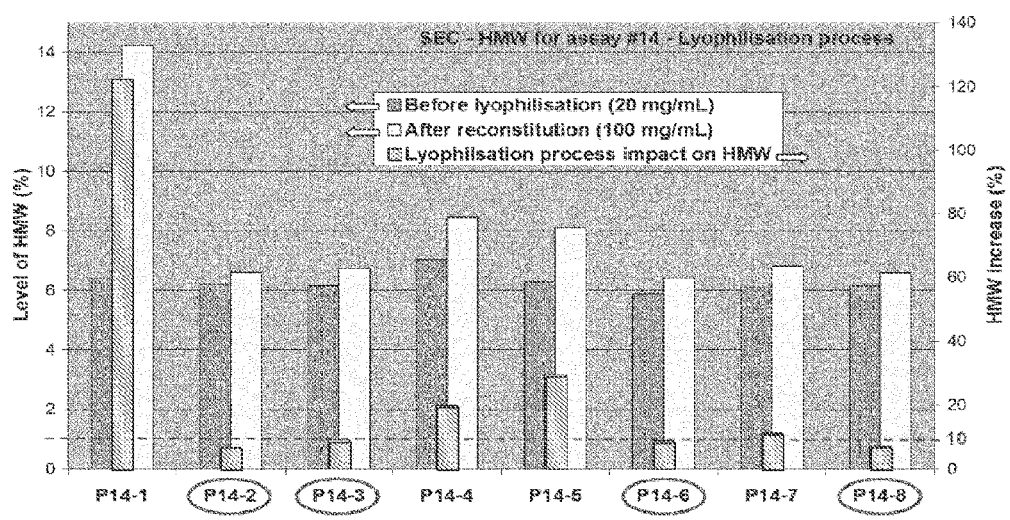
FIG. 19 is a graph showing HMW level for assay #P14 (additive) after lyophilisation process.

The results above were confirmed and both buffering systems (#P14-3 and P14-8) showed good results during the freeze drying process (see FIG. 19).

At pH 7.0, Phosphate has a stronger buffering capacity than Tris; however, unlike Tris, its base has a tendency to precipitate during freezing steps. To combine the advantages of both Tris and Phosphate, a mix of these two buffering systems has been selected: Phosphate 6.3 mM and Tris 3.7 mM. Even though the use of Tris buffer or phosphate buffer is known in the art (the use of each one separately), the combination of Tris buffer and phosphate buffer in a buffer system is highly unusual and is not known in the art.

Conductivity (pH and Buffer Selection)

The solution before lyophilisation had a conductivity of around 300 μS/cm, which gives a theoretical conductivity of 850 μS/cm for the DP after reconstitution.

We first tried a commonly used buffer for a mAb: Histidine, in its buffering region at pH 6.2 and 6.6 and at a concentration of 10 mM. At pH 6.2, an insolubility issue had been encountered with precipitation of the Lead Antibody at room temperature (see FIG. 29). At pH 6.6, the solution was slightly opalescent at room temperature, the second virial coefficient was low 0.4 $10^{-4}$ mL·mol/g$^2$. Unlike most mAbs, Histidine is not a good buffer for the Lead Antibody.

Then we tried another commonly used buffer: Phosphate in its buffering region at pH 6.5, 7.0 and 7.5, and at a concentration of 10 mM. For pH 6.5 and 7.0, the second virial coefficient was below $1.5\ 10^{-4}$ mL·mol/g$^2$, which means a low colloidal stability. For pH 7.5, the second virial coefficient was close to $3.0\ 10^{-4}$ mL·mol/g$^2$, which means a good colloidal stability, however a thermal stress (2 weeks at 45° C.) showed a decrease of purity (both HMW and LMW increase) more important than for pH 6.5 and 7.0. Phosphate is a good buffer, however at acidic pH the colloidal stability is low, and at basic pH the Lead Antibody is sensitive to thermal stress.

In order to expand the buffer screening, Tris was tested in its buffering region at pH 7.0, and 7.5, and at a concentration of 10 mM. Both pHs presented a good colloidal stability with a viral coefficient close to $3.0\ 10^{-4}$ mL·mol/g$^2$. Thermal stress (2 weeks at 45° C.) showed a decrease of purity (both HMW and LMW increase) more important for pH 7.5 than for pH 7.0. However, Tris at pH 7.0 provided a much better stability regarding HMW and a slightly better stability regarding LMW than Phosphate at the same pH. Tris pH 7.0 is a better buffering system than Tris pH 7.5 and phosphate pH 7.0. Although, in order to obtain a good buffering capacity of Tris at this pH (pka=8.1), the amount required would be greater to the maximum used in a commercialized product.

In order to optimize the buffer for the Lead Antibody, a combination of Phosphate 6.5 mM/Tris 3.7 mM was selected to obtain a good buffering capacity at pH 7.0 due to Phosphate (pka=7.2), and a good stabilization of the Lead Antibody due to Tris.

As stated above, even though the use of Tris buffer or phosphate buffer is known in the art (the use of each one separately), the combination of Tris buffer and phosphate buffer in a buffer system is highly unusual and is not known in the art.

Ionic Strength/Salt Concentration

Sodium Chloride (NaCl) was tested with the two selected buffer-pH candidates at a concentration of 70 mM on 100 mg/mL Lead Antibody solutions.

Figure 10:
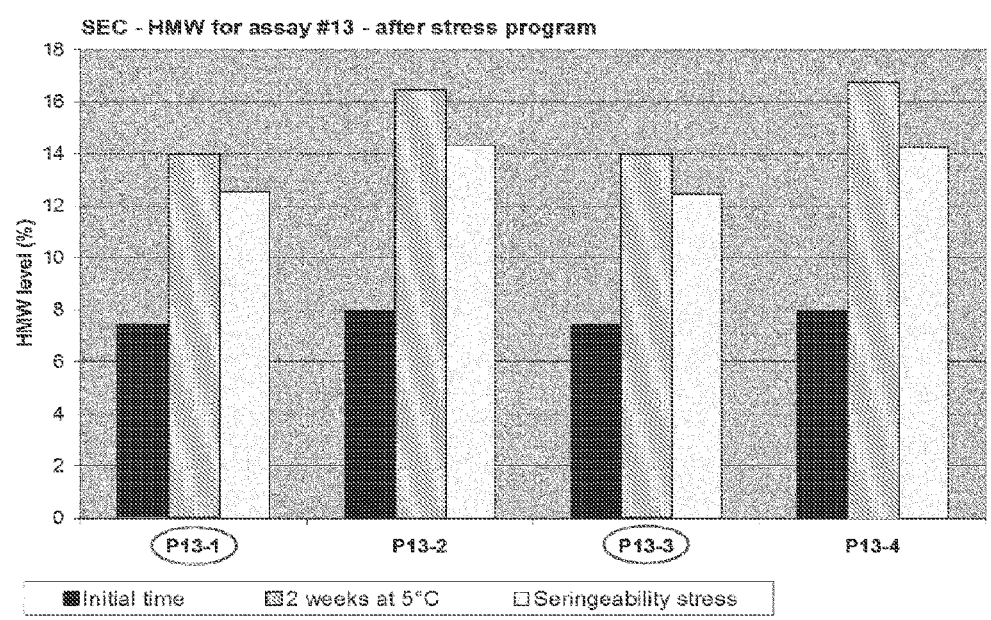
FIG. 10 is a graph showing HMW level after stress program on assay #P13 (salt effect).
Figure 33:
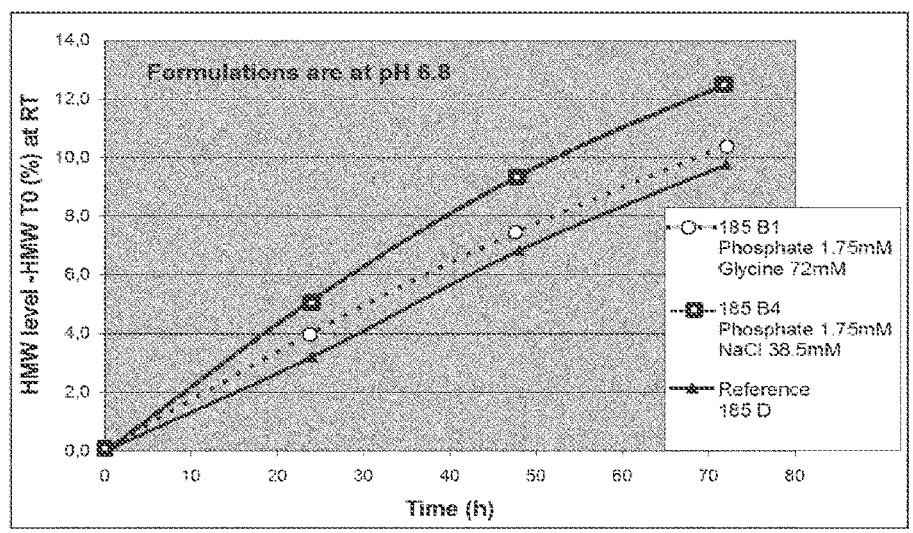
FIG. 33 is a graph showing HMW evolutions for NaCl at RT by SEC (assays #H04-185).

Onset and denaturation temperatures obtained by DSC as well as colloidal stability obtained by SLS did not indicate any substantial effect of NaCl on the stability of the solutions. After mechanical stress of formulation assay #P13 and two weeks storage at 5° C. of the same formulation, candidates #P13-1 and P13-3, i.e. without NaCl, showed a better stability regarding HMW formation (see FIG. 10). Same c/c in FIG. 33.

Increasing the salt concentration caused an increase in the ionic strength, which caused an increase in the kinetics of aggregation of the Lead Antibody. Thus, it was determined that the formulation should not contain salt or an osmotic agent. In addition, it was determined that the optimal formulation should comprise a low concentration of buffer in order to have a low ionic strength.

Example 3—Surfactant

The next step in the formulation development process was to determine the optimal excipients for the Lead Antibody formulation. The excipients must be sufficient to stabilize the Lead Antibody, and be compatible with lyophilisation. Several different surfactants were tested, such as polysorbates and poloxamers, in various concentrations.

TABLE 7

Assay #P12- Additives screening at 85 mg/ml

| Formulation #P12-x | Buffer system | pH | Concentration | Additive 1 | Additive 2 |
|---|---|---|---|---|---|
| 1 | Phosphate 10 mM | 7.0 | 85 mg/ml | PS80 0.01% (w/v) | Glycine 1% (w/v) (130 mM) |
| 3 | Phosphate 10 mM | 7.0 | 85 mg/ml | PS80 0.01% (w/v) | Sucrose 5% (w/v) |
| 4 | Phosphate 10 mM | 7.0 | 85 mg/ml | PS80 0.01% (w/v) | Trehalose 5% (w/v) |
| 5 | Phosphate 10 mM | 7.0 | 85 mg/ml | PS80 0.01% (w/v) | — |
| 6 | Phosphate 10 mM | 7.0 | 85 mg/ml | PS80 0.1% (w/v) | — |
| 7 | Phosphate 10 mM | 7.0 | 85 mg/ml | PS20 0.01% (w/v) | — |
| 8 | Phosphate 10 mM | 7.0 | 85 mg/ml | PS20 0.1% (w/v) | — |
| 9 | Phosphate 10 mM | 7.0 | 85 mg/ml | Poloxamer 0.05% (w/v) | — |
| 10 | Phosphate 10 mM | 7.0 | 85 mg/ml | Poloxamer 0.1% (w/v) | — |
| 11 | Phosphate 10 mM | 7.0 | 85 mg/ml | — | — |

TABLE 8

Assay #P23- Additives screening at 100 mg/ml

| Formulation #P23-x | Buffer system | pH | Concentration | Additive |
|---|---|---|---|---|
| 1 | Tris/Phosphate 10 mM | 7.0 | 100 mg/ml | PS80 0.1% (w/v) |
| 2 | Tris/Phosphate 10 mM | 7.0 | 100 mg/ml | PS80 0.2% (w/v) |
| 3 | Tris/Phosphate 10 mM | 7.0 | 100 mg/ml | PS80 0.3% (w/v) |

Immediately after 0.22 µm filtration, formulation assays and controls were free of visible and sub-visible particles. SEC analysis showed a purity <92.0% due to concentration of the Lead Antibody from 4.5 mg/mL to 100 mg/mL (starting DS contained 3.0% HMW).

Figure 11:
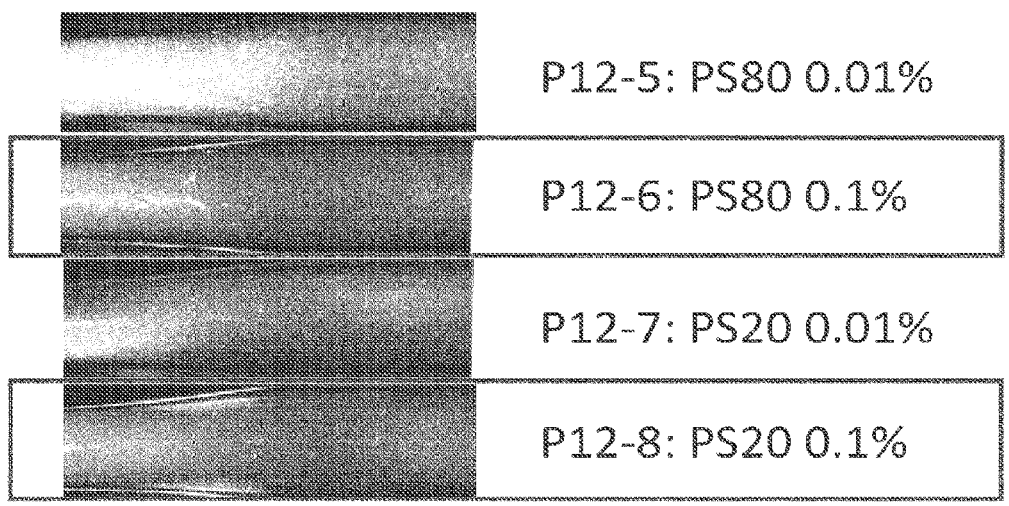
FIG. 11 shows pictures of binocular images of assay #P12 (surfactant) after mechanical stress.

Mechanical stress was a relevant mean to discriminate between formulation candidates. Due to availability of a limited amount of starting material, standard visual observation was not possible and therefore observation in capillary under a magnifying glass was used. With regard to visible/sub-visible particles, candidates showing a good stability for assay #12 were as follows (see FIG. 11):

PS80 0.1%: #P12-6

PS20 0.1%: #P12-8

Figure 12:
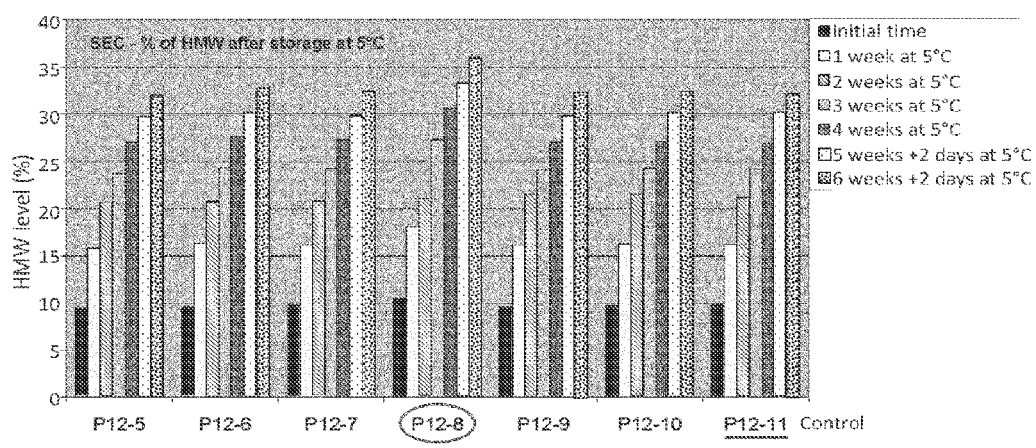
FIG. 12 is a graph showing HMW monitoring for assay #P12 (surfactant) while stored 6 weeks at 5° C.

Among the surfactants tested, none had an impact on HMW formation compared to the formulation without surfactant except for #P12-8 (PS20 0.1%), which had a slight negative effect over six weeks storage at 5° C. (see FIG. 12).

To conclude, there was no strong difference between surfactants. The following surfactant: PS80, was selected to prevent visible/sub-visible particle formation.

Next, various concentrations of PS80 were tested in the Lead Antibody formulation (see Table 23). PS80 concentrations from 0.05-0.2% were tested for shaking stress for 15 hours at 350 rpm (room temperature). The samples were analysed by flow cell microscopy, and the results are shown in Table 9. Table 9 shows that a PS80 concentration between 0.05 to 0.2% had an equivalent stabilizing effect for all concentrations regarding shaking stress. Thus, a PS80 concentration of 0.05 to 0.2% can be used in the formulation.

TABLE 9

| | PS80 concentration | | |
|---|---|---|---|
| | 15 h at 350 rpm at room temperature | | |
| | ≥2 µm | ≥10 µm | ≥25 µm |
| F2 (0.05% PS80) | 2589 | 148 | 21 |
| F3 (0.07% PS80) | 975 | 32 | 2 |
| F4 (0.1% PS80) | 698 | 58 | 3 |
| F5 (0.2% PS80) | 1969 | 98 | 16 |

FCM: particle number per mL

Example 4—Sucrose

As stated above, the next step in the formulation development process was to determine the optimal excipients for the Lead Antibody formulation. The excipients must be sufficient to stabilize the Lead Antibody, and be compatible with lyophilisation. Several different sugars were tested, such as sucrose, trehalose, and mannitol, in various concentrations.

TABLE 10

Assay #P14- Additives screening for a lyophilisate

| Form. #P14-x | Buffer system | pH | Strength | Additive 1 | Additive 2 | Additive 3 |
|---|---|---|---|---|---|---|
| 1 | Phosphate 10 mM | 7.0 | 100 mg/vial | PS80 0.1% (w/v) | — | — |
| 2 | Phosphate 10 mM | 7.0 | 100 mg/vial | PS80 0.1% (w/v) | Sucrose 10% (w/v) | — |
| 3 | Phosphate 10 mM | 7.0 | 100 mg/vial | PS80 0.1% (w/v) | Sucrose 5% (w/v) | Mannitol 3% (w/v) |
| 4 | Phosphate 10 mM | 7.0 | 100 mg/vial | PS80 0.1% (w/v) | NaCl 70 mM | Mannitol 3% (w/v) |
| 5 | Phosphate 10 mM | 7.0 | 100 mg/vial | PS80 0.1% (w/v) | NaCl 70 mM | Mannitol 3% (w/v) |
| 6 | Phosphate 10 mM | 7.0 | 100 mg/vial | PS80 0.1% (w/v) | Glycine 1% (w/v) | Mannitol 3% (w/v) |
| 7 | Phosphate 10 mM | 7.0 | 100 mg/vial | PS80 0.3% (w/v) | Sucrose 5% (w/v) | Mannitol 3% (w/v) |
| 8 | Tris 10 mM | 7.0 | 100 mg/vial | PS80 0.1% (w/v) | Sucrose 5% (w/v) | Mannitol 3% (w/v) |

TABLE 11

Assay #P15- Additives screening at 100 mg/ml - DoE

| Form. #P15-x | Buffer system | pH | Conc. | Additive 1 | Additive 2 | Additive 3 | Additive 4 |
|---|---|---|---|---|---|---|---|
| 1 | Phosphate 10 mM | 7.0 | 100 mg/ml | PS80 0.01% (w/v) | Sucrose 10% (w/v) | — | Proline 5.8% (w/v) |
| 2 | Phosphate 10 mM | 7.0 | 100 mg/ml | PS80 0.01% (w/v) | Mannitol 3% (w/v) | — | Proline 5.8% (w/v) |
| 3 | Phosphate 10 mM | 7.0 | 100 mg/ml | PS80 0.01% (w/v) | Trehalose 10% (w/v) | — | — |
| 4 | Phosphate 10 mM | 7.0 | 100 mg/ml | PS80 0.01% (w/v) | — | Ethanol 2% (w/v) | Glutamic acid 7.3% (w/v) |
| 5 | Phosphate 10 mM | 7.0 | 100 mg/ml | PS80 0.01% (w/v) | — | PEG 400 1% (w/v) | Aspartate 8.7% (w/v) |
| 6 | Phosphate 10 mM | 7.0 | 100 mg/ml | PS80 0.01% (w/v) | Trehalose 10% (w/v) | — | Aspartate 8.7% (w/v) |
| 7 | Phosphate 10 mM | 7.0 | 100 mg/ml | PS80 0.01% (w/v) | Sucrose 10% (w/v) | Glycerol 5% (w/v) | Glycine 1.9% (w/v) |
| 8 | Phosphate 10 mM | 7.0 | 100 mg/ml | PS80 0.01% (w/v) | Mannitol 3% (w/v) | PEG 400 1% (w/v) | — |
| 9 | Tris 10 mM | 7.0 | 100 mg/ml | PS80 0.01% (w/v) | Trehalose 10% (w/v) | PEG 400 1% (w/v) | Proline 5.8% (w/v) |
| 10 | Tris 10 mM | 7.0 | 100 mg/ml | PS80 0.01% (w/v) | Mannitol 3% (w/v) | — | Aspartate 8.7% (w/v) |
| 11 | Tris 10 mM | 7.0 | 100 mg/ml | PS80 0.01% (w/v) | Sucrose 10% (w/v) | Ethanol 2% (w/v) | — |
| 12 | Tris 10 mM | 7.0 | 100 mg/ml | PS80 0.01% (w/v) | — | Glycerol 5% (w/v) | — |
| 13 | Tris 10 mM | 7.0 | 100 mg/ml | PS80 0.01% (w/v) | Trehalose 10% (w/v) | Glycerol 5% (w/v) | Glutamic acid 7.3% (w/v) |
| 14 | Tris 10 mM | 7.0 | 100 mg/ml | PS80 0.01% (w/v) | — | — | Glycine 1.9% (w/v) |

TABLE 11-continued

Assay #P15- Additives screening at 100 mg/ml - DoE

| Form. #P15-x | Buffer system | pH | Conc. | Additive 1 | Additive 2 | Additive 3 | Additive 4 |
|---|---|---|---|---|---|---|---|
| 15 | Tris 10 mM | 7.0 | 100 mg/ml | PS80 0.01% (w/v) | Sucrose 10% (w/v) | — | Glutamic acid 7.3% (w/v) |
| 16 | Tris 10 mM | 7.0 | 100 mg/ml | PS80 0.01% (w/v) | Mannitol 3% (w/v) | Ethanol 2% (w/v) | Glycine 1.9% (w/v) |

TABLE 12

Assay #P16- Additives screening and process development for a lyophilisate

| Form. #P16-x | Buffer system | pH | Strength | Additive 1 | Additive 2 | Additive 3 | Additive 4 |
|---|---|---|---|---|---|---|---|
| 1 | Phosphate 10 mM | 7.0 | 100 mg/vial | PS80 0.1% (w/v) | Sucrose 5% (w/v) | Mannitol 3% (w/v) | — |
| 2 | Phosphate 10 mM | 7.0 | 100 mg/vial | PS80 0.1% (w/v) | Trehalose 5% (w/v) | Mannitol 3% (w/v) | — |
| 3 | Phosphate 10 mM | 7.0 | 100 mg/vial | PS80 0.05% (w/v) | Sucrose 5% (w/v) | Mannitol 3% (w/v) | — |
| 4 | Phosphate 10 mM | 7.0 | 100 mg/vial | PS80 0.1% (w/v) | Sucrose 5% (w/v) | Mannitol 3% (w/v) | PEG 4000 1% (w/v) |

TABLE 13

Assay #P17-FDS - Additives screening at 38 mg/mL

| Form. #P17-x- | FDS Buffer system | pH | Concentration | Additive 1 | Additive 2 | Additive 3 |
|---|---|---|---|---|---|---|
| 1 | Tris/Phosphate 3.3 mM | 7.0 | 38 mg/mL | PS80 0.033% (w/v) | Sucrose 3.33% (w/v) | — |
| 2 | Tris/Phosphate 3.3 mM | 7.0 | 38 mg/mL | PS80 0.033% (w/v) | Sucrose 1.67% (w/v) | Mannitol 1% (w/v) |
| 3 | Tris/Phosphate 3.3 mM | 7.0 | 38 mg/mL | PS80 0.033% (w/v) | — | Glycine 0.37% (w/v) |

TABLE 14

Assay #P17- Additives screening and process development for a lyophilisate

| Form. #P17-x | Buffer system | pH | Strength | Additive 1 | Additive 2 | Additive 3 |
|---|---|---|---|---|---|---|
| 1 | Tris/Phosphate 10 mM | 7.0 | 190 mg/vial | PS80 0.1% (w/v) | Sucrose 10% (w/v) | — |
| 2 | Tris/Phosphate 10 mM | 7.0 | 190 mg/vial | PS80 0.1% (w/v) | Sucrose 5% (w/v) | Mannitol 3% (w/v) |
| 3 | Tris/Phosphate 10 mM | 7.0 | 190 mg/vial | PS80 0.1% (w/v) | — | Glycine 2.2% (w/v) |

In conclusion, based upon the above studies, sucrose was chosen as an excipient because it stabilized the Lead Antibody. In addition, it is well known that sucrose is a lyoprotectant so it will improve the lyophilized formulation. In fact, lyophilization without sucrose leads to an increase in HMW (see FIG. 19). Further, 5% sucrose was found to be optimal for the formulation.

Example 5—Stabilizing Agents

As stated above, the next step in the formulation development process was to determine the optimal excipients for the Lead Antibody formulation. The excipients must be sufficient to stabilize the Lead Antibody, and be compatible with lyophilisation. Several different stabilizing agents were tested, such as mannitol, aspartate, proline, glycine, arginine and leucine, in various concentrations. This can be seen in the Tables below and in Tables 10-14 above.

TABLE 15

Assay #P18- Additives screening and process development for a lyophilisate

| Form. #P18-x | Buffer system | pH | Strength | Additive 1 | Additive 2 | Additive 3 |
|---|---|---|---|---|---|---|
| 1 | Tris/Phosphate 10 mM | 7.0 | 175 mg/vial | PS80 0.1% (w/v) | Sucrose 5% (w/v) | Mannitol 3% (w/v) |
| 2 | Tris/Phosphate 10 mM | 7.0 | 175 mg/vial | PS80 0.1% (w/v) | Sucrose 5% (w/v) | Aspartate 4.3% (w/v) |
| 3 | Tris/Phosphate 10 mM | 7.0 | 175 mg/vial | PS80 0.1% (w/v) | Sucrose 5% (w/v) | Proline 5.8% (w/v) |

TABLE 16

Assay #P20-FDS - Additives screening at 35 mg/mL

| Form. #P20-x- FDS | Buffer system | pH | Concentration | Additive 1 | Additive 2 | Additive 3 |
|---|---|---|---|---|---|---|
| 1 | Tris/Phosphate 3.5 mM | 7.0 | 35 mg/mL | PS80 0.07% (w/v) | Sucrose 1.75% (w/v) | Mannitol 1.05% (w/v) |
| 2 | Tris/Phosphate 3.5 mM | 7.0 | 35 mg/mL | PS80 0.07% (w/v) | Sucrose 1.75% (w/v) | Aspartate 1.05% (w/v) |
| 3 | Tris/Phosphate 3.5 mM | 7.0 | 35 mg/mL | PS80 0.07% (w/v) | Sucrose 1.75% (w/v) | Proline 1.05% (w/v) |
| 4 | Tris/Phosphate 3.5 mM | 7.0 | 35 mg/mL | PS80 0.07% (w/v) | Sucrose 1.75% (w/v) | Glycine 1.05% (w/v) |
| 5 | Tris/Phosphate 3.5 mM | 7.0 | 35 mg/mL | PS80 0.07% (w/v) | Sucrose 1.75% (w/v) | Arginine 1.05% (w/v) |

TABLE 17

Assay #P20- Additives screening and process development for a lyophilisate

| Form. #P20-x | Buffer system | pH | Strength | Additive 1 | Additive 2 | Additive 3 |
|---|---|---|---|---|---|---|
| 1 | Tris/Phosphate 10 mM | 7.0 | 175 mg/vial | PS80 0.1% (w/v) | Sucrose 5% (w/v) | Mannitol 3% (w/v) |
| 2 | Tris/Phosphate 10 mM | 7.0 | 175 mg/vial | PS80 0.1% (w/v) | Sucrose 5% (w/v) | Aspartate 3% (w/v) |
| 3 | Tris/Phosphate 10 mM | 7.0 | 175 mg/vial | PS80 0.1% (w/v) | Sucrose 5% (w/v) | Proline 3% (w/v) |
| 4 | Tris/Phosphate 10 mM | 7.0 | 175 mg/vial | PS80 0.1% (w/v) | Sucrose 5% (w/v) | Glycine 3% (w/v) |
| 5 | Tris/Phosphate 10 mM | 7.0 | 175 mg/vial | PS80 0.1% (w/v) | Sucrose 5% (w/v) | Arginine 3% (w/v) |

TABLE 18

Assay #P21- Additives screening at 35 mg/ml

| Form. #P21-x | Buffer system | pH | Concentration | Additives 1 | Additive 2 | Additive 3 |
|---|---|---|---|---|---|---|
| 1 | Tris/Phosphate 3.5 mM | 7.0 | 35 mg/ml | PS80 0.01% (w/v) | Sucrose 1% (w/v) | Mannitol 3% (w/v) |
| 2 | Tris/Phosphate 3.5 mM | 7.0 | 35 mg/ml | PS80 0.01% (w/v) | Sucrose 1% (w/v) | Sulfobutyl-ether-β-cydodextrine 3% (w/v) |
| 3 | Tris/Phosphate 3.5 mM | 7.0 | 35 mg/ml | PS80 0.01% (w/v) | Sucrose 1% (w/v) | N-acetyl-cystéine 3% (w/v) |
| 4 | Tris/Phosphate 3.5 mM | 7.0 | 35 mg/ml | PS80 0.01% (w/v) | Sucrose 1% (w/v) | Leucine 0.3% (w/v) |
| 5 | Tris/Phosphate 3.5 mM | 7.0 | 35 mg/ml | PS80 0.01% (w/v) | Sucrose 1% (w/v) | L-Lysine monochlorhydrate 3% (w/v) |

TABLE 18-continued

Assay #P21- Additives screening at 35 mg/ml

| Form. #P21-x | Buffer system | pH | Concentration | Additives 1 | Additive 2 | Additive 3 |
|---|---|---|---|---|---|---|
| 6 | Tris/Phosphate 3.5 mM | 7.0 | 35 mg/ml | PS80 0.01% (w/v) | Sucrose 1% (w/v) | N-acetyl-cysteine 0.03% (w/v) |
| 7c | Tris/Phosphate 3.5 mM | 7.0 | 35 mg/ml | PS80 0.01% (w/v) | Sucrose 1% (w/v) | Mannitol 3% (w/v) |
| 8 | Tris/Phosphate 3.5 mM | 7.0 | 35 mg/ml | PS80 0.01% (w/v) | — | — | cSame formulation as #P21-1 but this sample is inerted thanks to nitrogen while stored at 5° C.

The aim of these screenings was to find an additive to stabilize further the Lead Antibody with regard to HMW formation (assay #12, 15, 20-FDS, and 21). Due to the high sensitivity of the Lead Antibody to aggregation, the intended long term storage temperature (i.e., 5° C.) was found to be relevant to monitor the effect of the additives.

A Design of Experiment (DoE)-Screening model, first degree, D-optimal matrix—was done to screen the effect of different sugars, polyols, amino acids and solvents on HMW formation (assay #15). The outcome of this DoE is summarized in Table 19.

Figure 16:
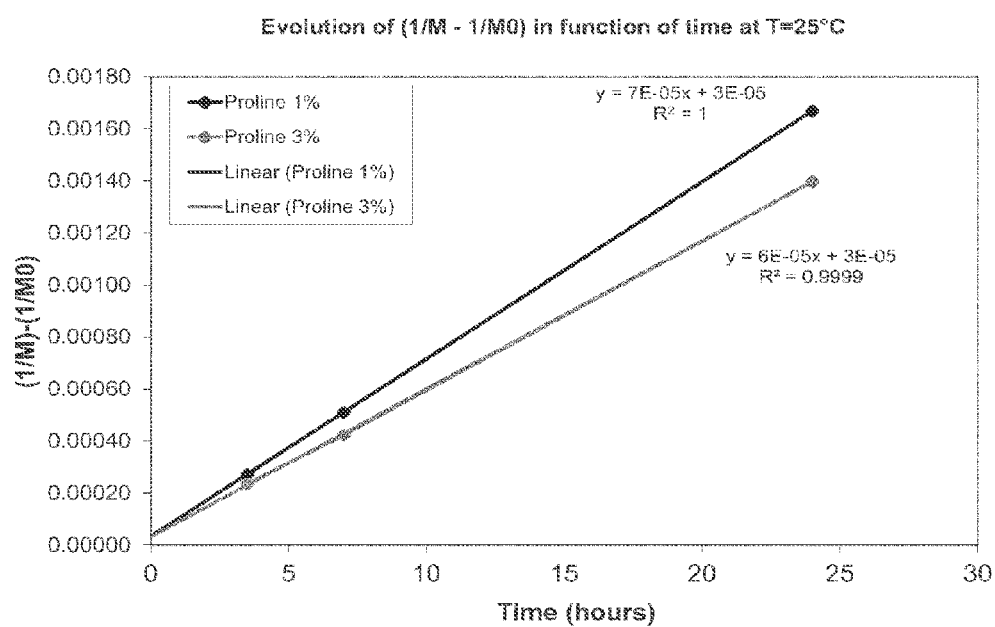
FIG. 16 is a graph of the inverse of the monomer content in function of time comparing 1% proline v. 3% proline in the lead formulation.

Next, various concentrations of proline were tested in the lead antibody formulation (see Table 23). Concentrations of 1% and 3% were tested. The samples were analysed by UPLC, and the results are shown in Tables 20 and 21, and in FIG. 16. Tables 20 and 21 show that either a proline concentration of 1 or 3% can be used in the formulation. These data also confirm the positive effect of proline on HMW kinetics. Furthermore, the cake is slightly more elegant (less retracted) with proline 3%, which confirms the role of proline as a ballast (results not shown).

TABLE 19

Outcome of assay #15 (DoE) regarding additives screening

| Parameters | HMW | DSC | Conclusion |
|---|---|---|---|
| Sugars and Polyols | Slight stabilisation by Mannitol | Slight stabilisation by Sucrose and Trehalose | Slight positive effect of sugars and polyols |
| Amino acids | Strong stabilisation by Aspartate and slight stabilisation by Glycine, Proline and Glutamine | Stabilisation by Aspartate and slightly by Glycine and Proline | Positive effect of Aspartate, Glycine and Proline |
| Solvents | Strong destabilisation by ethanol | Strong destabilisation by ethanol | No or destabilizing effect of solvents |
| Buffer systems | No effect | ND | No difference between buffer systems |

Figure 13:
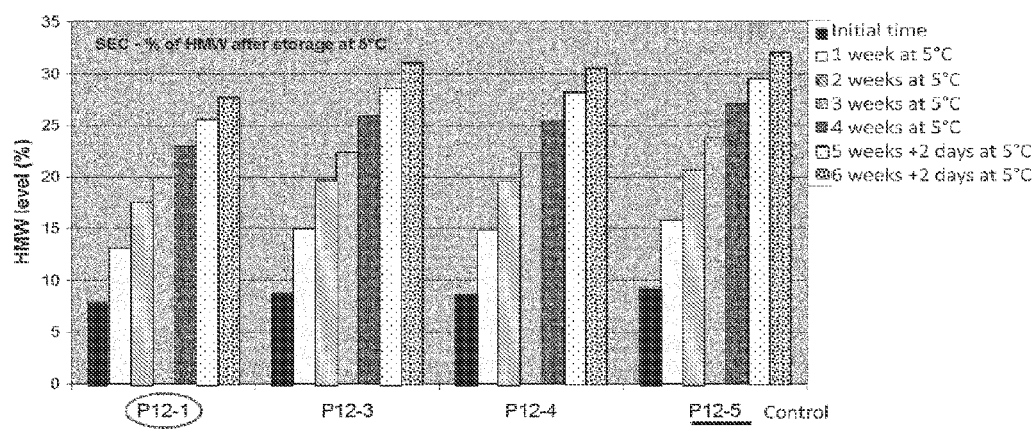
FIG. 13 is a graph showing HMW monitoring for assay #P12 (additive) while stored 6 weeks at 5° C.
Figure 14:
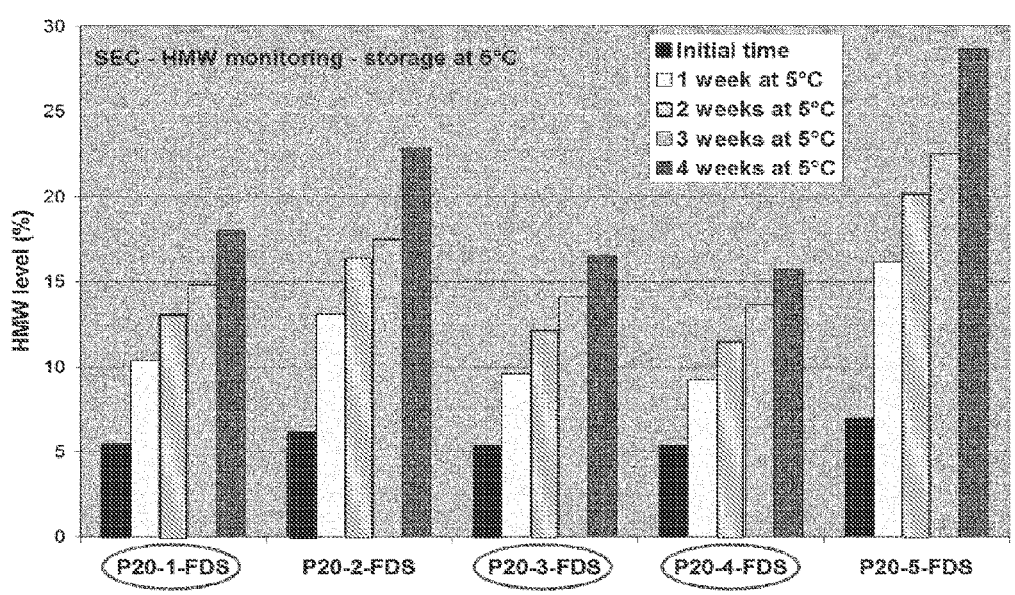
FIG. 14 is a graph showing HMW monitoring for assay #P20-FDS (additive) while stored 4 weeks at 5° C.

The additives found to have an effect on HMW were tested separately in assay #12 and 20-FDS:

Amino acids glycine (#P12-1 and P20-4-FDS) and proline (#P20-3-FDS) were found to have the best effect in minimizing HMW formation (see FIG. 13 and FIG. 14), Mannitol (#P20-1-FDS) came afterwards (see FIG. 14), Followed by sucrose (#P12-3) and trehalose (#P12-4), which were much less efficient (see FIG. 13), Finally, a positive effect of aspartate 8% (#P20-2-FDS) was not confirmed at a concentration of 4% (see FIG. 14).

Figure 15:
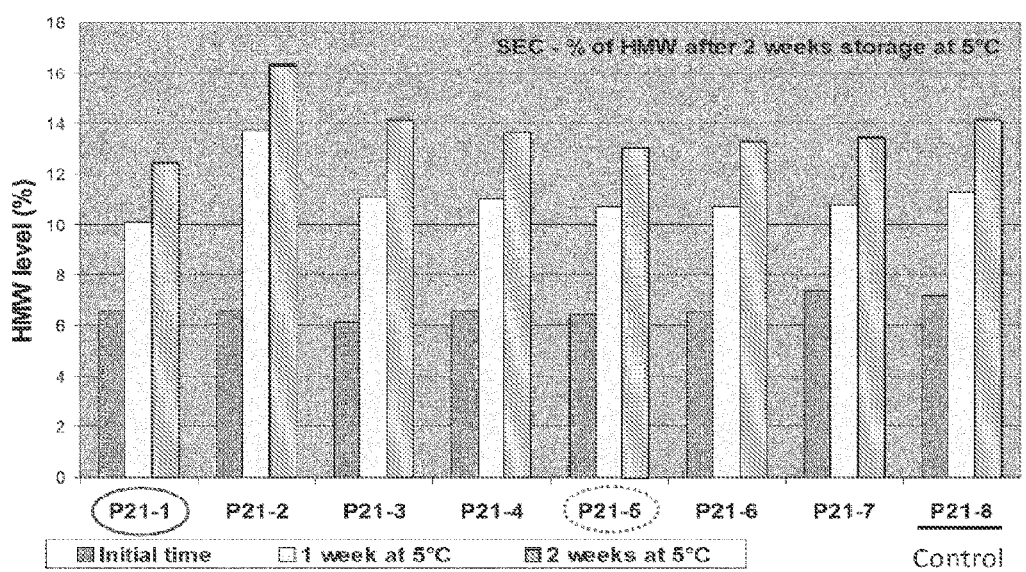
FIG. 15 is a graph showing HMW monitoring for assay #P21 (additive) while stored 2 weeks at 5° C.

Several other additives were tested during assay #21:

Lysine (#P21-5) was found to have a slight positive effect on HMW formation (see FIG. 15), Mannitol (#P21-1) was found to be the best in this assay.

It was found that the addition of proline to the formulation had two effects: it controlled HMW formation by reducing the rate of aggregation in the liquid formulation, and it acted as a bulking agent to make the cake more elegant in the lyophilized formulation. It was also found that the addition of mannitol to the lyophilized formulation caused the cake to be elegant.

TABLE 20

1% proline
F1 (1% proline)
stability n° 2

| Time (h) | % Monomer (M) | 1/M | 1/M-1/M0 | % HMW |
|---|---|---|---|---|
| 0 | 95.0 | 0.01053 | | 4.2 |
| 3.5 | 92.6 | 0.01080 | 0.00027 | 6.6 |
| 7 | 90.6 | 0.01104 | 0.00051 | 8.7 |
| 24 | 82.0 | 0.01220 | 0.00167 | 17.4 |

TABLE 21

3% proline
F5 (3% proline)
stability n° 2

| Time (h) | % Monomer (M) | 1/M | 1/M-1/M0 | % HMW |
|---|---|---|---|---|
| 0 | 95.3 | 0.01049 | | 3.8 |
| 3.5 | 93.2 | 0.01073 | 0.00024 | 6 |
| 7 | 91.6 | 0.01092 | 0.00042 | 7.8 |
| 24 | 84.1 | 0.01189 | 0.00140 | 15.1 |

In conclusion, although HMW formation has been significantly reduced by the addition of excipients, namely mannitol and amino acids such as glycine and proline, the beneficial effect at a Lead Antibody concentration of 100 mg/mL is not strong enough to achieve satisfactory shelf life. Hence a lyophilised formulation, along with a lyophilisation process has been developed.

Example 6—Lyophilized Formulations

For the freeze/drying process, 5 to 5.5 mL of the desired FDS prototype ranging from Lead Antibody concentration 20-38 mg/mL was dispensed into 15 mL vials (see as examples Table 13 and Table 14).

The freeze/drying process was done on pre-concentrated solution at 20 to 38 mg/mL in the close to final formulation of 5 to 5.5 mL dispensed into 15 mL vials.

Three different types of lyophilized systems from Usifroid have been used: PL45 (assay #14), SMH-300 (assay #17), and SMH-90 (assay #16, 18, 20). For details of the lyophilisation cycles see Table 22. The slope of temperature changing between lyophilisation steps is 1° C./min.

Figure 17:
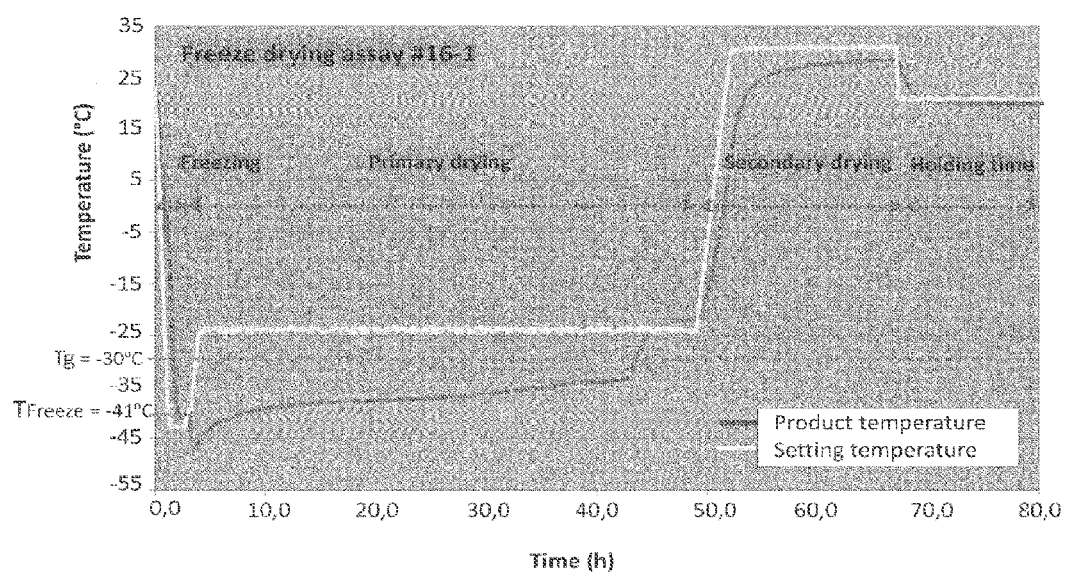
FIG. 17 is a graph following in temperature during a freeze drying process for formulation #P16-1.

Stability of Lead Antibody during the lyophilisation process
Stability of the reconstituted solution
Stability of the FDS (solution before lyophilisation)
Elegance of the cake
Reconstitution time
Stability of the cake The freeze drying cycle has been selected to avoid collapse of the cakes (see Table 22):

The freezing temperature has been set below the temperature of complete solidification i.e., slightly below the glass transition temperature (Tg'), which has been measured by DSC for each FDS candidate (solution before lyophilisation) (see FIG. 17).

The primary drying temperature has been set such that the temperature of the sample stays below the collapse temperature, which is close to Tg' (see FIG. 17).

Figure 18:
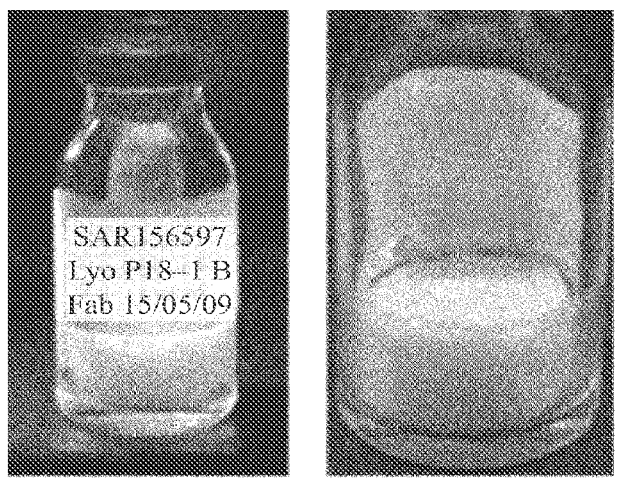
FIG. 18 shows pictures of #P18-1 cake in a 15 mL molded glass vial.

The cakes obtained during the various lyophilisation assays were all elegant (see FIG. 18) and the reconstitution

TABLE 22

Lyophilisation cycles used for each assay

| Assay # | Freezing Temp. $T_{Freeze}$ | Length at $T_{Freeze}$ | Primary drying Temp. | Duration of primary drying step[a] | Secondary drying Temp. | Duration of Secondary drying step | Holding time at 20° C.[b] |
|---|---|---|---|---|---|---|---|
| 14 | −45° C. | 100 min | −10° C. | 20 h | 30° C. | 7 h | 14 h |
| 16 | −42° C. | 60 min | −25° C. | 46 h | 30° C. | 18 h | 18 h |
| 17 | −45° C. | 60 min | −25° C. | 51 h | 30° C. | 21 h | 20 h |
| 18 | −42° C. | 60 min | −25° C. | 37 h | 30° C. | 18 h | 18 h |
| 20 | −42° C. | 60 min | −25° C. | 53 h | 40° C. | 18 h | 3 h |

[a]Set during the experiment according to the product temperature measurement
[b]The cycle is ended only during standard working time hours The dried substance obtained was then reconstituted at the target concentration of 100 mg/mL by adding the appropriate amount of WFI (1.0 to 1.6 mL).

For lyophilisation assays #P16-20, 1 mL FDS solutions were frozen at −20° C., thawed at room temperature once and then analyzed.

Freezing and thawing of intermediate DS (end of HAP step—BD) was also tested (assay #9). For this assay, 20 mL of DS in 50 mL HDPE Nalgene bottles were frozen at both −20° C. and −70° C., thawed at room temperature one time and then analyzed.

The following analytical methods were performed:
Visual inspection for appearance (clarity and color)
Light obscuration (HIAC) for quantification of sub-visible particles
SEC for protein purity
SDS-PAGE for protein purity
IEF for charge heterogeneity
FCM for quantification of sub-visible particles
DLS for aggregation
DSC for temperature of denaturation
SLS for colloidal stability
FT-IR spectroscopy for secondary structure
Fluorescence spectroscopy for tertiary structure
Karl ficher for residual water percentage determination (for lyophilisate)
XRPD for crystalline/amorphous matrix determination of the cake (for lyophilisate)

The main criteria for the selection of the formulations and lyophilisation process were: The following parameters were monitored:

time was within five minutes. Even if those parameters are important to monitor during the development, they were not relevant to discriminate between formulations.

During the freezing step, a cooling rate of 1° C./min was selected to avoid significant shifts in Lead Antibody concentration and pH. Secondary drying temperature was selected (see Table 22) to obtain a level of the residual water in the cake measured by Karl fisher below 1%.

Stabilization of Lead Antibody was assessed by SEC and SDS-PAGE for purity, and DLS and FCM for particle formation. The relevant criteria to discriminate between formulations were the level of HMW before and after reconstitution and sub-visible particles counting after reconstitution.

Figure 20:
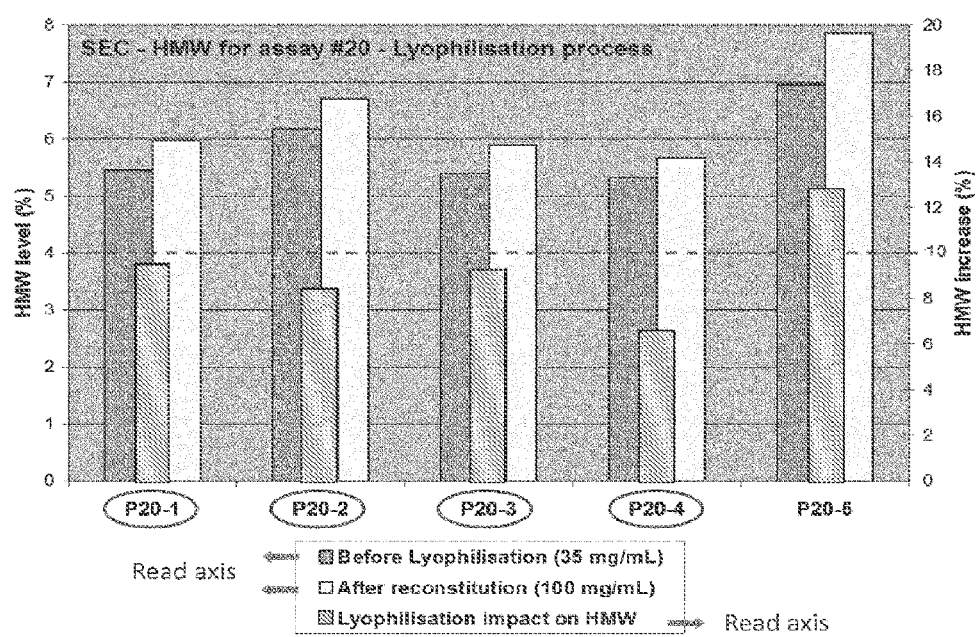
FIG. 20 is a graph showing HMW level for assay #P20 (additive) after lyophilisation.

To evaluate the impact of the lyophilisation process, the level of HMW before lyophilisation and after reconstitution was represented for each formulation, as well as the increase of this level—in percentage relative to the level before lyophilisation (see FIG. 19 and FIG. 20). A dotted line indicates on each figure an increase of 10%. Candidates providing a good stability were:

Phosphate with Sucrose 10%: #P14-2
Phosphate and Tris with Sucrose 5%+Mannitol 3%: #P14-3 and P14-8
Phosphate with Mannitol 3%+Glycine 1%: #P14-6
Tris/Phosphate with Sucrose 5%+Mannitol 3%: #P20-1
Tris/Phosphate with Sucrose 5%+Aspartate 3%: #P20-2
Tris/Phosphate with Sucrose 5%+Proline 3%: #P20-3
Tris/Phosphate with Sucrose 5%+Glycine 3%: #P20-4

Figure 21A:
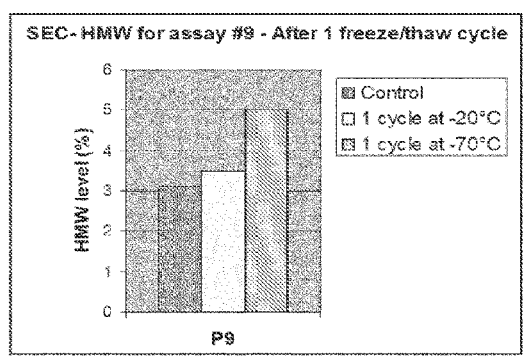
FIGS. 21A and 21B is a graph showing HMW level (a) and pictures (b) after a freeze/thaw cycle on non formulated DS (assay #9).
Figure 21B:
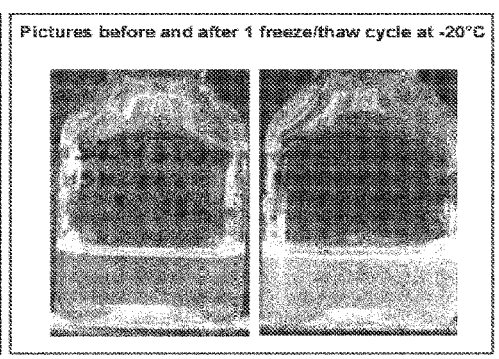

Note that without any excipients (#P14-1), the Lead Antibody is strongly unstable to the lyophilisation process, as an increase of around 130% was observed for HMW before and after lyophilisation. This result was expected as a freeze/thaw cycle done on the DS at −20° C. and −70° C. (assay #9) showed a strong destabilization of Lead Antibody (see FIG. 21)—freezing being the first step of lyophilisation process.

Regarding sub-visible particles, a comparison between the reconstituted solutions by FCM showed a better stability for the following candidates:

Tris/Phosphate with Sucrose 5%+Proline 3%: #P20-3
Tris/Phosphate with Sucrose 5%+Glycine 3%: #P20-4

Note: not determined for assay #14

To stabilize the Lead Antibody after reconstitution of the cake, excipients previously found to slow down aggregation were used (see Section regarding Excipients Screening for a Liquid Formulation). Stabilization of the Lead Antibody after reconstitution was assessed by SEC for purity, and DLS and FCM for particle formation. The relevant criteria to discriminate between formulations were:

The level of HMW 24 h after reconstitution (storage at 5° C.)

The number of particles after mechanical stress.

Figure 22:
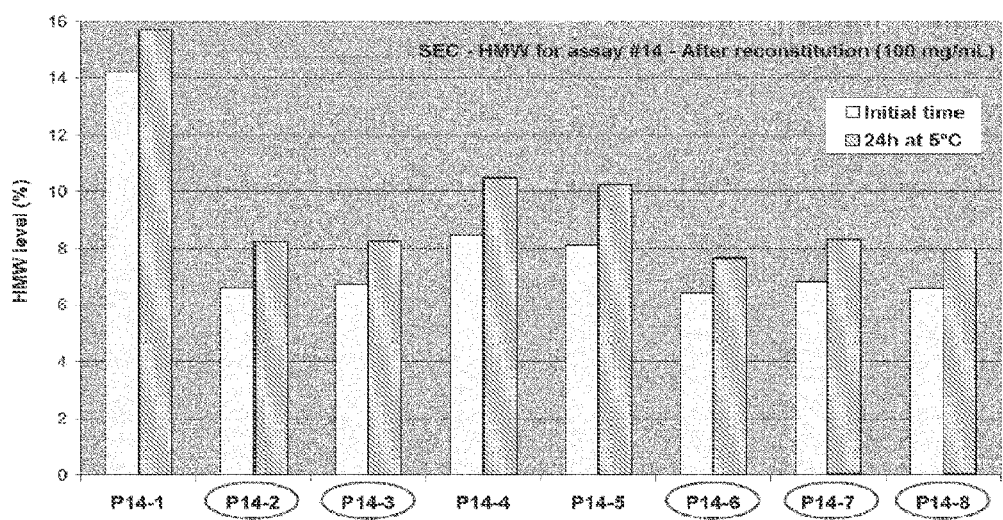
FIG. 22 is a graph showing HMW level for assay #P14 (additive) after reconstitution.
Figure 23:
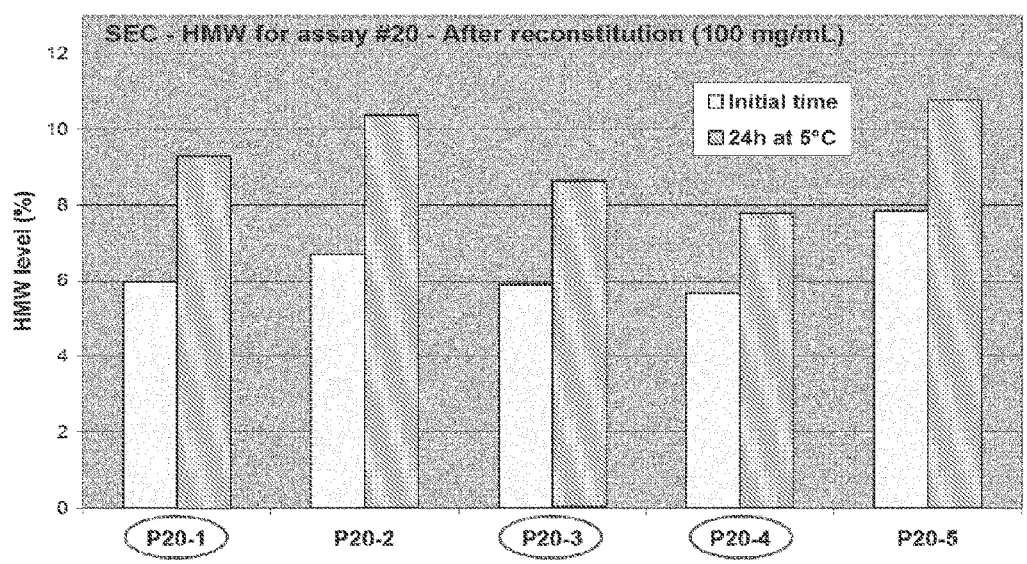
FIG. 23 is a graph showing HMW level for assay #P20 (additive) after reconstitution.

Regarding HMW formation 24 h after reconstitution (storage at 5° C.), candidates providing the best stability were (see FIG. 22 and FIG. 23):

Phosphate with Mannitol 3%+Glycine 1%: #P14-6
Tris/Phosphate with Sucrose 5%+Proline 3%: #P20-3
Tris/Phosphate with Sucrose 5%+Glycine 3%: #P20-4 followed by:

Phosphate with Sucrose 10%: #P14-2
Phosphate and Tris with Sucrose 5%+Mannitol 3%: #P14-3, P14-7 and P14-8
Tris/Phosphate with Sucrose 5%+Mannitol 3%: #P20-1

To evaluate the stability of the lyophilisate, the reconstitution was done immediately after manufacture and one month (assays #16-20) to two months (assays #18-20) afterwards. The lyophilisate candidates were stored at 5° C. (assay #16-20) and 20° C. (assay #17). Stability of the cake was assessed by SEC for purity, by FCM for particle formation, and by XRPD for cake structure.

Figure 24:
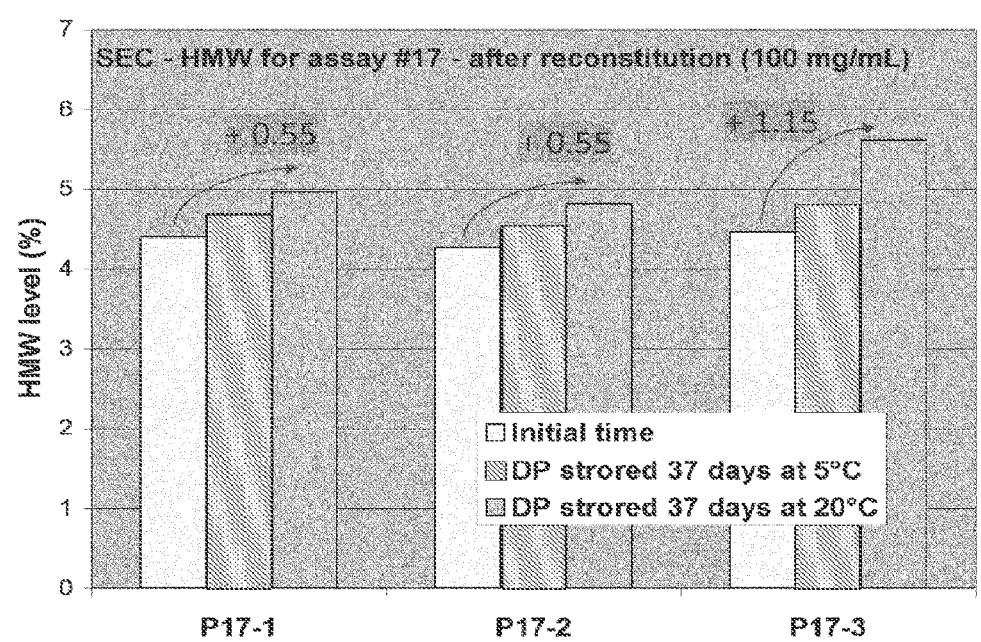
FIG. 24 is a graph showing HMW level for assay #P17 (additive) after cake storage and reconstitution.
Figure 25:
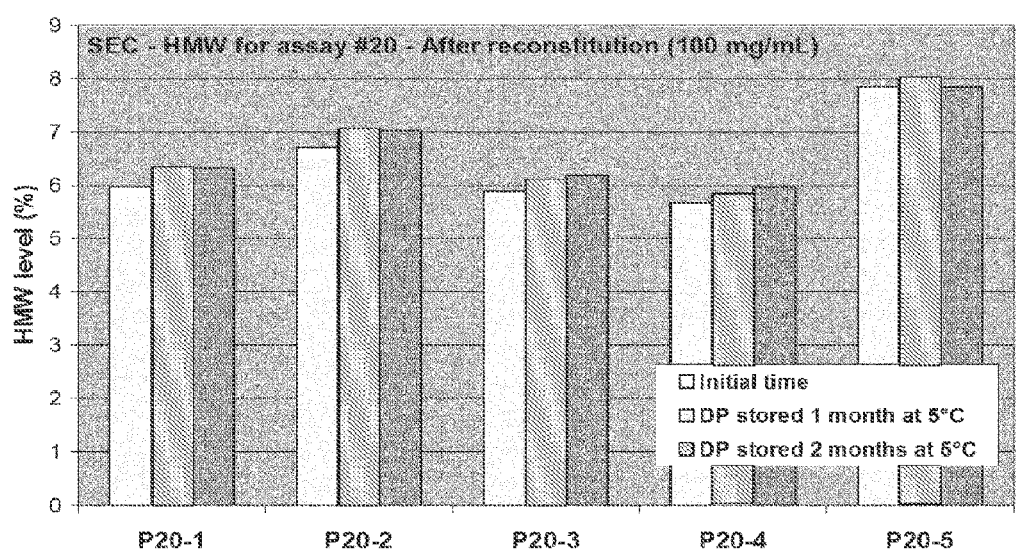
FIG. 25 is a graph showing HMW level for assay #P20 (additive) after cake storage and reconstitution.

Regarding HMW and visible/sub-visible particle formation, all of the formulations were found to be stable while stored at 5° C. (see FIG. 24 and FIG. 25). The slight increase in HMW level observed for both assays #17 and 20 after one month at 5° C. was not reproduced in the following assays (not shown). Furthermore, a slight increase in HMW level was observed while stored at 20° C. (see FIG. 24).

FDS stability, which is an important parameter to ensure a DP of quality, was taken into account for assays #16-18 and 20. Stabilization of the Lead Antibody at this stage of the process was assessed by SEC for purity, and DLS and FCM for particles formation. Storage at 5° C. was found to be relevant to monitor the effect of the additives on the stability of the Lead Antibody. One freeze/thaw cycle done on FDS was also relevant to discriminate between formulations.

Regarding stability of the Lead Antibody while stored at 5° C., results were described in the Section regarding Additives (see FIG. 14). The best stability was obtained for:

Tris/Phosphate with Sucrose 1.75%+Proline 1.05%: #P20-3-FDS
Tris/Phosphate with Sucrose 1.75%+Glycine 1.05%: #P20-4-FDS followed by:
Tris/Phosphate with Sucrose 1.75%+Mannitol 1.05%: #P20-1-FDS Regarding stability of the Lead Antibody after one freeze/thaw cycle, particle counting done by FCM showed that the following formulation candidates were stable:

Tris/Phosphate with Sucrose 1.67%+Mannitol 1%: #P17-2-FDS
Tris/Phosphate with Sucrose 1.75%+Mannitol 1.05%: #P20-1-FDS
Tris/Phosphate with Sucrose 1.75%+Proline 1.05%: #P20-3-FDS In conclusion, considering the following criteria: stability of the Lead Antibody during the process, aspect and stability of the cake as well as reconstitution time, stability of the reconstituted solution and of the FDS, 2 formulation candidates clearly stand out:

Tris/Phosphate with Sucrose 5%+Mannitol 3%
Tris/Phosphate with Sucrose 5%+Proline 3%

Conclusions for Examples 2-6

During the preformulation work, the formation of visible/sub-visible particles was managed due to the selection of a range of pH (>7.0), of a buffering system (Tris/Phosphate) and especially to the addition of a surfactant: polysorbate 80 at a concentration of 0.2%.

However, the formation of HMW was still an issue for a liquid formulation. Although HMW formation was significantly reduced by the selection of optimal pH (7.0), and some excipients (namely sucrose, mannitol, and amino acids such as glycine and proline), the beneficial effect at 100 mg/mL did not sufficiently prevent formation of HMW to expect a satisfactory shelf life for a liquid formulation.

Hence a lyophilised formulation was developed along with a lyophilisation process. To prevent aggregation during the lyophilisation process, a cryoprotectant was selected: sucrose at a concentration of 5%. The stabilizing excipients selected for the liquid formulation were tested in the lyophilisation process to better stabilize both the liquid before lyophilisation (concentration: 35 mg/mL) and the reconstituted solution (concentration: 100 mg/mL). A few of these excipients were compatible with the lyophilisation process and among them two have been selected: mannitol and proline at a concentration of 3%. The main criteria for the selection were: elegance and stability of the cake as well as stability of the FDS (solution before lyophilisation) and of the reconstituted solution.

The two formulation put in long term stability differ from one excipient (see Table 23):

Prototype 1: Proline
Prototype 2: Mannitol

TABLE 23

Description of the formulations

| Compound | Concentration | Function |
| --- | --- | --- |
| Lead Antibody | 100 mg/mL | Active ingredient |
| Tris/Phosphate | 10 mM | Buffer - pH 7.0 |
| Polysorbate 80 | 0.2% (p/v) | Stabilizing agent for visible/sub-visible particles |
| Sucrose | 5% (p/v) | Cryoprotectant + Stabilizing agent for HMW |
| Prototype 1: Proline 3% | 3% (p/v) | Stabilizing agent for HMW + Tonifiant agent |
| Prototype 2: Mannitol 3% | 3% (p/v) | Stabilizing agent for HMW + Tonifiant agent |

Additional Formulation Studies (Examples 7-8)

Abbreviations used in Examples 7-8 are:
DP: Drug Product
DS: Drug Substance
FD: Formulation Development
FDS: Formulated Drug Substance
FIM: First In Man
GRAS: Generally Recognized As Safe
HDPE: High Density Polyethylene
HMW: High Molecular Weight
IEF: IsoElectronic Focusing
IL: Interleukin
LMW: Low Molecular Weight
PC: Polycarbonate
PES: Polyethersulfone
PP: Polypropylene
PVDF: Polyvinylidene fluoride
RT: Room Temperature
SC: Sub Cutaneous
Td1: First Temperature of Denaturation
TOR: Time Out of Refrigeration Summary The aim of these studies (Examples 7-8) was to improve the FDS stability regarding the high propensity for HMW formation of the Lead Antibody in the liquid state.

The study plan was defined based on prior knowledge acquired in the pre-formulation studies (Examples 2-6) and is focused on kinetics of HMW formation at room temperature, in the FDS at 35 mg/mL.

All buffers and excipients used were already used either in marketed antibody products or in other products for parenteral use, in particular they are all GRAS (Generally Recognized As Safe). The pH ranges between 6.2 and 7.4.

A total of 50 different formations were compared side by side with the formulation described Table 23. The main conclusions were:
- pH values around 6.2 decreases Lead Antibody solubility: a gel formation and a precipitation were observed with Succinate and Histidine respectively
- In addition, Histidine should be avoided at pH 6.6 as the solution was opalescent and slightly less thermally stable
- In the range of pH between 6.6 to 7.4, there was no clear pH effect on HMW formation kinetic
- Increasing ionic strength had a destabilizing effect on HMW formation kinetics
- Phosphate and Citrate were the best buffers tested, provided they were at low concentration such as 1.75 mM
- Among all the excipients tested, the best stabilizing effect was obtained with Glycine 10 and 72 mM, and Sucrose 2.4%. However, the stabilizing effect did not allow us to significantly slow down the HMW formation In conclusion, the results in Examples 7-8 did not identify a new combination of excipients that could improve significantly the formulations described in Table 23 regarding HMW formation. The recommendation was to keep the following formulation (see Table 24): Phosphate 6.5 mM/Tris 3.7 mM, pH 7.0, PS80 0.2% (w/v), Sucrose 5% (w/v), Proline 3% (w/v).

TABLE 24

| Formulation description | |
|---|---|
| Component | Concentration |
| Lead Antibody | 100 mg/mL |
| Phosphate | 6.5 mM |
| Tris | 3.7 mM |
| Sucrose | 5% (w/v) |
| Proline | 3% (w/v) |
| PS80 | 0.2% (w/v) |

Introduction

The Lead Antibody is an engineered humanized bispecific antibody (BsAb) that targets the cytokines IL-4 and IL-13. Its molecular weight, as determined by mass spectrometry, is 198 kDa, and its Ip, as determined by IEF ranges between 5.8 to 6.2.

Major manufacturing DS process changes are being implemented for phase IIb and a comparability study is planned between phase I/IIa and phase IIb DS and DP quality. As part of the DS manufacturing changes, it was decided to perform a formulation study with the aim to reduce the HMW formation in the liquid state. Thus, the potential improvement of the formulation could be included in the comparability study.

Note that in the same time, the DP manufacturing process for phase IIb is being optimized for scale-up, FDS thawing, and DP dose/vial change to 100 mg/7 mL vial instead of 150 mg/15 mL vial. This study is being conducted in parallel with the formulation development.

The current target product profile for this study (Examples 7-8) stipulates the following characteristics of the drug product:
Route of administration: SC injection
DP form: lyophilized
Concentration: solution reconstituted at 100 mg/mL
Shelf-life: 24 months
Temperature of storage: 2° C.-8° C.
Dose strength: 100 mg/vial
Primary container: 7 mL type 1 tubing clear glass vial The drug substance should be formulated at 35 mg/mL prior to storage at −20° C. in 1 L polycarbonate bottles. No additional excipients or dilutions are performed prior to freeze-drying.

Pre-formulation and formulation studies for FIM allowed the following conclusions:
- Avoid acidic pH<6.0 (low thermal and colloidal stability) and basic pH >7.5 (LMW formation and charge isoforms change under thermal stress).
- Visible/sub-visible particles were significantly reduced by using polysorbate 80 at a concentration of 0.2% in combination with the buffering system Phosphate/Tris, pH 7.0
- The HMW formation kinetic increases with Lead Antibody concentration, and the tested formulations did not sufficiently prevent HMW formation at 100 mg/mL for us to expect a satisfactory shelf life for a liquid formulation.
- HMW formation in the liquid state drove the development toward a lyophilized DP reconstituted with slightly less than ⅓ of the initial volume (before lyophilisation) to achieve 100 mg/mL from a 35 mg/mL FDS. A cryoprotectant and lyoprotectant were selected: Sucrose at a concentration of 5%.
- The formulation selected for phase I and IIa was the following: Phosphate 6.5 mM/Tris 3.7 mM, pH 7.0, PS80 0.2% (w/v), Sucrose 5% (w/v), Proline 3% (w/v).
- This formulation might be optimized regarding HMW formation by combining the excipients identified as having a slight positive effect, namely: Sucrose, Mannitol, and amino acids such as Glycine and Proline.

HMW formation in the liquid state has been identified as being the major path of degradation. The kinetic increases with the temperature of the solution (10 times slower at 5° C. than at RT in the DP) and with Lead Antibody concentration:

FDS at 35 mg/mL at RT: ΔHMW=+1.6% in 7 h and +4.1% in 24 h

DP at 100 mg/mL at RT: ΔHMW=+0.6% in 1 h and +3.5% in 5 h

Objectives

The objective of this study (Examples 7-8) was to increase the stability of the Lead Antibody in the liquid state with respect to HMW formation. In order to set quantitative targets for this study, the following values were proposed:

5 h at RT after DP reconstitution for in-use stability: ΔHMW<+1% in 5 h, 12 h of TOR for the FDS in order to ease DP manufacture: ΔHMW<+1% in 12 h.

These target values take into account the conditions of use of the reconstituted DP at 100 mg/mL and the process manufacturing conditions when the FDS at 35 mg/mL is out of refrigerated conditions. These values should be adjusted depending on the Quality Target Product Profile.

Study Design

The approach proposed for this study (Examples 7-8) was to screen the combined excipients over a wide range of formulations at Lead Antibody concentrations of 35 mg/mL.

The screening of formulations was focused on stabilizing excipients that could potentially impact the HMW formation. It was decided for this study the following:

PS80 and Sucrose at the formulation phase I concentrations were kept in the screening as no negative impact on HMW formation at these concentrations had been demonstrated and a strong positive impact on manufacturing process and/or reconstitution had been observed.

The pH range was tightened between 6.2 and 7.4 because previous studies had shown the benefit of keeping the pH around pH 7

The 5 injectable buffers within this pH range were screened, alone or in combination with several excipients: other buffering systems and/or additives (amino acids, sucrose (in addition to what was already contained in the phase I formulation) and salts mainly).

Drug Substance

DS used in this study (Examples 7-8) are described Table 25.

TABLE 25

| | | | | | | | |
|---|---|---|---|---|---|---|---|
| | | | | DS description | | | |
| Batch number # | Type | Manuf. date | Manufacturer | Formulation | Concentration | Storage | Used for assays |
| LT-10006-DS | FDS | | | Phosphate 2.22 mM/Tris 1.28 mM, Sucrose 1.75%, Proline 1.05%, PS80 0.07% | 33 mg/mL | −20° C. | H04-150 to 190 |
| VAB-YKR1-000079 | DS | | | Sucrose 2.1% | 42 mg/mL | −20° C. | H04-193 |

Drug Product

DP used in this study (Examples 7-8) were formulated with formulation phase I/IIa (Phosphate 6.5 mM/Tris 3.7 mM, pH 7.0, PS80 0.2%, Sucrose 5%, Proline 3%) (see Table 26).

TABLE 26

| | | | | |
|---|---|---|---|---|
| | | | DP description | |
| DP Lyophilisate # | Manuf. date | Manufacturer | Strength/Format | From the FDS # |
| H04-016 | | | 150 mg/15 mL vial | CER0315 and CER0375 |
| H04-046 | | | 150 mg/15 mL vial | CER0378, CER0382 and CER0392 |
| C1016207 | | | 150 mg/15 mL vial | GMP2 |
| H04-193 | | | 100 mg/7 mL vial | H04-193 |

Formula(S)

Formulas for each assay in Examples 7-8 are listed below in Table 27.

TABLE 27

| | | | |
|---|---|---|---|
| | | Formula | |
| Formulation assay # | Buffer system | pH Nominal composition of excipienta | Nominal concentration (mg/mL) |
| H04-150 A1 | Succinate 10 mM | 6.2 Sucrose 1.75% - PS80 0.07% | 36.25 |
| H04-150 A2 | Succinate 10 mM | 6.2 Tris 10 mM - Sucrose 1.75% - PS80 0.07% | 36.25 |
| H04-150 A3 | Succinate 10 mM | 6.2 Histidine 10 mM - Sucrose 1.75% - PS80 0.07% | 36.25 |

TABLE 27-continued

Formula

| Formulation assay # | Buffer system | pH | Nominal composition of excipienta | Nominal concentration (mg/mL) |
|---|---|---|---|---|
| H04-150 A4 | Succinate 10 mM | 6.2 | Proline 10 mM - Sucrose 1.75% - PS80 0.07% | 36.25 |
| H04-150 A5 | Succinate 10 mM | 6.2 | Glycine 10 mM - Sucrose 1.75% - PS80 0.07% | 36.25 |
| H04-150 A6 | Succinate 10 mM | 6.2 | Tris 10 mM - Glycine 10 mM - Sucrose 1.75% - PS80 0.07% | 36.25 |
| Preliminary test (P-H04-144) | Histidine 10 mM | 6.2 | Sucrose 1.75% - PS80 0.07% | 36.25 |
| Preliminary test (P-H04-148) | Histidine 10 mM | 6.2 | Glycine 10 mM - Sucrose 1.75% - PS80 0.07% | 36.25 |
| H04-150 B1 | Histidine 10 mM | 6.6 | Sucrose 1.75% - PS80 0.07% | 36.25 |
| H04-150 B2 | Histidine 10 mM | 6.6 | Tris 10 mM - Sucrose 1.75% - PS80 0.07% | 36.25 |
| H04-150 B3 | Histidine 10 mM | 6.6 | Proline 10 mM - Sucrose 1.75% - PS80 0.07% | 36.25 |
| H04-150 B4 | Histidine 10 mM | 6.6 | Glycine 10 mM - Sucrose 1.75% - PS80 0.07% | 36.25 |
| H04-150 C | — | 6.8 | Sucrose 2.1% - PS80 0.07% | 36.25 |
| H04-150 D | Phosphate 3.33 mM/ Tris 1.92 mM | 6.9 | Sucrose 8.42% - PS80 0.07% | 36.25 |
| H04-163 A1 | Citrate 10 mM | 6.6 | Sucrose 1.75% - PS80 0.07% | 36.25 |
| H04-163 A2 | Citrate 10 mM | 6.6 | Tris 10 mM - Sucrose 1.75% - PS80 0.07% | 36.25 |
| H04-163 A3 | Citrate 10 mM | 6.6 | Histidine 10 mM - Sucrose 1.75% - PS80 0.07% | 36.25 |
| H04-163 A4 | Citrate 10 mM | 6.6 | Proline 10 mM - Sucrose 1.75% - PS80 0.07% | 36.25 |
| H04-163 A5 | Citrate 10 mM | 6.6 | Glycine 10 mM - Sucrose 1.75% - PS80 0.07% | 36.25 |
| H04-163 A6 | Citrate 10 mM | 6.6 | Tris 10 mM - Glycine 10 mM - Sucrose 1.75% - PS80 0.07% | 36.25 |
| H04-163 B1 | Phosphate 10 mM | 6.6 | Sucrose 1.75% - PS80 0.07% | 36.25 |
| H04-163 B2 | Phosphate 10 mM | 7.0 | Sucrose 1.75% - PS80 0.07% | 36.25 |
| H04-163 B3 | Phosphate 10 mM | 7.0 | Tris 10 mM - Sucrose 1.75% - PS80 0.07% | 36.25 |
| H04-163 B4 | Phosphate 10 mM | 7.0 | Histidine 10 mM - Sucrose 1.75% - PS80 0.07% | 36.25 |
| H04-163 B5 | Phosphate 10 mM | 7.0 | Proline 10 mM - Sucrose 1.75% - PS80 0.07% | 36.25 |
| H04-163 B6 | Phosphate 10 mM | 7.0 | Glycine 10 mM - Sucrose 1.75% - PS80 0.07% | 36.25 |
| H04-172 A1 | Tris 10 mM | 7.0 | Sucrose 1.75% - PS80 0.07% | 36.25 |
| H04-172 A2 | Tris 10 mM | 7.4 | Sucrose 1.75% - PS80 0.07% | 36.25 |
| H04-172 A3 | Tris 10 mM | 7.4 | Succinate 10 mM NaCl 7.5 mM - Sucrose 1.75% - PS80 0.07% | 36.25 |
| H04-172 A4 | Tris 10 mM | 7.0 | Histidine 10 mM - Sucrose 1.75% - PS80 0.07% | 36.25 |
| H04-172 A5 | Tris 10 mM | 7.4 | Histidine 10 mM - Sucrose 1.75% - PS80 0.07% | 36.25 |
| H04-172 A6 | Tris 10 mM | 7.4 | Glycine 10 mM - Sucrose 1.75% - PS80 0.07% | 36.25 |
| H04-172 B1 | Phosphate 1.75 mM | 7.0 | Sucrose 1.75% - PS80 0.07% | 36.25 |
| H04-172 B2 | Phosphate 1.75 mM | 7.0 | Sucrose 4% - PS80 0.07% | 36.25 |
| H04-185 A1 | — | 6.8 | Sucrose 4.15% - PS80 0.07% | 36.25 |
| H04-185 A2 | — | 6.8 | Glycine 72 mM - Sucrose 1.75% - PS80 0.07% | 36.25 |
| H04-185 B1 | Phosphate 1.75 mM | 6.8 | Glycine 72 mM - Sucrose 1.75% - PS80 0.07% | 36.25 |
| H04-185 B2 | Phosphate 1.75 mM | 6.8 | Sucrose 4.15% - PS80 0.07% | 36.25 |
| H04-185 B3 | Phosphate 1.75 mM | 6.8 | Sodium benzoate 37.8 mM - Sucrose 1.75% - PS80 0.07% | 36.25 |
| H04-185 B4 | Phosphate 1.75 mM | 6.8 | NaCl 38.5 mM - Sucrose 1.75% - PS80 0.07% | 36.25 |
| H04-185 B5 | Phosphate 5.25 mM | 6.8 | Glycine 72 mM - Sucrose 1.75% - PS80 0.07% | 36.25 |
| H04-185 C1 | Citrate 5.25 mM | 6.8 | Glycine 72 mM - Sucrose 1.75% - PS80 0.07% | 36.25 |
| H04-185 C2 | Citrate 1.75 mM | 6.8 | Glycine 72 mM - Sucrose 1.75% - PS80 0.07% | 36.25 |
| H04-185 C3 | Citrate 1.75 mM | 6.8 | Sucrose 4.15% - PS80 0.07% | 36.25 |
| H04-185 C4 | Citrate 10 mM | 6.8 | Glycine 72 mM - Sucrose 1.75% - PS80 0.07% | 36.25 |
| H04-185 D | Phosphate 2.22 mM/ Tris 1.28 mM | 6.8 | Proline 91 mM - Sucrose 1.75% - PS80 0.07% | 36.25 |
| H04-187 A1 | Phosphate 2.22 mM/ Tris 1.28 mM | 6.7 | Proline 91 mM - Sucrose 1.75% - PS80 0.07% | 36.25 |
| H04-187 A2 | Phosphate 2.22 mM/ Tris 1.28 mM | 6.8 | Proline 91 mM - Sucrose 1.75% - PS80 0.07% | 36.25 |
| H04-187 A3 | Phosphate 2.22 mM/ Tris 1.28 mM | 7.0 | Proline 91 mM - Sucrose 1.75% - PS80 0.07% | 36.25 |
| H04-187 A4 | Phosphate 2.22 mM/ Tris 1.28 mM | 7.2 | Proline 91 mM - Sucrose 1.75% - PS80 0.07% | 36.25 |
| H04-190 A1 | — | 6.8 | Sucrose 20.5% - PS80 0.07% | 20 |
| H04-190 A2 | — | 6.8 | Sucrose 13.42% - PS80 0.07% | 36.25 |
| H04-190 A2 | — | 6.8 | Sucrose 1.75% - PS80 0.07% | 36.25 | aExcipients quantities are expressed in % of w/v

Manufacture Process

The formulations in Examples 7-8 were manufactured with a concentrated solution of Lead Antibody that was obtained by UF/DF at a concentration of 42 mg/mL in sucrose 2.1%. This Lead Antibody solution was diluted with concentrated stock solutions of excipients.

UF/DF Process

During the UF/DF process (Examples 7-8), the initial protein solution at 35 mg/mL was first concentrated to 40 mg/mL, the buffer was then exchanged. After the diafiltration, the protein solution was concentrated higher than 42 mg/mL, which was the target final concentration (see Table 28).

The material used and the process conditions of each UF/DF are described Table 28. At the end of the UF/DF, the Lead Antibody concentration was adjusted to 42 mg/mL in a Sucrose 2.1% solution.

TABLE 28

UF/DF manufacturing parameters

| Formulation assays # | Membrane | Ratio: g of protein/$m^2$ membrane (g/$m^2$) | Protein concentration during diafiltration (mg/mL) | Number of diafiltration volume passed | Buffer exchange | Protein concentration at the end of the UF/DF (mg/mL) |
|---|---|---|---|---|---|---|
| H04-137 | Pellicon 3 ® 0.11 $m^2$ | 216 | 40 | 9 | Sucrose 2.1% | 48.5 |

Formulation Adjustment

Lead Antibody post UF/DF solution (Examples 7-8) was diluted with appropriate amounts of concentrated stock solutions up to the desired final formulation. The reference and composition of the concentrated solutions manufactured for this study are summarized in Table 29.

TABLE 29

Concentrated stock solution recipes

| Formulation assay # | Buffer system | Nominal composition of excipient[a] | pH adjusted to |
|---|---|---|---|
| P-H04-138 | Succinate 60 mM | — | 5.9 |
| P-H04-139 | Succinate 60 mM | Tris 60 mM | 5.9 |
| P-H04-140 | Succinate 60 mM | Histidine 60 mM | 6.2 |
| P-H04-141 | Succinate 60 mM | Proline 60 mM | 5.9 |
| P-H04-142 | Succinate 60 mM | Glycine 60 mM | 5.9 |
| P-H04-143 | Succinate 60 mM | Tris 60 mM—Glycine 60 mM | 5.9 |
| P-H04-144 | Histidine 60 mM | — | 6.1 |
| P-H04-145 | Histidine 60 mM | — | 6.6 |
| P-H04-146 | Histidine 60 mM | Tris 60 mM | 6.4 |
| P-H04-147 | Histidine 60 mM | Proline 60 mM | 6.5 |
| P-H04-148 | Histidine 60 mM | Glycine 60 mM | 6.1 |
| P-H04-149 | Histidine 60 mM | Glycine 60 mM | 6.6 |
| (H04-150) | Phos 20 mM/Tris 11.5 mM | Sucrose 40% | No adjustment |
| P-H04-151 | Citrate 60 mM | — | 6.4 |
| P-H04-152 | Citrate 60 mM | Tris 60 mM | 6.3 |
| P-H04-153 | Citrate 60 mM | Histidine 60 mM | 6.6 |
| P-H04-154 | Citrate 60 mM | Proline 60 mM | 6.4 |
| P-H04-155 | Citrate 60 mM | Glycine 60 mM | 6.4 |
| P-H04-156 | Citrate 60 mM | Tris 60 mM—Glycine 60 mM | 6.2 |
| P-H04-157 | Phosphate 60 mM | — | 6.4 |
| P-H04-158 | Phosphate 60 mM | — | 7 |
| P-H04-159 | Phosphate 60 mM | Tris 60 mM | 6.9 |
| P-H04-160 | Phosphate 60 mM | Histidine 60 mM | 7 |
| P-H04-161 | Phosphate 60 mM | Proline 60 mM | 7 |
| P-H04-162 | Phosphate 60 mM | Glycine 60 mM | 6.8 |
| P-H04-164 | Tris 60 mM | — | 7.3 |
| P-H04-165 | Tris 60 mM | — | 7.7 |
| P-H04-166 | Tris 60 mM | Succinate 60 mM NaCl 45 mM | 7.7 |
| P-H04-167 | Tris 60 mM | Histidine 60 mM | 7.2 |
| P-H04-168 | Tris 60 mM | Histidine 60 mM | 7.5 |
| P-H04-169 | Tris 60 mM | Glycine 60 mM | 7.6 |
| P-H04-170 | Phosphate 10.5 mM | — | 7.2 |
| P-H04-171 | Phosphate 10.5 mM | Sucrose 13.5% | 7.2 |
| P-H04-173 | — | Sucrose 14.4% | No adjustment |
| P-H04-174 | — | Glycine 432 mM | No adjustment |
| P-H04-175 | Phosphate 10.5 mM | Glycine 432 mM | 6.8 |
| P-H04-176 | Phosphate 10.5 mM | Sucrose 14.4% | 6.8 |
| P-H04-177 | Phosphate 10.5 mM | Sodium benzoate 227 mM | 6.8 |
| P-H04-178 | Phosphate 10.5 mM | NaCl 231 mM | 6.8 |
| P-H04-179 | Phosphate 31.5 mM | Glycine 432 mM | 6.8 |
| P-H04-180 | Citrate 31.5 mM | Glycine 432 mM | 6.8 |

TABLE 29-continued

Concentrated stock solution recipes

| Formulation assay # | Buffer system | Nominal composition of excipient[a] | pH adjusted to |
|---|---|---|---|
| P-H04-181 | Citrate 10.5 mM | Glycine 432 mM | 6.8 |
| P-H04-182 | Citrate 10.5 mM | Sucrose 14.4% | 6.8 |
| P-H04-183 | Citrate 60 mM | Glycine 432 mM | 6.8 |
| P-H04-184 | Phos 13.3 mM/Tris 7.7 mM | Proline 547 mM | 7 |
| P-H04-186 | Phos 13.3 mM/Tris 7.7 mM | Proline 547 mM | 6.5 |
| P-H04-189 1 | — | Sucrose 37.5% | No adjustment |
| P-H04-189 2 | — | Sucrose 70% | No adjustment |

[a]Excipients quantities expressed in % are in w/v

Each formulation was sterile filtered (Millex® GV) under laminar flow and a fraction was dispensed into a 2 mL type I glass vial as appropriate (1 to 2 mL) and stoppered for each stability time point.

Stress Conditions

Thermal Stress

The thermal stress conditions performed in Examples 7-8, according to formulation assays, are listed in Table 30.

TABLE 30

Thermal stress conditions

| Formulation assays # | Temperature stress | Time of stress |
|---|---|---|
| H04-150 | RT[a] | Days: 1, 2 and 3 |
|  | 5° C.[b] | Days: 2, 3 and 6 |
| H04-163 | RT[a] | Days: 1, 2 and 3 |
|  | 5° C.[b] | Days: 2, 3 and 7 |
| H04-172 | RT[a] | Days: 1, 2, 3 and 6 |
|  | 5° C.[b] | Days: 2, 3 and 6 |
| H04-185 | RT[a] | Days: 1, 2 and 3 |
|  | 5° C.[b] | Days: 2, 3 and 6 |
| H04-187 | RT[a] | 16 h, 24 h and 40 h |
| H04-190 | RT[a] | 16 h, 40 h and 48 h |
| H04-193 | 5° C.[c] | 21 h, 30 h and 46 h |
|  | 25° C.[c] | 21 h, 30 h and 46 h |

[a]Due to laboratory air conditioning, RT ranges between 21° C. and 29° C.
[b]Performed in a standard non GMP refrigerated chamber
[c]GMP thermostic chamber Analytical Methods Description The following analytical methods were performed in Examples 7-8:

Visual inspection for appearance (clarity and color)
Solution in 7 mL vials were observed with natural light
HPLC-SEC for protein purity
2 Columns PROSEC 300S-250×4 6 mm at 35° C.
Mobile phase: Phosphate 0.1 M/NaCl 0.2 M pH 7.0
Detection: 280 nm
Injection: 10 µL (concentration 5 mg/mL)
Flow: 0.2 mL/min
Total run time: 40 min The following analytical method was performed:
UPLC-SEC for protein purity
Column: 1 Acquity BEH200 SEC (150×4.6 mm dp=1.7 µm) at 40° C.
Mobile phase: $Na_2HPO_4$ 50 mM/$NaClO_4$ 300 mM at pH 7.0
Detection: UV at 280 nm
Injection: 1 µL (solution at 5 mg/mL) Standard 3014ET
Injection: 2 µL (solutions at 2.0 mg/mL)
Flow: 0.3 mL/min
Total run time: 8 min The following analytical method was monitored:
DSC for temperature of denaturation:
Differential Scanning calorimetry (DSC) was used to estimate the thermal stability of the antibody in different formulations.
calorimetric measurements were performed with a VP-Capillary DSC from 25° C. to 100° C. with a heating rate of 1° C./min
The capacity curve gave information about the denaturation temperature Td (° C.) (peak maximum).

Criteria of Evaluation

SEC: The results were considered comparable when the difference was equal or less than 0.5% of HMW.
DSC: The results were considered comparable when the difference on Td1 was equal or less than 0.4° C.

UPLC Vs HPLC Method

The first screening (assays #H04-150 to 172) had been performed on the HPLC method developed for phase I. An issue regarding a drifting of the baseline that impacted HMW level determination had been observed when a high number of samples were analyzed in a row.

For the second screening (assays #H04-185 to 190), in order to obtain a precise HMW level evolution, a UPLC method was used for which no baseline drifting had been observed. The same chromatographic profile of the standard was observed even after more than 200 samples were injected on the same column.

References for SEC Measurements

In order to compare the different series regarding the HMW evolution over time, the formulation phase I was used as a reference:

For the first screening (assays #H04-150 to 172), the FDS phase I was obtained, for each of the 3 series, by reconstitution with WFI at 35 mg/mL of DP lyophilisate #H04-016.

For the second screening (assays #H04-185 to 190), in addition to the previous FDS phase I (H04-016), another FDS phase I freshly manufactured along with the tested formulations was used, for each of the 3 series. Furthermore, a 3rd FDS phase I reference (#LT-10006-DS) was used: the FDS not freeze-dried, but only thawed.

Unexpectedly, HMW kinetics appeared different between the various references. For comparison, two additional DP lyophilisates had been tested along with the DP lyophilisate #H04-016. The difference within the DP lyophilisate became significant after 40 h at RT. However, the thawed reference, #LT-10006-DS was significantly different from all of the DP lyophilisate, from 16 h at RT. The DP lyophilisate presented faster HMW kinetics than the thawed reference, #LT-10006-DS, and thus can not be used to compare the formulations manufactured in this study (formulations for this study were manufactured from thawed FDS (see Section regarding Manufacture Process) to the formulation phase I/IIa.

Using the same batch and freshly prepared freeze-dried DP, no significant difference on HMW kinetics was observed between the thawed FDS and the DP lyophilisate. Thus, the HMW kinetics observed on the formulations freshly manufactured for this study would be observed as well on the same formulations after freeze-drying.

The conclusion drawn from those assays can not be generalized to all DP lyophilisate and all thawed FDS. The comparison of HMW kinetics between different batches may depend on various parameters and will need a specific and separate study.

Results and Discussion

All formulations manufactured in Examples 7-8 contained at least 1.75% (w/v) of sucrose and close to 0.07% (w/v) of PS80. These concentrations are nominal values and are based on the dilution factor applied to the Lead Antibody starting solution. Regarding PS80 concentration, the assumption was made that PS80 adsorption during UF/DF was negligible. These excipient concentrations were the same as the formulation phase I.

Example 7—Buffer Screening

The pH in this example was screened from 6.2 to 7.4, and within this range all injectable buffers had been tested: Succinate, Histidine, Citrate, Phosphate, and Tris.

A) Type of Buffer and pH

In the first screening (assays #H04-150 to 172), the above buffers were tested at a concentration of 10 mM, in combination with several excipients that will be further detailed in Example 8—Additives Screening. Note that the buffer concentration was fixed at 10 mM and that its impact on HMW formation will be seen in the Section regarding Buffer Concentration (Example 7).

DSC

Figure 26:
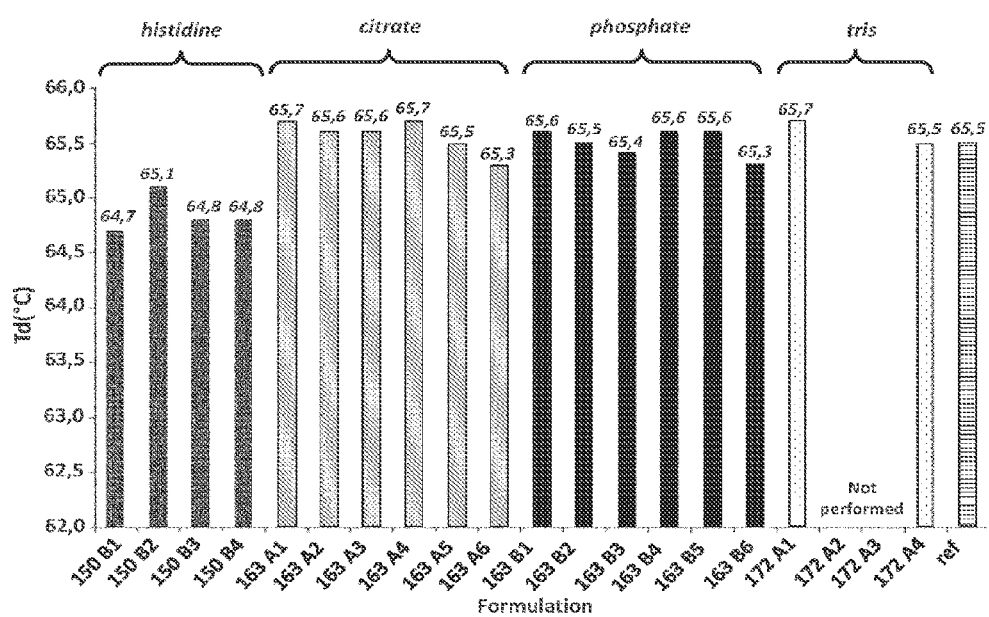
FIG. 26 is a graph showing DSC results for the first screening (assays #H04-150 to 172-pH-buffer screening).

DSC results showed that all formulations were comparable to the reference (Td1=65.5° C.), except for Histidine formulations, which were thermally slightly less stable (Td1=64.7° C. to 65.1° C.) (see FIG. 26).

Visual Inspection at Initial Time

All formulations were limpid and comparable to the reference, except for formulations at pH 6.2 and Histidine formulations at pH 6.6.

At pH 6.2, a decrease of solubility was observed for both tested buffers:
Histidine formulations precipitate at RT (see FIG. 27)
Succinate formulations were slightly opalescent at RT and one can observe the formation of a gel at 5° C. (see FIG. 27), which was reversible when the solution was returned to RT and gently shaken. Succinate may have chelating properties.
Histidine formulations at pH 6.6 were slightly more opalescent at RT than the reference.

HMW Evolution by SEC

As the results presented here were from 3 different series, the HMW evolution can not be compared directly, but only to the reference.
Histidine pH 6.6 was comparable to the reference at RT and slightly better at 5° C. (+2.4% for Histidine alone and +3.2% in 144 h for the reference).
Citrate pH 6.6 was slightly better at RT than the reference (+4.6% for Citrate alone and +5.2% in 24 h for the reference) and comparable to the reference at 5° C.
Phosphate pH 6.6 was slightly better at RT than the reference (+8.2% for Phosphate alone and +9.0% in 48 h for the reference) and comparable to the reference at 5° C.
Phosphate pH 7 was comparable to the reference at RT and 5° C.
Tris pH 7 was slightly worse than the reference at RT (+7.8% for Tris alone and +7.0% in 48 h for the reference) and comparable to the reference at 5° C.
Tris pH 7.4 was comparable to the reference at RT and 5° C.

Figure 28A:
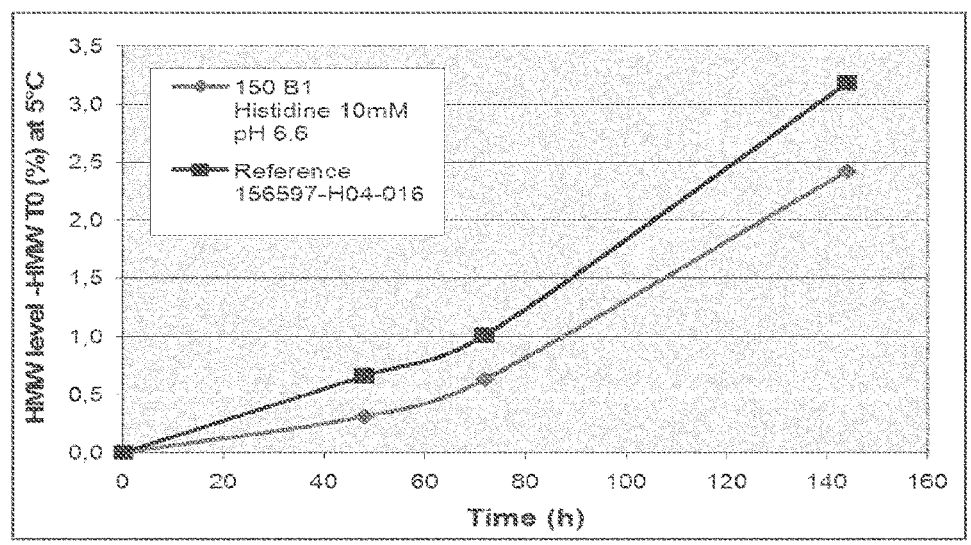
FIGS. 28A-C are graphs showing HMW evolutions for buffer screening at 5° C. (assays #H04-150 B1) and RT (assays #H04-163 A1, B1, B2 and H04-172 A1, A2) by SEC.
Figure 28B:
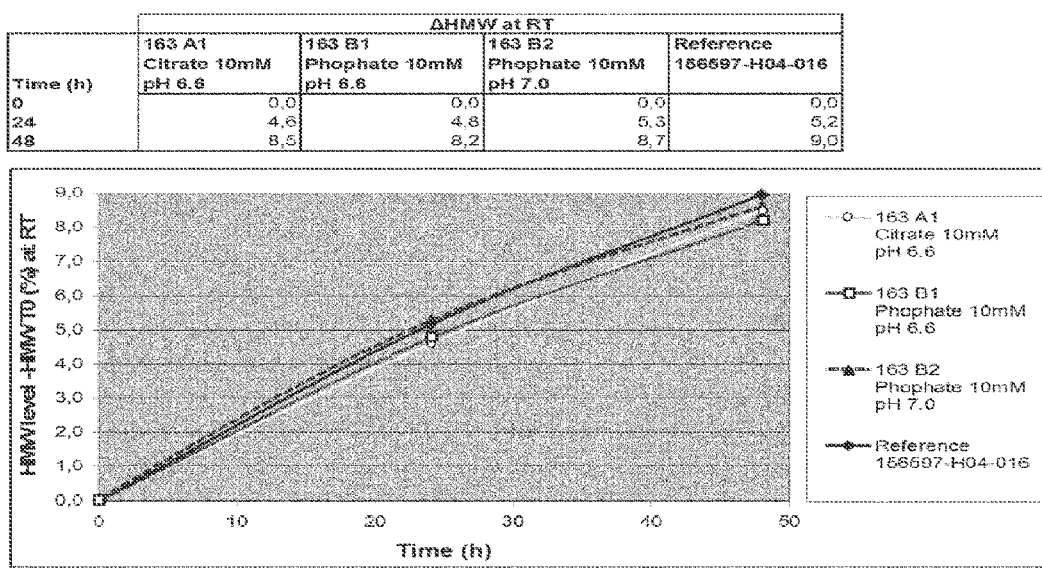
Figure 28C:
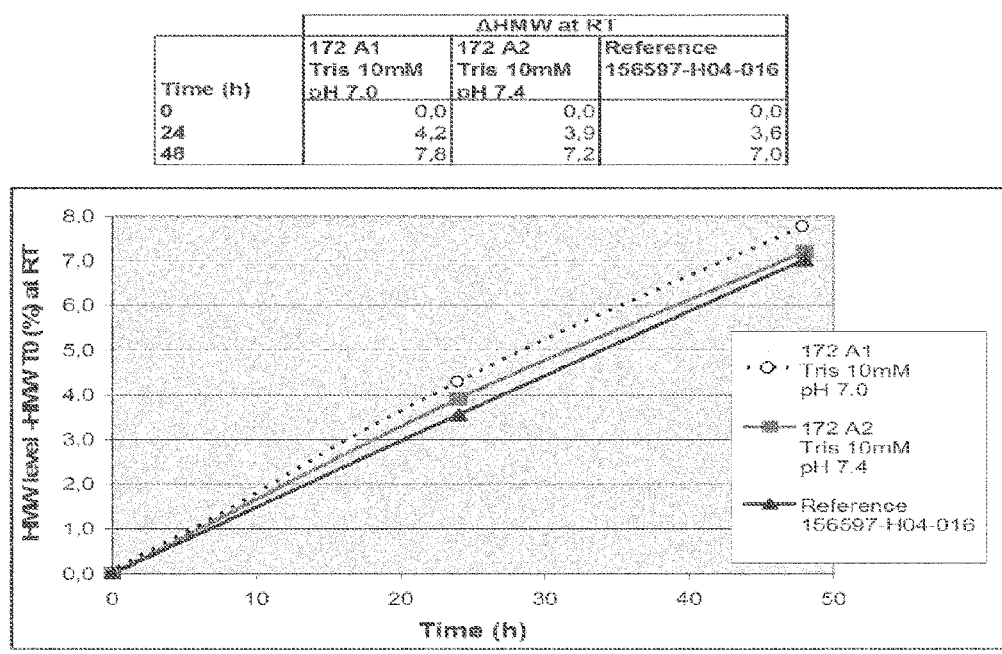

See FIG. 28.

Regarding HMW formation, at pH 6.6, Phosphate and Citrate were comparable, and at pH 7.0, Phosphate was slightly more stabilizing than Tris. The above buffers at 10 mM can not be directly compared to the formulation phase I/IIa, as the reference used for this screening was a lyophilisate manufactured from another batch (see Section above regarding References for SEC Measurements).

Conclusion

Regarding the buffering system screening at a concentration of 10 mM, it can be conclude that:
pH values around 6.2 (close to the pI) decreased Lead Antibody solubility:
A gel formation was observed with Succinate at pH 6.2
A precipitation was observed with Histidine at pH 6.2
In addition, Histidine should be avoided at pH 6.6 as the solution was opalescent and slightly less thermally stable
There is no clear tendency of pH effect within the range 6.6 to 7.4 on HMW formation for the buffers tested: Histidine, Citrate, Phosphate and Tris
Very weak effect of the buffer regarding HMW formation, although Citrate and Phosphate appeared to be the best buffers at 10 mM b) Fine Tuning of pH on Phase I/IIa Formulation In order to determine on the same run the influence of pH on HMW formation, the pH had been screened over the range 6.7 to 7.2 on the phase I formulation (assays #H04-187).

DSC

Figure 29:
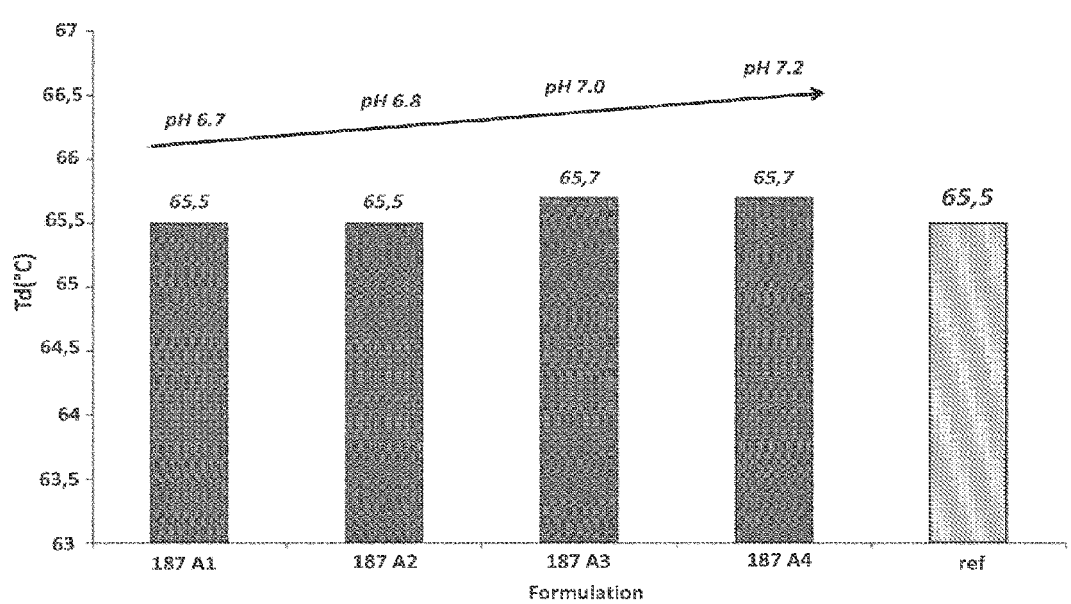
FIG. 29 is a graph showing DSC results for pH screening on Phosphate/Tris buffer (assays #H04-187).

DSC results showed that all formulations were comparable to the reference (pH 7.0) (see FIG. 29).

HMW Evolution by SEC

Figure 30:
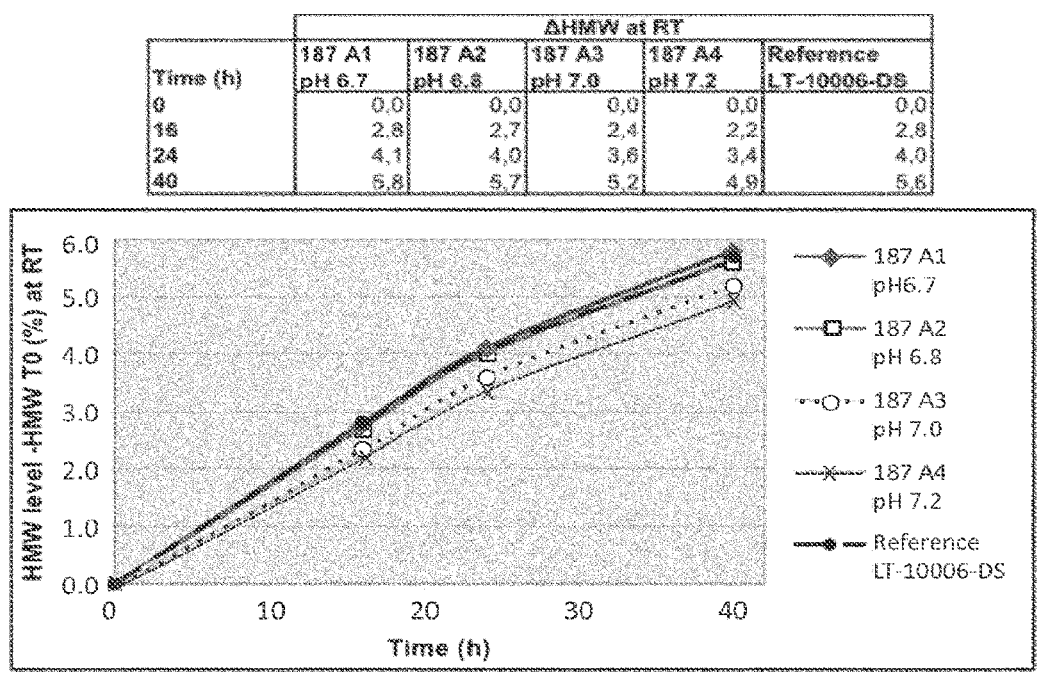
FIG. 30 is a graph showing HMW evolutions for pH screening on Phosphate/Tris buffer by SEC (assays #H04-187).

There was a slight tendency for decreasing HMW formation when increasing the pH from 6.7 to 7.2 (see FIG. 30), however this became significant only after 24 h at RT (+4.1% for pH 6.7 and +3.4% for pH 7.2).

Conclusion

With a buffer Phosphate 2.2 mM/Tris 1.3 mM (formulation phase I), there was a slight effect of pH over the range 6.7 to 7.2 after 24 h at RT. However, this effect was weak since it was not significant for the first 16 h. This confirmed the weak effect of pH on HMW formation in this pH range.

C) Buffer Concentration

Citrate and Phosphate were tested at smaller concentrations than 10 mM: 0, 1.75, and 5.25 mM, in order to investigate the influence of buffer concentration on HMW formation (assays #H04-185). The pH was set to an intermediate point in the tested range: pH=6.8. All formulations contained Glycine at 72 mM to adjust osmolality and, as said in the beginning of Section regarding Results and Discussion, 1.75% Sucrose and around 0.07% PS80.

DSC

Figure 31:
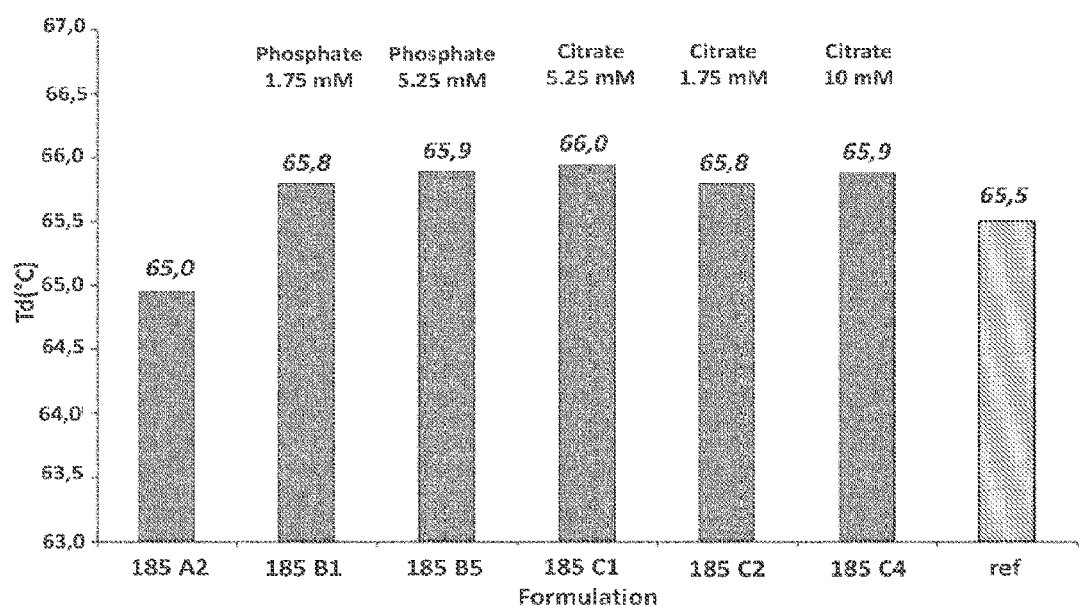
FIG. 31 is a graph showing DSC results for buffer concentration screening (assays #H04-185).

DSC results showed that all formulations were comparable to the reference (formulation phase I) (see FIG. 31).

Note that Glycine with no buffer (185A2) was slightly less stable than the other tested formulations (about 1° C. difference in Td1).

HMW Evolution by SEC

Figure 32A:
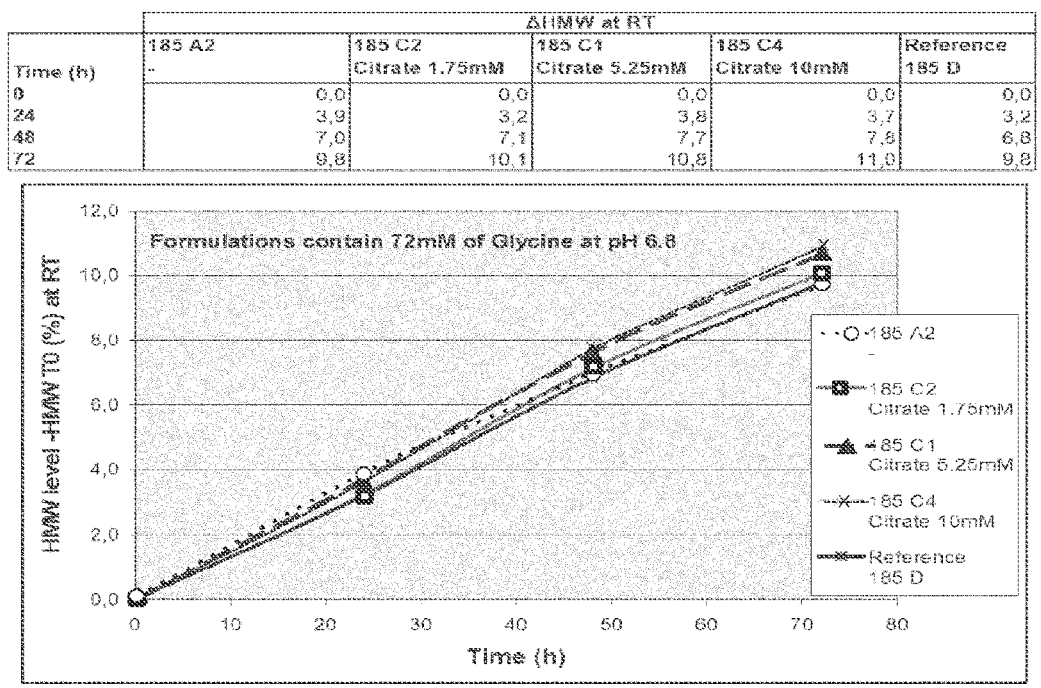
FIGS. 32A and B are graphs showing HMW evolutions with buffer concentration at RT by SEC (assays #H04-185).
Figure 32B:
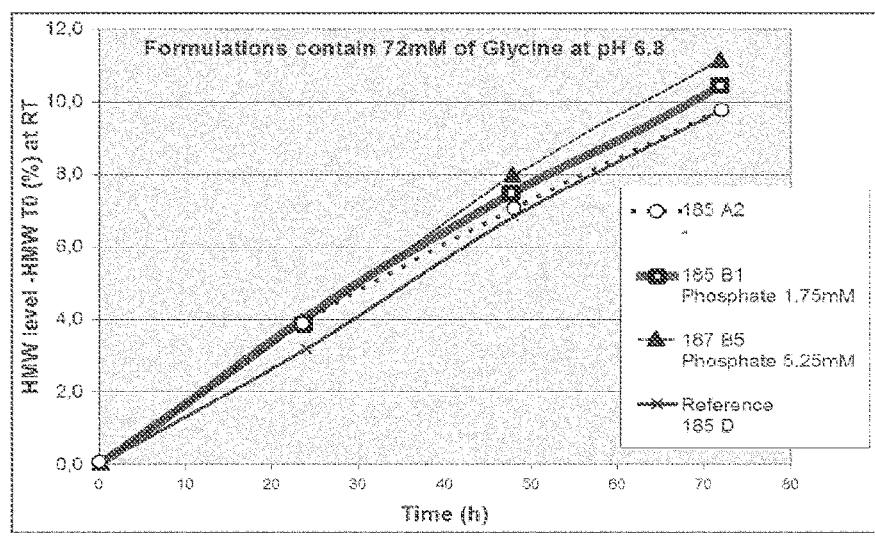

For both buffers tested, there was a slight tendency for decreasing HMW formation when decreasing buffer concentrations, the best results were obtained with no buffer and 1.75 mM in buffer (for e.g., +7.8% for Citrate 10 mM and +7.0% for no buffer in 48 h at RT) (see FIG. 32). Citrate at 1.75 mM and no buffer were comparable to the reference (for e.g., +7.1% for Citrate and +7.0% for no buffer in 48 h at RT whereas +6.8% for the reference).

Conclusion

Decreasing the buffer concentration had a slightly stabilizing effect on HMW formation kinetics. This effect was probably related to ionic strength. No buffer and a buffer Citrate 1.75 mM were the best candidates in term of HMW formation, followed closely by Phosphate 1.75 mM. Those buffers tested with Glycine 72 mM were comparable to the formulation phase I/IIa.

Example 8—Additives Screening

Screening of the additives Glycine, Proline, Histidine, and Tris had been done in combination with the buffer screening (first screening: assays #H04-150 to 172) in order to determine potential synergies between the excipients. Screening of the additives Sodium chloride, Sodium benzoate, Glycine, and Sucrose (second screening: assays #H04-185 to 190) had been done on Phosphate or Citrate, the best selected buffers from the first screening (Example 7).

The formulations contained 1.75% Sucrose and around 0.07% PS80.

A) Sodium Chloride and Sodium Benzoate

Sodium chloride and Sodium benzoate were tested to evaluate the effects of ionic strength and hydrophobic interactions, respectively, on HMW formation. These additives were tested on Phosphate 1.75 mM pH 6.8 at a concentration not exceeding the formulation phase I osmolality (165 mOsm/kg in the FDS).

DSC

DSC results showed that NaCl formulation was comparable to the reference (Td1=65.7° C. for NaCl and 65.6° C. for the reference) whereas sodium benzoate formulation was thermally slightly less stable (Td1=65.0° C.).

HMW Evolution by SEC

For both additives tested, there was a clear negative effect on HMW formation compared to the reference (for e.g., +5.2% for NaCl at 38.5 mM, +5.2% for sodium benzoate at 37.8 mM and +3.2% for the reference in 24 h at RT). The evolution being similar for both excipients, only NaCl results are shown here (see FIG. 33).

Conclusion

As seen for the buffer concentration, increasing ionic strength with NaCl or sodium benzoate had a clear negative effect on HMW formation kinetics. Furthermore, the effect of hydrophobic interactions on HMW kinetics, due to the addition of sodium benzoate was not observed.

B) Glycine, Proline, Histidine and Tris

Theses additives (glycine, proline, histidine, and Tris) were tested at a concentration of 10 mM (first screening: assays #H04-150 to 172).

DSC

DSC results showed that all formulations with the above additives were comparable to the formulation without (buffer alone).

HMW Evolution by SEC

The differences between formulations were weak, although tendencies could be seen after 48 h at RT and 6 days at 5° C.:
  Histidine buffer:
    At RT: Ø (no additives)=Glycine>Proline>Tris
    At 5° C.: Ø>Glycine=Proline>Tris
  Citrate buffer:
    At RT: Glycine>Proline=Histidine=Tris=(Tris+Glycine)>Ø
    At 5° C.: Glycine>Proline=Histidine=Tris=(Tris+Glycine)=Ø
  Phosphate buffer:
    At RT: Glycine=Proline=Ø>Histidine=Tris
    At 5° C.: Glycine>Proline=Ø=Histidine=Tris
  Tris buffer:
    At RT: Glycine>Ø=Histidine
    At 5° C.: Glycine=Ø=Histidine Conclusion Regarding HMW formation, the effects of these additives were weak, although tendencies could be seen:
  Glycine at 10 mM had a slight positive effect
  Histidine and Proline at 10 mM seemed to have no effect
  Tris at 10 mM had no stabilizing effect and could even have a slight destabilizing effect C) Sucrose and Glycine In the second screening (assays #H04-185), an additional quantity of Sucrose of 2.4% (in addition to the already 1.75% of Sucrose contained in all formulations, which gave a total of 4.15% (w/v) of Sucrose) and Glycine at a concentration of 72 mM were tested on the best selected buffers (see Section regarding Buffer Screening). These concentrations were maximized in order not to exceed the formulation phase I osmolality (165 mOsm/kg in the FDS).

DSC

DSC results showed that all Sucrose 2.4% and Glycine 72 mM formulations were comparable to the reference (for e.g., in the case of Sucrose, Td1=65.7° C. for Phosphate 1.75 mM and 65.6° C. for the reference).

HMW Evolution by SEC

The slight positive impact of Glycine was confirmed when compared to only Sucrose containing formulations for Citrate 1.75 mM and no buffer (see FIG. 34). However, this positive impact was only significant after 48 h at RT.

Conclusion

Regarding HMW formation, on the timescale of interest (<24 h at RT), Sucrose and Glycine formulations tested on the best buffer candidates were comparable to the formulation phase I.

Conclusions for Examples 7-8

For this study, around 50 formulations had been manufactured and compared side by side with the current phase I/IIa formulation. The pH screening ranged from 6.2 to 7.4, involving all injectable buffers within this pH range, alone or in combination with several excipients (all GRAS) in order to assess potential synergies between excipients.

Here were the main conclusions:
  pH values around 6.2 decrease Lead Antibody solubility: a gel formation and a precipitation were observed with Succinate and Histidine respectively;
  In addition, Histidine should be avoided at pH 6.6, as the solution was opalescent and slightly less thermally stable;
  In the range of pH between 6.6 to 7.4, there was no clear pH effect on HMW formation kinetics;
  Increasing ionic strength had a destabilizing effect on HMW formation kinetics;

Phosphate and Citrate were the best buffers tested, provided they were at low concentration such as 1.75 mM;

Among all the excipients tested, the best stabilizing effect had been obtained with Glycine 10 and 72 mM, and Sucrose 2.4%. However the stabilizing effect did not permit us to significantly slow down the HMW formation; and Proline, which has no effect at 10 mM, could be used as an isotonic agent (the effect of Proline at 91 mM (Proline concentration in the FDS phase I formulation) had not been assessed regarding HMW formation (e.g., assessing FDS formulation phase I with and without Proline).

In conclusion, the results of Examples 7-8 did not identify a new combination of excipients that could improve significantly the current formulation regarding HMW formation. That is, the results in Examples 7-8 confirm the results in Examples 1-6. The recommendation was to keep the current phase I/IIa formulation for phase IIb studies. The current formulation was therefore the following (see Table 31): Phosphate 6.5 mM/Tris 3.7 mM, pH 7.0, PS80 0.2% (w/v), Sucrose 5% (w/v), Proline 3% (w/v).

TABLE 31

Phase I/IIa/IIb Formulation description

| Component | Concentration |
| --- | --- |
| Lead Antibody | 100 mg/mL |
| Phosphate | 6.5 mM |
| Tris | 3.7 mM |
| Sucrose | 5% (w/v) |
| Proline | 3% (w/v) |
| PS80 | 0.2% (w/v) |

A quantitative adjustment of the current formulation (fine tuning of the excipient concentrations without adjunction of new excipients) may be performed for the phase III/commercial formulation.

What is claimed is:

1. A stable antibody formulation comprising:
   a bispecific anti-IL-4/anti-IL-13 antibody or an antigen binding fragment thereof, comprising a light chain of the formula VL1-linker-VL2 and a heavy chain of the formula VH1-linker-VH2, wherein VL1 and VH1 form an IL-13 antigen binding domain and VL2 and VH2 form an IL-4 antigen binding domain; and
   a buffering system suitable to maintain the pH of the formulation at about pH 7, wherein the buffering system comprises at least two buffers, wherein the buffering system comprises Tris buffer and Phosphate buffer; and
   wherein the formulation comprises mannitol.

2. The formulation of claim 1, wherein
   VL1 comprises the three CDR sequences of SEQ ID NO: 1;
   VH1 comprises the three CDR sequences of SEQ ID NO: 2;
   VL2 comprises the three CDR sequences of SEQ ID NO: 3; and
   VH2 comprises the three CDR sequences of SEQ ID NO: 4 or 5.

3. The formulation of claim 1, wherein
   VL1 comprises the amino acid sequence of SEQ ID NO: 1;
   VH1 comprises the amino acid sequence of SEQ ID NO: 2;
   VL2 comprises the amino acid sequence of SEQ ID NO: 3; and
   VH2 comprises the amino acid sequence of SEQ ID NO: 4 or 5.

4. The formulation of claim 1, wherein the light chain comprises the formula N-VL1-linker-VL2-CL, wherein CL is a light chain constant domain of an antibody, and wherein the heavy chain comprises the formula N-VH1-linker-VH2-CH1-CH2-CH3, wherein CH2-CH3 corresponds to the Fc domain of an antibody.

5. The formulation of claim 1, wherein the linker comprises the amino acid sequence of SEQ ID NO: 6.

6. The formulation of claim 1, wherein the antibody or antigen binding fragment thereof further comprises a constant region domain.

7. The formulation of claim 6, wherein the constant region domain is selected from the group consisting of CH1, CH2, CH3, and CL.

8. The formulation of claim 1, wherein the bispecific antibody or antigen binding fragment thereof is a humanized IgG4 bispecific antibody or antigen binding fragment thereof.

9. The formulation of claim 1, wherein the concentration of antibody or antigen binding fragment thereof is about 100 mg/mL.

10. The formulation of claim 1, wherein the buffering system concentration is about 10 mM.

11. The formulation of claim 1, wherein the Tris buffer concentration is about 3.7 mM.

12. The formulation of claim 1, wherein the Phosphate buffer concentration is about 6.3 mM.

13. The formulation of claim 1, wherein the Tris buffer concentration is about 3.7 mM and the Phosphate buffer concentration is about 6.3 mM.

14. The formulation of claim 1, wherein the formulation further comprises a non-ionic surfactant.

15. The formulation of claim 14, wherein the non-ionic surfactant concentration is about 0.05% to about 0.2% (w/v).

16. The formulation of claim 14, wherein the non-ionic surfactant is a polysorbate.

17. The formulation of claim 16, wherein the polysorbate is polysorbate 80.

18. The formulation of claim 17, wherein the polysorbate 80 concentration is about 0.05% to about 0.2% (w/v).

19. The formulation of claim 18, wherein the polysorbate 80 concentration is about 0.2% (w/v).

20. The formulation of claim 1, wherein the formulation further comprises a sugar.

21. The formulation of claim 20, wherein the sugar concentration is about 5% (w/v).

22. The formulation of claim 20, wherein the sugar is a disaccharide.

23. The formulation of claim 22, wherein the disaccharide is sucrose.

24. The formulation of claim 23, wherein the sucrose concentration is about 5% (w/v).

25. The formulation of claim 1, wherein the mannitol concentration is about 1% to about 3% (w/v).

26. The formulation of claim 1, wherein the mannitol concentration is about 3% (w/v).

27. The formulation of claim 1, wherein the formulation is a lyophilized formulation.

28. The formulation of claim 1, wherein the formulation exhibits stability regarding visible particles, sub-visible particles, low molecular weight proteins, and high molecular weight proteins.

29. A kit comprising a container comprising the formulation of claim 1 and instructions for the administration and use of the formulation.

30. A stable lyophilized antibody formulation comprising:
   about 100 mg/mL of a bispecific antibody or an antigen binding fragment thereof, wherein the antibody or antigen binding fragment thereof comprises a heavy chain variable region comprising the amino acid sequences of SEQ ID NOs: 2 and 4, and a light chain variable region comprising the amino acid sequences of SEQ ID NOs: 1 and 3;
   about 10 mM of a buffering system, wherein the buffering system comprises a Tris buffer concentration of about 3.7 mM and a Phosphate buffer concentration of about 6.3 mM;
   about 0.2% (w/v) polysorbate 80;
   about 5% (w/v) sucrose; and
   about 3% (w/v) mannitol;
   wherein the pH of the formulation is about pH 7.

* * * * *

UNITED STATES PATENT AND TRADEMARK OFFICE
CERTIFICATE OF CORRECTION

PATENT NO. : 10,005,835 B2
APPLICATION NO. : 14/787507
DATED : June 26, 2018
INVENTOR(S) : Sophie Carayon et al.

It is certified that error appears in the above-identified patent and that said Letters Patent is hereby corrected as shown below:

On the Title Page
Under "Notice", left-hand column, please replace "0 days. days." with --0 days--;
Section "OTHER PUBLICATIONS", right-hand column, Line 1: please replace "Wang et al. J. Pharmaceutical Scieince" with --Wang et al. J. Pharmaceutical Science--; and
Page 2, Section "OTHER PUBLICATIONS", right-hand column, Line 17: please replace "agains" with --against--.

Signed and Sealed this
Fifth Day of March, 2019

Andrei Iancu
*Director of the United States Patent and Trademark Office*

UNITED STATES PATENT AND TRADEMARK OFFICE
CERTIFICATE OF CORRECTION

PATENT NO. : 10,005,835 B2
APPLICATION NO. : 14/787507
DATED : June 26, 2018
INVENTOR(S) : Sophie Carayon et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 69 days.

Signed and Sealed this
Seventh Day of July, 2020

Andrei Iancu
*Director of the United States Patent and Trademark Office*